(12) United States Patent
Savarese et al.

(10) Patent No.: US 9,156,826 B2
(45) Date of Patent: Oct. 13, 2015

(54) ASYMMETRICAL REVERSIBLE NEUROMUSCULAR BLOCKING AGENTS OF ULTRA-SHORT, SHORT, OR INTERMEDIATE DURATION

(71) Applicant: Cornell University, Ithaca, NY (US)

(72) Inventors: John J. Savarese, Southbury, CT (US); Jeff D. McGilvra, Belgium, WI (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/411,060

(22) PCT Filed: Jun. 28, 2013

(86) PCT No.: PCT/US2013/048771
§ 371 (c)(1),
(2) Date: Dec. 23, 2014

(87) PCT Pub. No.: WO2014/005122
PCT Pub. Date: Jan. 3, 2014

(65) Prior Publication Data
US 2015/0191453 A1    Jul. 9, 2015

Related U.S. Application Data

(60) Provisional application No. 61/666,244, filed on Jun. 29, 2012, provisional application No. 61/703,991, filed on Sep. 21, 2012, provisional application No. 61/817,706, filed on Apr. 30, 2013.

(51) Int. Cl.

| | |
|---|---|
| *C07D 401/12* | (2006.01) |
| *A61K 31/4725* | (2006.01) |
| *C07D 405/12* | (2006.01) |
| *C07D 217/20* | (2006.01) |
| *A61K 31/5377* | (2006.01) |
| *C07D 405/10* | (2006.01) |
| *A61K 45/06* | (2006.01) |

(52) U.S. Cl.
CPC .......... *C07D 405/12* (2013.01); *A61K 31/4725* (2013.01); *A61K 31/5377* (2013.01); *A61K 45/06* (2013.01); *C07D 217/20* (2013.01); *C07D 401/12* (2013.01); *C07D 405/10* (2013.01)

(58) Field of Classification Search
None
See application file for complete search history.

(56) References Cited

U.S. PATENT DOCUMENTS

| 4,761,418 A | 8/1988 | Swaringen, Jr. et al. |
| 8,148,398 B2 | 4/2012 | Savarese |
| 2010/0174082 A1 | 7/2010 | Arad et al. |

FOREIGN PATENT DOCUMENTS

| WO | WO-03070243 A1 | 8/2003 |
| WO | WO-2014005122 A2 | 1/2014 |
| WO | WO-2014005122 A3 | 1/2014 |

OTHER PUBLICATIONS

"International Application Serial No. PCT/US2013/048771, International Search Report mailed Dec. 20, 2013", 2 pgs.
"International Application Serial No. PCT/US2013/048771, Written Opinion mailed Dec. 20, 2013", 3 pgs.
"International Application Serial No. PCT/US2013/048771, International Preliminary Report on Patentability mailed Jan. 8, 2015", 5 pgs.

*Primary Examiner* — Zinna Northington Davis
(74) *Attorney, Agent, or Firm* — Schwegman Lundberg & Woessner, P.A.

(57) ABSTRACT

We describe ultra-short, short, and intermediate duration neuromuscular blocking compounds, reversible by cysteine or similar compounds, that are bisquaternary diesters of chlorofumaric, fumaric, or maleic acids where the quaternary groups are very different, creating a highly asymmetrical molecule where one quaternary includes an isoquinolinium ring system and the other includes a morpholinium, piperidinium, piperazinium, or pyrrolidinium system, pharmaceutical compositions, methods to use such compounds and compositions, and kits.

35 Claims, 5 Drawing Sheets

ASYMMETRICAL REVERSIBLE NEUROMUSCULAR BLOCKING AGENTS OF ULTRA-SHORT, SHORT, OR INTERMEDIATE DURATION

CROSS-REFERENCE TO RELATED APPLICATIONS

This application is a national stage application under 35 U.S.C. §371 of PCT/US2013/048771, filed Jun. 28, 2013, and published as WO 2014/005122 A2 on Jan. 3, 2014, which claims the priority filing dates of U.S. provisional applications, Ser. Nos. 61/666,244, filed Jun. 29, 2012; 61/703,991, filed Sep. 21, 2012; and 61/817,706, filed May 14, 2013; which applications and publication are incorporated by reference as if reproduced herein and made a part hereof in their entirety, and the benefit of priority of each of which is claimed herein the disclosures of which are incorporated by reference herein in their entireties.

BACKGROUND

Neuromuscular blocking agents are commonly given intravenously during general anesthesia to relax the muscles, intubate the trachea and facilitate controlled ventilation.

At present, two types (classes) of neuromuscular blocking agents predominate in clinical practice:

(1) Neuromuscular blocking agents of intermediate duration. Examples are rocuronium, vecuronium, and cisatracurium. This type of agent is commonly given by repetitive bolus for maintenance of neuromuscular blockade, and may also be given in high dosage to facilitate intubation of the trachea. Recovery from neuromuscular blockade is relatively slow and commonly requires antagonism (reversal) by administration of an anticholinesterase, such as neostigmine, at the end of the anesthesia, to restore normal function within a reasonably short time (10-15 min).

(2) Neuromuscular blocking agents of short or ultra-short duration. Examples are mivacurium (short) and succinylcholine (ultra-short). This type of agent commonly displays a fast onset of effect and is given to facilitate intubation of the trachea. A second convenient and safe usage is for maintenance of blockade by continuous infusion, where spontaneous recovery occurs rapidly on discontinuation of the infusion.

Both the above classes of neuromuscular blocking agents have disadvantages. Slow recovery from the intermediate-duration agents requires administration of the antagonist neostigmine. The relatively slow onset of blockade of this type (class) of neuromuscular blocking agents requires high dosage to enable tracheal intubation within 60-90 seconds. This high dosage lengthens blockade considerably, to as much as one to three hours or more, during which time the block may be too deep to be antagonized by neostigmine.

The short and ultra-short acting agents mivacurium and succinylcholine are both metabolized by pseudocholinesterase, an enzyme system which may be abnormal for a wide variety of reasons; in such cases, the blockade produced by these drugs is markedly prolonged.

Though it is still in common usage because of its fast onset which facilitates early (60 sec) intubation of the trachea, succinylcholine has many other well-known undesirable side-effects such as cardiac arrhythmias and muscle pain, and the drug is a triggering agent for the often fatal malignant hyperthermia syndrome. One of the disadvantages of mivacurium is its histamine releasing property which, though relatively weak, requires improvement such that it is reduced or abolished entirely. Further, the onset of mivacurium-induced block is comparatively slow vis-a-vis succinylcholine.

SUMMARY

The invention is directed, in various embodiments, to neuromuscular blocking agents (NMBAs) of ultra-short, short, or intermediate during, wherein the neuromuscular blockade (NMB) induced by the agents is reversible, such as by administration of cysteine or related compounds; to methods of use of the neuromuscular blocking agents; to methods of synthesis of the neuromuscular blocking agents; and to kits comprising a neuromuscular blocking agent, and a reversing agent (antagonist) such as cysteine or a related compound, for use in inducing and reversing neuromuscular blockage such as in surgical patients.

In various embodiments, the invention provides a neuromuscular blocking agent of formula (I)

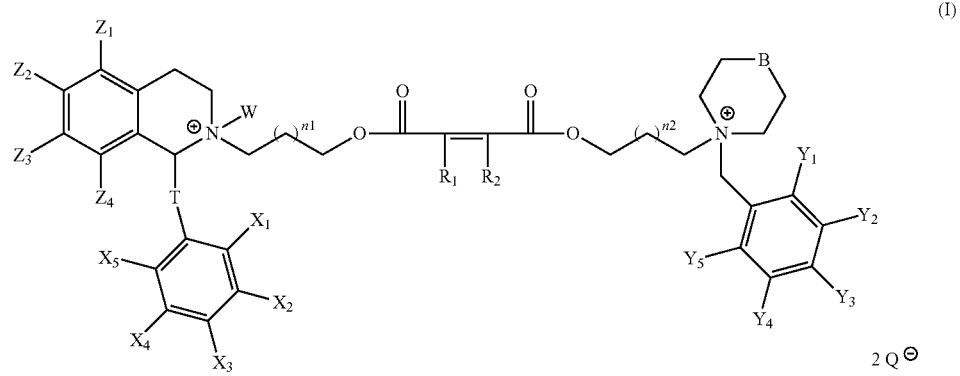

(I)

wherein each of $R_1$ and $R_2$ is independently selected from the group consisting of hydrogen and halogen, and $R_1$ and $R_2$ can be disposed in a cis or a trans configuration on the two double-bonded carbon atoms to which $R_1$ and $R_2$ are respectively bonded;

T is selected from the group consisting of $CH_2$ and $CH_3$, wherein if T is $CH_3$, the phenyl group with the $X_1$-$X_5$ substituents is not present;

B is selected from the group consisting of $CH_2$, O, NR, and a direct single bond, wherein R is H, $(C_{1-6})$alkyl, or $(C_{1-6})$acyl;

n1 and n2 are each independently equal to 0, 1, 2, or 3;

each of $X_1$, $X_2$, $X_3$, $X_4$, and $X_5$, is independently at each occurrence hydrogen, hydroxy or methoxy, or any two adjacent $X_1$, $X_2$, $X_3$, $X_4$, or $X_5$, together form a methylenedioxy or ethylenedioxy group; each of $Y_1$, $Y_2$, $Y_3$, $Y_4$, and $Y_5$, is independently at each occurrence hydrogen, hydroxy or methoxy, or any two adjacent $Y_1$, $Y_2$, $Y_3$, $Y_4$, or $Y_5$, together form a methylenedioxy or ethylenedioxy group;

each of $Z_1$, $Z_2$, $Z_3$, and $Z_4$, is independently at each occurrence hydrogen, hydroxy or methoxy, or any two adjacent $Z_1$, $Z_2$, $Z_3$, or $Z_4$, together form a methylenedioxy or ethylenedioxy group;

W is selected from the group consisting of methyl and a benzyl group of formula:

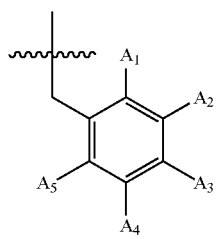

wherein each of $A_1$, $A_2$, $A_3$, $A_4$, and $A_5$, is independently at each occurrence hydrogen or methoxy, or any two adjacent $A_1$, $A_2$, $A_3$, $A_4$, or $A_5$, together form a methylenedioxy or ethylenedioxy group, and a wavy line indicates a point of bonding; and, wherein each $Q^\ominus$ is an independently selected pharmaceutically acceptable anion.

In various embodiments, the compound of formula (I) is of the (R)-absolute configuration at the carbon atom bearing the group T. In various embodiments, the compound of formula (I) has a ring trans relationship between the group T and the linker chain bonding the isoquinolinium quaternary moiety to the ester; i.e., group T and group W can be ring cis to each other.

The invention, in various embodiments, is directed to a dosage form comprising an amount of the neuromuscular blocking agent of the invention that is sufficient to paralyze a mammalian subject, in a suitable biocompatible solvent, such as sterile saline. The dosage form can be compatible with parenteral administration of the NMBA to the patient.

The invention can further provide a method of inducing a neuromuscular blockade in a mammal, which can be a human, or can be a non-human mammal, for therapeutic purposes comprising administering to the mammal the composition described above. The mammal can also be subjected to general anesthesia. The therapeutic purposes can comprise a surgical procedure. The NMBA can be administered to the patient, for example, in a dose ranging from about 0.01 to 1 mg/kg body weight. The inventors herein have unexpectedly discovered that a therapeutic dose for induction of NMB does not appear to induce tachycardia in rhesus monkeys, which is advantageous in comparison with succinylcholine, an art ultra-short acting NMBA.

The invention provides, in various embodiments, a method of reversing a neuromuscular blockade in a mammal comprising administering to the mammal an effective amount of at least one of L-cysteine, D-cysteine, or a mixture thereof; N-acetylcysteine; glutathione; homocysteine; methionine; S-adenosyl-methionine; or penicillamine; or any combination thereof; or a pharmaceutically acceptable salt thereof; wherein the neuromuscular blockade is generated by methods, compounds, or compositions described herein. The neuromuscular blocker antagonist can be administered intravenously, in combination with a pharmaceutically acceptable liquid carrier, in a dosage of about 0.1 mg/kg to about 500 mg/kg.

The invention provides, in various embodiments, a kit comprising, separately packaged, (a) an effective amount of a neuromuscular blocking agent described herein, (b) an effective amount of an antagonist to the neuromuscular blocking agent described herein, and optionally, (c) instructions directing the user to employ the antagonist to reverse the effects of the blocking agent on a mammal to which the blocking agent is administered; wherein the antagonist comprises an effective amount of at least one of L-cysteine, D-cysteine, or a mixture thereof; N-acetylcysteine; glutathione; homocysteine; methionine; S-adenosyl-methionine; or penicillamine; or a pharmaceutically acceptable salt thereof. The neuromuscular blocking agent and/or the antagonist of the neuromuscular blocking agent in the kit can be a powder or soluble solid. The neuromuscular blocking agent and the antagonist thereof can be administered intravenously, in combination with a pharmaceutically acceptable liquid carrier, and the instructions can include directions for mixing the powder or soluble solid with a pharmaceutically acceptable liquid carrier. Or, the NMBA, the antagonist (reversing agent), or both, can be a solution in a suitable biocompatible solvent, such as sterile saline, at an appropriate pH.

DETAILED DESCRIPTION

Figure 1:
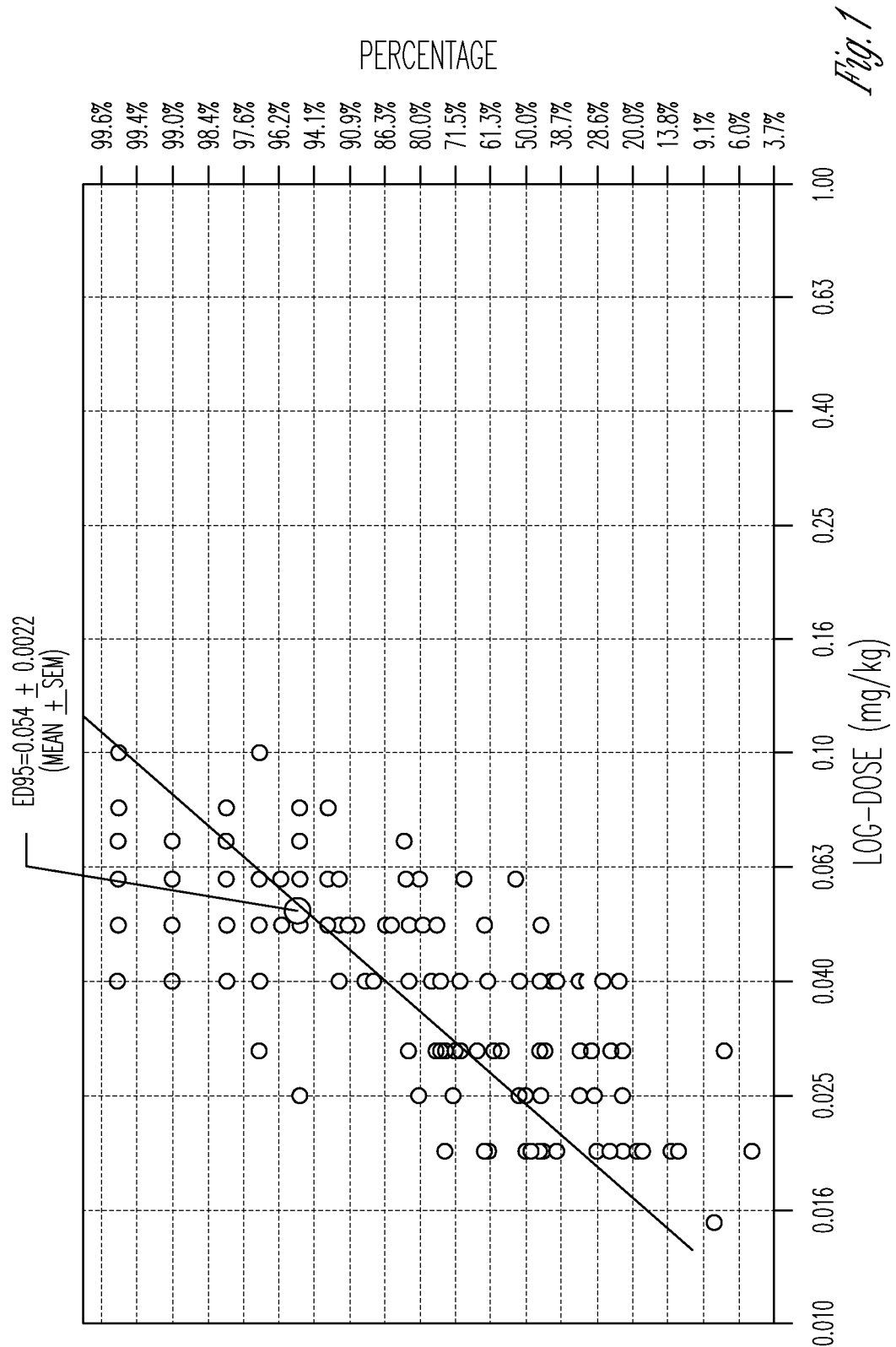
FIG. 1 is a graph showing data from a dose-response study for generation of NMB in a rhesus monkey for a compound of the invention 1759-50.

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

The expression "effective amount", when used to describe induction of neuromuscular blockade or reversal of that blockade refers to the amount of a compound of the invention that is effective to bring about the desired effects in an individual being treated, which is adjusted based on the knowledge and discretion of the attending physician and takes into account significant medical factors, such as body mass of the patient. In particular, a "therapeutically effective amount" refers to an amount effective, at dosages and for periods of time necessary, to achieve the desired therapeutic result of NMB or reversal of NMB. A therapeutically effective amount is also one in which any toxic or detrimental effects of compounds of the invention are outweighed by the therapeutically beneficial effects.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

When a group, e.g., an "alkyl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, less than the total number of carbon atoms in the universe and bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded, as the number of atoms in the group cannot be infinite.

The terms "halo" or "halogen" or "halide" by themselves or as part of another substituent mean, unless otherwise stated, a fluorine, chlorine, bromine, or iodine atom, preferably, fluorine, chlorine, or bromine.

The term "hydroxy" or "hydroxyl" refers to an OH group.

The term "alkoxy" or "alkoxyl" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl amine is an amide; an acylated hydroxyl group is an ester, and so forth.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention.

Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention. "Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided.

Provisos may apply to any of the disclosed categories or embodiments wherein any one or more of the other above disclosed embodiments or species may be excluded from such categories or embodiments.

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. All commercially available chemicals were obtained from Aldrich, Alfa Aesare, Wako, Acros, Fisher, Fluka, Maybridge or the like and were used without further purification, except where noted. Dry solvents are obtained, for example, by passing these through activated alumina columns.

The present invention further embraces isolated compounds of the invention. The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of the invention or a mixture of compounds of the invention, which contains the named compound or mixture of compounds of the invention in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

Optical Isomerism

It will be understood that when compounds of the present invention contain one or more chiral centers, the compounds may exist in, and may be isolated as single and substantially pure enantiomeric or diastereomeric forms or as racemic mixtures. The present invention therefore includes any possible enantiomers, diastereomers, racemates or mixtures thereof of the compounds of the invention.

The compounds of the invention, or compounds used in practicing methods of the invention, may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. In maleate compounds of the invention, the central double bond carries $R_1$ and $R_2$ groups of formula (I) as described and claimed herein in a cis orientation. In fumarate and chlorofumarate compounds of the invention, the central double bond carries $R_1$ and $R_2$ groups in a trans configuration.

Compounds of the invention, or compounds used in practicing methods of the invention, may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic ring may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated as "cis/trans mixtures" For example, in the compounds of formula (IR), or of formula (IS), the groups "T" and "W" are in the cis orientation to each other. In the compounds of formula (I), the groups "T" and "W" can be in a cis or a trans orientation to each other.

Individual enantiomers and diastereomers of contemplated compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated as having an (R) absolute configuration, and if the descending rank of the other groups proceeds counterclockwise, the molecule is designated as having an (S) absolute configuration. In the example in the Scheme below, the Cahn-Ingold-Prelog ranking is A>B>C>D. The lowest ranking atom, D is oriented away from the viewer.

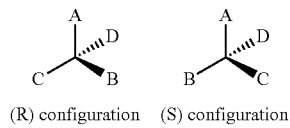

(R) configuration    (S) configuration

A carbon atom bearing the A-D atoms as shown above is known as a "chiral" carbon atom, and the position of such a carbon atom in a molecule is termed a "chiral center."

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" or "isolated enantiomer" means a compound which has been substantially purified from the corresponding optical isomer(s) of the same formula. Preferably, the isolated isomer is at least about 80%, more preferably at least 90% enantiomerically pure, even more preferably at least 98% enantiomerically pure, most preferably at least about 99% enantiomerically pure, by weight. By "enantiomeric purity" is meant the percent of the predominant enantiomer in an enantiomeric mixture of optical isomers of a compound. A pure single enantiomer has an enantiomeric purity of 100%.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Another well-known method of obtaining separate and substantially pure optical isomers is classic resolution, whereby a chiral racemic compound containing an ionized functional group, such as a protonated amine or carboxylate group, forms diastereomeric salts with an oppositely ionized chiral nonracemic additive. The resultant diastereomeric salt forms can then be separated by standard physical means, such as differential solubility, and then the chiral nonracemic additive may be either removed or exchanged with an alternate counter ion by standard chemical means, or alternatively the diastereomeric salt form may retained as a salt to be used as a therapeutic agent or as a precursor to a therapeutic agent.

Overview

Compounds of the present invention are novel structurally in that they are bisquaternary diesters of chlorofumaric, fumaric, or maleic acids where the quaternary groups are very different, creating a highly asymmetrical molecule where one quaternary moiety includes an isoquinolinium ring system, optionally substituted with oxygen-containing groups such as hydroxyl, methoxyl, methylenedioxy, and ethylenedioxy, and the other quaternary moiety includes a morpholinium, piperidinium, piperazinium, or pyrrolidinium system that is disposed adjacent to a benzyl group, that can be substituted with oxygen-containing groups such as hydroxyl, methoxyl, methylenedioxy, and ethylenedioxy.

The novel asymmetrical diester structure is based on a central olefinic fumaric, chlorofumaric or maleic acid and can confer unique properties on the compounds, such as the duration of action, and the reversibility of the neuromuscular blockade in a patient by administration to the patient of a compound such as cysteine or other sulfur-containing molecule that can react with the double bond of the chlorofumaric, fumaric, or maleic diester group that links the two quaternary moieties. While not wishing to be bound by theory, it is believed that addition of an aminoacid such as cysteine to the reactive double bond of the bisquaternary diester serves to greatly increase hydrophilicity and excretion of the neuromuscular blocking agent, while reducing its potency at the receptor.

Neuromuscular blocking agents (NMBA) of the invention can include the following individual specific structural features:

(1) Ultra-short or short duration (<10 min or 10-15 min at ED 95 dosage in monkeys).

(2) Intermediate duration (15-25 min in monkeys).

(3) Cysteine attack on the central double bond, yielding an inactive adduct which then undergoes spontaneous alkaline hydrolysis to fragments which are also inactive and readily soluble in water, and therefore easily excretable in urine. This form of reversal is unique among NMBA's because cysteine converts the active molecule to inactive degradation products in a chemical reaction which requires no organic catalyst (enzyme system) and no organ of elimination such as the liver or kidney. As a result, normal function returns within 2-3 min of cysteine administration.

(4) Duration in vivo is correlated with the rate of cysteine attack in vitro.

(5) A significant reduction of the side-effect of circulatory responses suggestive of histamine release is achieved in especially the mixed isoquinolinium/morpholinium diester compounds.

(6) Rapid and complete antagonism of neuromuscular blockade within 2-3 min at any time may be achieved by either D or L-cysteine given i.v., even following large doses of the NMBA of 4-Sx ED95.

Compounds of the Invention

In various embodiments, the invention provides a neuromuscular blocking agent of formula (I)

wherein each of $R_1$ and $R_2$ is independently selected from the group consisting of hydrogen and halogen, and $R_1$ and $R_2$ can be disposed in a cis or a trans configuration on the two double-bonded carbon atoms to which $R_1$ and $R_2$ are respectively bonded;

T is selected from the group consisting of $CH_2$ and $CH_3$, wherein if T is $CH_3$, the phenyl group with the $X_1$-$X_5$ substituents is not present;

B is selected from the group consisting of $CH_2$, O, NR, and a direct single bond, wherein R is H, $(C_{1-6})$alkyl, or $(C_{1-6})$ acyl;

n1 and n2 are each independently equal to 0, 1, 2, or 3;

each of $X_1$, $X_2$, $X_3$, $X_4$, and $X_5$, is independently at each occurrence hydrogen, hydroxy or methoxy, or any two adjacent $X_1$, $X_2$, $X_3$, $X_4$, or $X_5$, together form a methylenedioxy or ethylenedioxy group; each of $Y_1$, $Y_2$, $Y_3$, $Y_4$, and $Y_5$, is independently at each occurrence hydrogen, hydroxy or methoxy, or any two adjacent $Y_1$, $Y_2$, $Y_3$, $Y_4$, or $Y_5$, together form a methylenedioxy or ethylenedioxy group;

each of $Z_1$, $Z_2$, $Z_3$, and $Z_4$, is independently at each occurrence hydrogen, hydroxy or methoxy, or any two adjacent $Z_1$, $Z_2$, $Z_3$, or $Z_4$, together form a methylenedioxy or ethylenedioxy group;

W is selected from the group consisting of methyl and a benzyl group of formula:

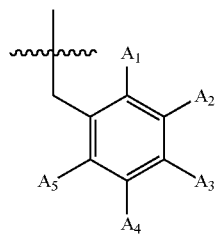

wherein each of $A_1$, $A_2$, $A_3$, $A_4$, and $A_5$, is independently at each occurrence hydrogen or methoxy, or any two adjacent $A_1$, $A_2$, $A_3$, $A_4$, or $A_5$, together form a methylenedioxy or ethylenedioxy group, and a wavy line indicates a point of bonding; and, in a cis or a trans configuration with respect to the ring of the isoquinolinium moiety that bears them. For example, the group T and the group W can be disposed in a cis ring configuration, i.e., disposed on the same side of the ring, while the group that links to the unsaturated diester moiety bearing groups $R_1$ and $R_2$.

The groups $R_1$ and $R_2$ are each independently selected from hydrogen and halogen, and the disposition of $R_1$ and $R_2$ around the double bond of the carbon atoms that respectively bear the $R_1/R_2$ groups can be cis or trans. Accordingly, the invention provides bis-quaternary diesters including maleates, halomaleates, dihalomaleates, fumarates, halofumarates, and dihalofumarates. An example of a halogenated diester is a chlorfumarate bis-quaternary diester.

Each of the two diastereomers of formula (I) itself possesses two possible enantiomeric forms; for the diastereomer wherein the group T and the group W are in the ring cis configuration (i.e., group T and the linker to the ester group are in the ring trans configuration), these two enantiomers are shown as formulas (IR) and (IS), below. The (R) and the (S) designations are applied based on the absolute configuration of the carbon atom bearing group T. The designated absolute configuration of the ammonium nitrogen atom bearing group W can vary depending upon the identity of group W in the CIP rules discussed above, but in formula (IR), having an (R) absolute configuration at the carbon atom bearing group T, and in formula (IS) having an (S) absolute configuration at the carbon atom bearing group T, the group W is disposed in a ring cis configuration to T, while the linking chain to the central unsaturated diester moiety is ring trans to T.

Accordingly, the invention provides, in various embodiments, a neuromuscular blocking agent of claim 1 of formula (IR)

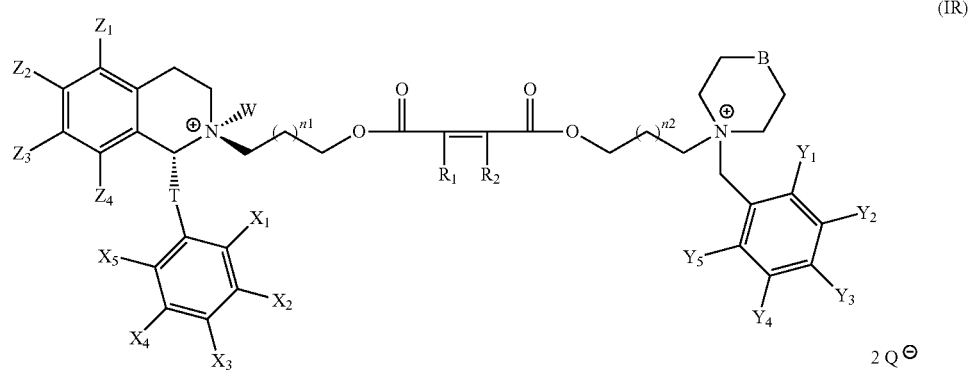

(IR)

wherein each $Q^\ominus$ is an independently selected pharmaceutically acceptable anion.

The NMBA of formula (I) possesses in its core structure two chiral centers disposed adjacent to each other in the isoquinolinium quaternary moiety, i.e., the carbon atom bearing group T and the quaternarized ammonium bearing group W. Accordingly, the group T and the group W can be disposed wherein $R_1$, $R_2$, $n1$, $n2$, $X_1$, $X_2$, $X_3$, $X_4$, $X_5$, $Y_1$, $Y_2$, $Y_3$, $Y_4$, $Y_5$, $Z_1$, $Z_2$, $Z_3$, $Z_4$, $A_1$, $A_2$, $A_3$, $A_4$, $A_5$, W, B, $Q^\ominus$, and T are as defined above for formula (I).

The invention also provides the enantiomeric form of formula (IR), i.e., a neuromuscular blocking agent of formula (IS),

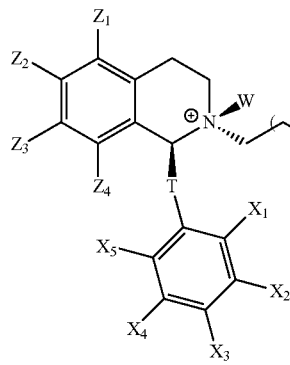
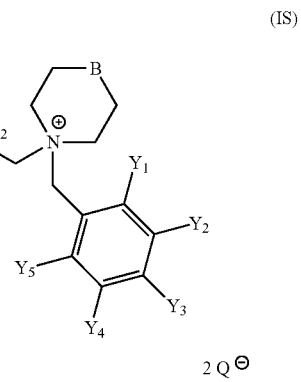

(IS)

wherein $R_1$, $R_2$, n1, n2, $X_1$, $X_2$, $X_3$, $X_4$, $X_5$, $Y_1$, $Y_2$, $Y_3$, $Y_4$, $Y_5$, $Z_1$, $Z_2$, $Z_3$, $Z_4$, $A_1$, $A_2$, $A_3$, $A_4$, $A_5$, W, B, $Q^\ominus$, and T are as defined above for formula W.

In all of formulas (I), (IR), and (IS), the two positive electrical charges of the bis-quaternium NMBA are balanced by two anionic charges, which can be comprised by a single multiply-charged anion (e.g., sulfate, phosphate), or by two singly-charged anions (e.g., halide, such as chloride). Each $Q^\ominus$ is an independently selected pharmaceutically acceptable anion in the above compositions of matter.

Each of the rings bearing groups X, Y, Z, or (optionally) A, can be a substituted ring as defined above. For example, in various embodiments, the invention provides a neuromuscular blocking agent of the invention wherein at least one of $X_1$, $X_2$, $X_3$, $X_4$, or $X_5$, is non-hydrogen; or at least one of $Y_1$, $Y_2$, $Y_3$, $Y_4$, or $Y_5$, is non-hydrogen; or at least one of $Z_1$, $Z_2$, $Z_3$, or $Z_4$, is non-hydrogen; or at least one of $A_1$, $A_2$, $A_3$, $A_4$, or $A_5$, is non-hydrogen; or any combination thereof. As seen in the specific examples, below, rings can be substituted at any available position, and are often substituted on the 4-position or disubstituted on the 3,4-positions of the phenyl groups, and on the 6,7-position of the isoquinolinium group.

In other embodiments, the invention can provide a NMBA of the invention wherein $X_2$ and $X_3$ are both methoxy or together form methylenedioxy or ethylenedioxy, or $Y_2$ and $Y_3$ are both methoxy or together form methylenedioxy or ethylenedioxy, or $Z_2$ and $Z_3$ are both methoxy or together form methylenedioxy or ethylenedioxy, or any combination thereof.

More specifically, the invention can provide a neuromuscular blocking agent of the invention wherein T is $CH_2$ and the phenyl ring bearing $X_1$-$X_5$ is present. The term "compound of the invention" as used herein refers to a compound of formula (I), in any of its embodiments, or an exemplary compound, as disclosed and claimed herein.

With respect to the quaternary moiety including a morpholinium (B is oxygen), piperidinium (B is $CH_2$), piperazinium (B is NR), or pyrrolidinium (B is a direct single bond) system that is disposed adjacent to a benzyl group, i.e., comprising group B, a quaternary center is permanently present due to the presence of the quaternarized nitrogen atom in the chain connecting the Y-substituted phenyl ring with the central unsaturated diester group. In various embodiments, B can be an oxygen atom (morpholinium series). In other embodiments, B can be a direct single bond (pyrrolidinium series).

The two linking chains bonding each of the two quaternary moieties each contain at least two carbon atoms and an oxygen atom which forms an ester linkage with the central chlorofumarate, maleate, etc. One of the carbon atoms of each linker is bonded directly to the quaternary nitrogen atom, i.e., of the isoquinolinium group in one quaternary moiety and of the ring comprising group B in the other quaternary moiety. For example, when each variable n1 and n2 is equal to 1, the each linker comprises three backbone carbon atoms connecting the respective quaternary nitrogen atom to the respective ester oxygen atom. In other embodiments, two, four, or five backbone atoms are contained by each linker group.

The invention provides, in various embodiments, a maleate ester, i.e., when the $R_1$ and $R_2$ groups are disposed in a cis configuration, and $R_1$ and $R_2$ are both hydrogen. For example, a NMBA of the invention comprising a maleate ester can be selected from the group consisting of:

Morpholinium maleates

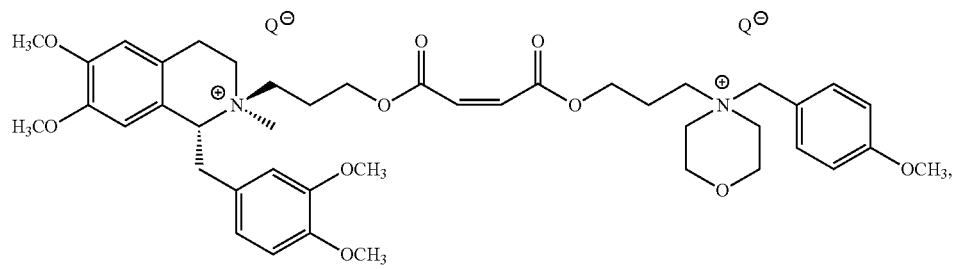

-continued
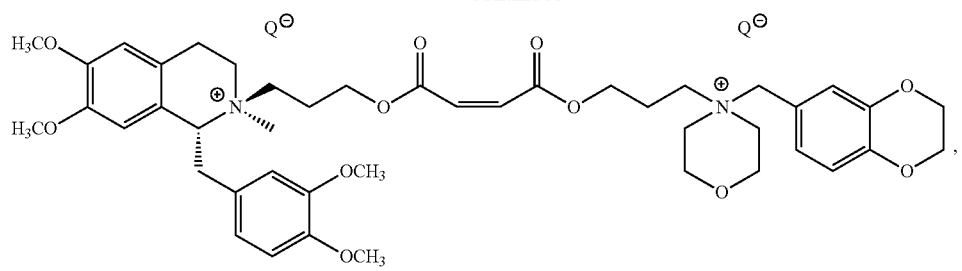
(1521-78, 1566-14)
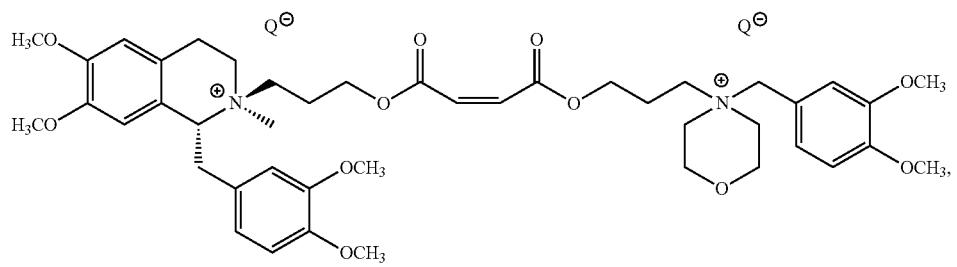
(1521-34, 1521-54)
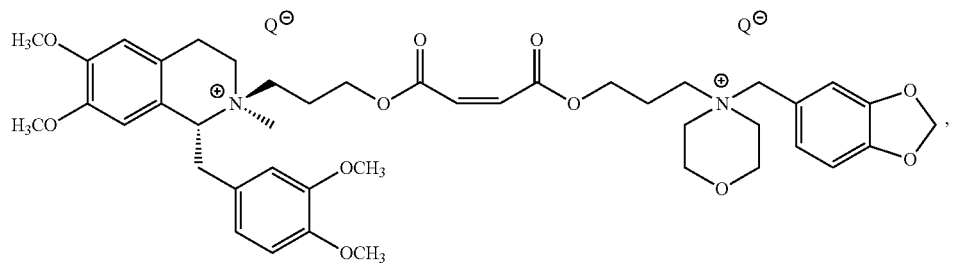
(1521-08, 1521-20, 1521-57)
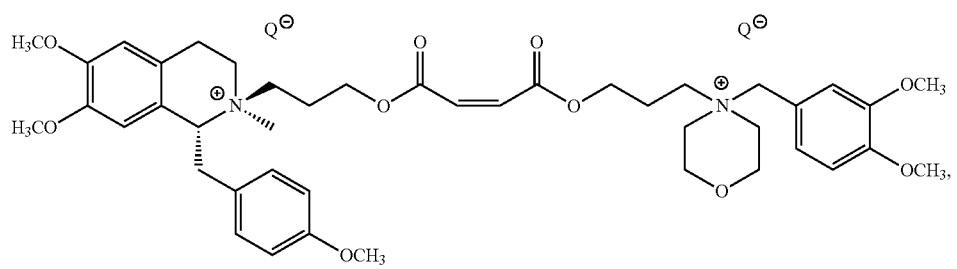
(1726-01, 1759-50)
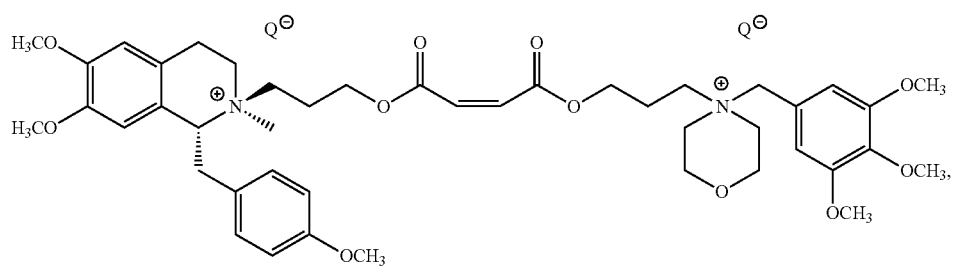
(1759-58)

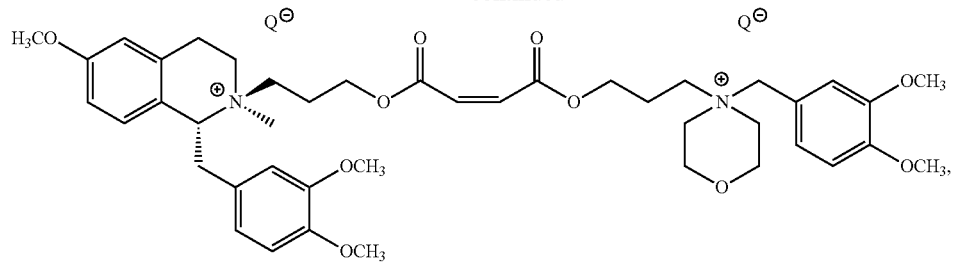
(1759-85)
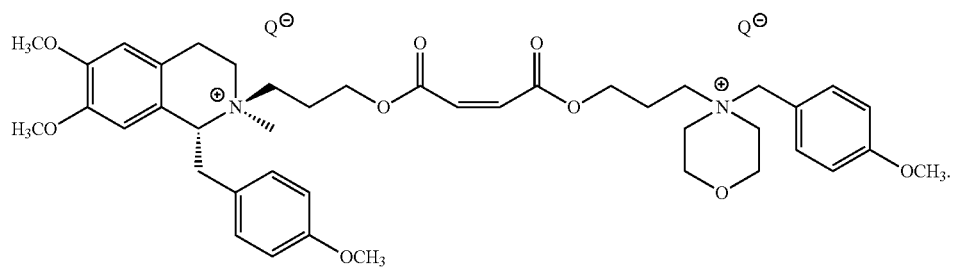
(1625-05)
Pyrrolidinium maleates
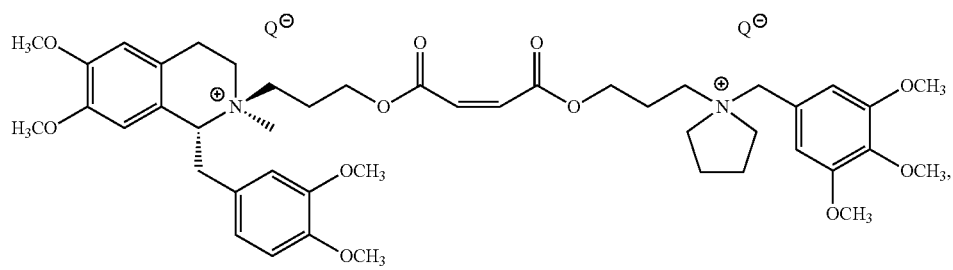
(1343-13, 1343-47)
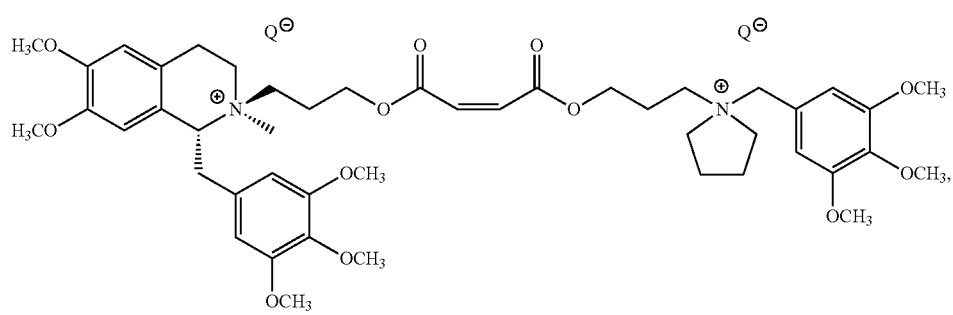
(1343-29)
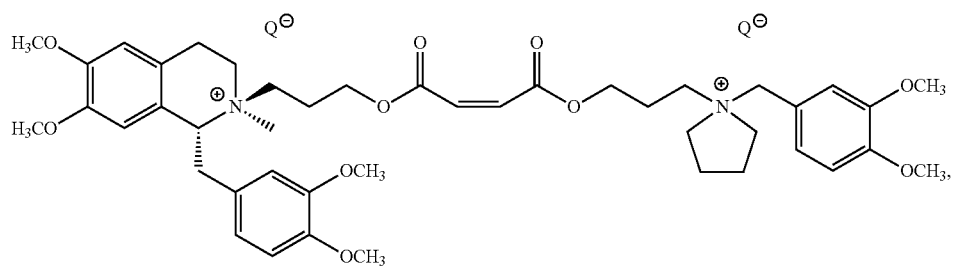
(1390-80)

-continued
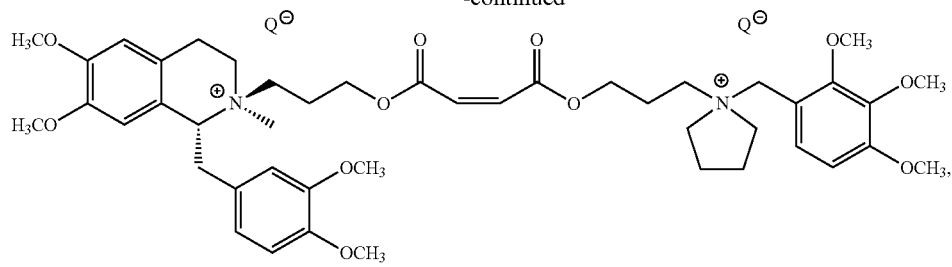
(1449-35)
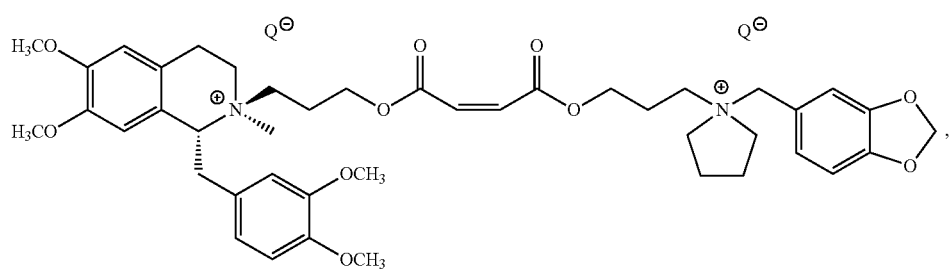
(1449-68)
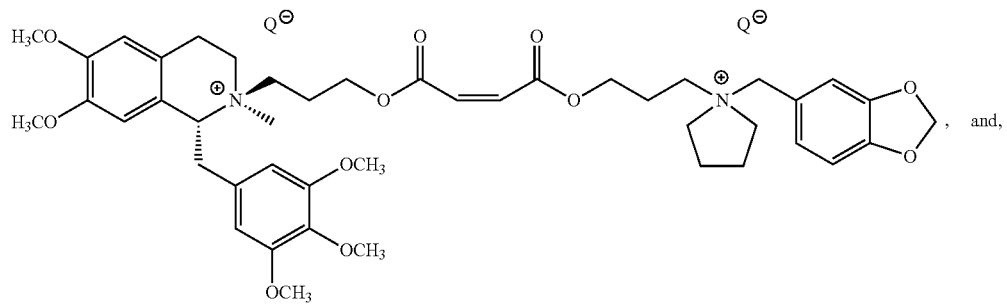
, and,
(1449-81)
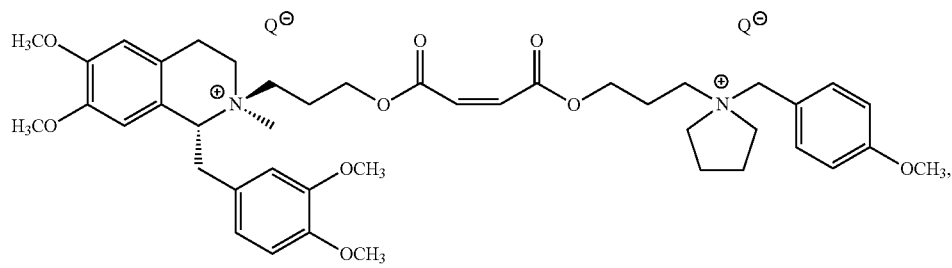
(1521-28)

wherein each $Q^{\ominus}$ is an independently selected pharmaceutically acceptable anion, e.g., chloride. The index numbers associated with each structure are batch numbers; i.e., a single chemical structure can have multiple synonymous batch numbers.

A maleate ester with particularly favorable biological properties, comprising a neuromuscular blocking agent of formula

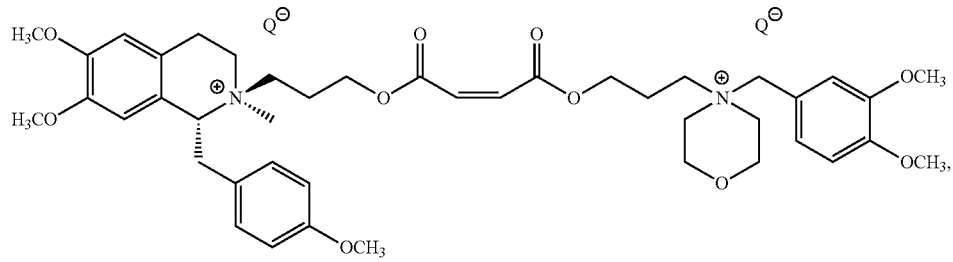

(1726-01, 1759-50)

wherein each $Q^{\ominus}$ is an independently selected pharmaceutically acceptable anion, e.g., chloride, is provided, and is discussed in greater detail below.

The invention provides, in various embodiments, a chlorofumarate ester, i.e., when the $R^1$ and $R^2$ groups are disposed in a trans configuration, and, in an embodiment, $R^1$ is chloro and $R^2$ is hydrogen. It is apparent that an isomeric series of chlorofumarates, wherein $R^1$ is hydrogen and $R^2$ is chloro, is also provided, which can have the same substitution patterns as for the exemplary chlorofumarate esters.

Chlorofumarates: Morpholinium 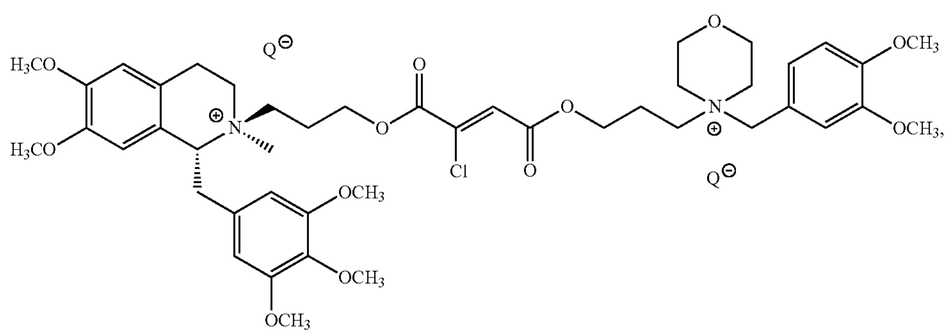 (1566-01)

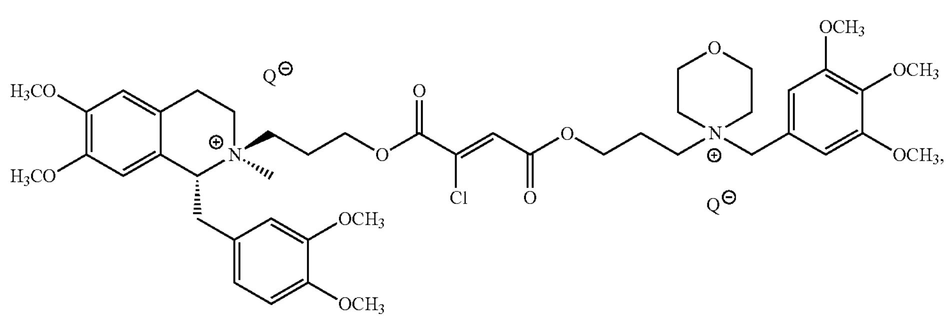

(1566-22)

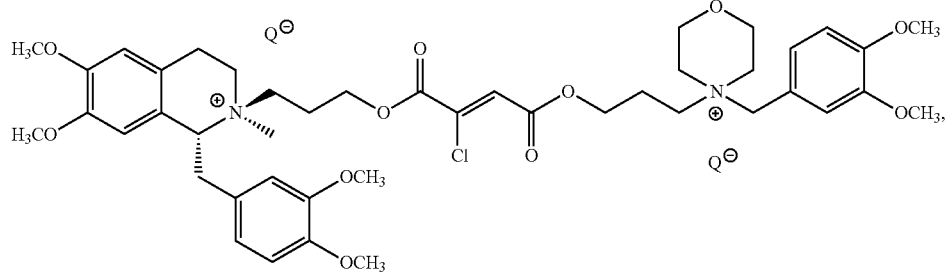
(1521-74)
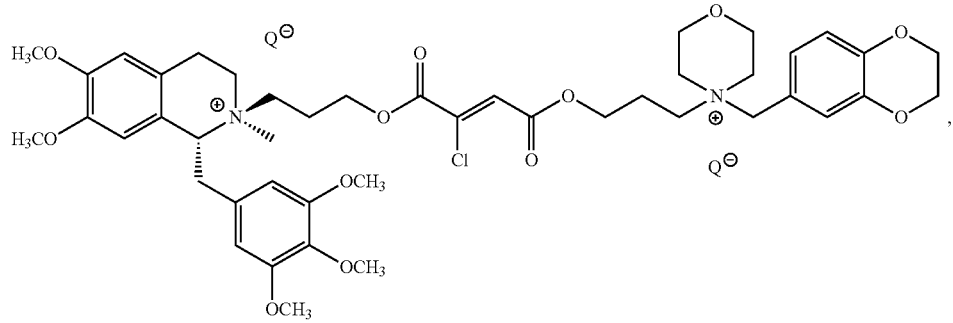
(1598-46)
Chlorofumarates: Pyrrolidinium
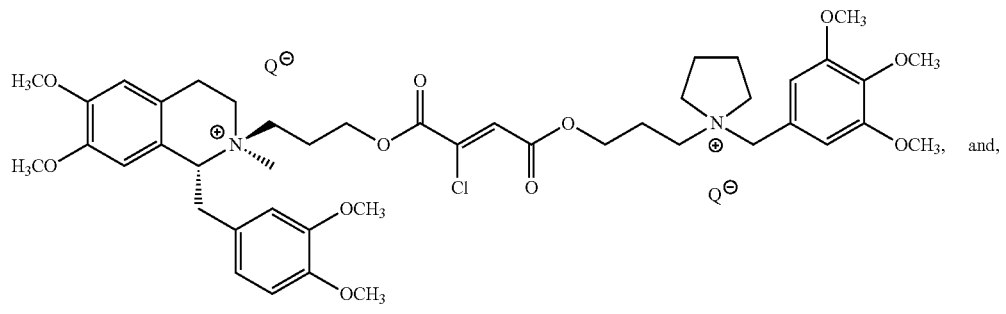
and,
(1326-72)
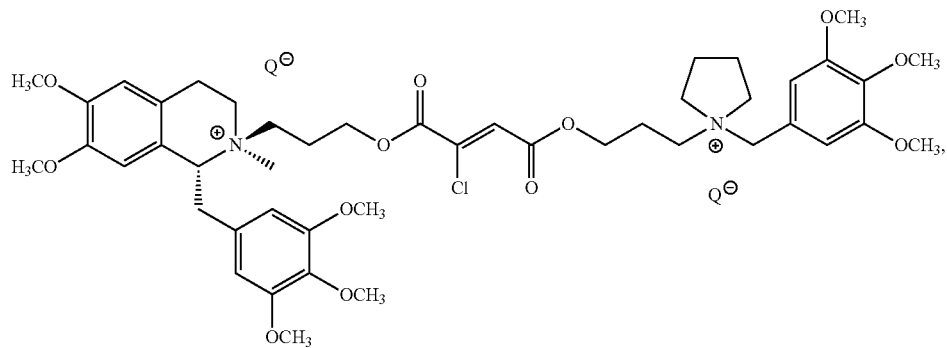
(1326-69)

wherein each $Q^{\ominus}$ is an independently selected pharmaceutically acceptable anion, e.g., chloride. Again, the associated identifiers are batch numbers, and one structure can have multiple synonymous batch numbers assigned as identifiers.

Chlorofumarates: Piperidinium

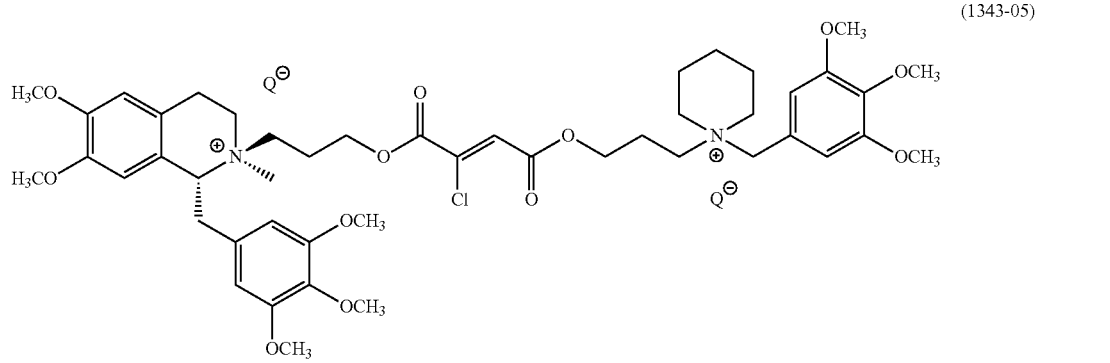

(1343-05)

Thus, in various embodiments, the invention provides an NMBA compound wherein the compound produces, upon administration of an effective amount of the compound to a patient, a neuromuscular blockade. As discussed further below, the effective amount of the NMBA can be about 0.01-10 mg per kg patient bodyweight, or can be about 0.1-1 mg per kg patient bodyweight.

Furthermore, the invention provides, in various embodiments, a NMBA compound of the invention wherein the neuromuscular blockage is reversible by administration to the patient of an effective amount of a thiol compound; e.g., wherein the thiol compound is L-cysteine or a pharmaceutically acceptable salt thereof, D-cysteine or a pharmaceutically acceptable salt thereof, or glutathione or a pharmaceutically acceptable salt thereof.

Methods of Synthesis

The compounds of the invention, across the scope of the claims, can be prepared by the person of ordinary skill using the procedures disclosed below in conjunction with the ordinary knowledge of a synthetic organic chemist. As the compounds of the invention are asymmetric around the central unsaturated diester moiety, i.e., maleate, fumarate, and the like, the compounds of the invention are readily prepared in a stepwise manner, coupling the isoquinolinium quaternary moiety and the second quaternary moiety bearing the cyclic morpholinium, piperidinium, piperazinium, or pyrrolidinium quaternary ring in separate steps to the unsaturated diacid to yield the product asymmetric bis-quaternary diester compounds of the invention.

Reference is also made to the PCT/US2010/000796 application by an inventor herein, published as WO2010/107488, which is incorporated herein by reference in its entirety; see, for example, pages 47-55 wherein the methods of preparation of many related intermediates are disclosed.

The following abbreviations are used throughout this document.
ACN Acetonitrile
DCE Dichloroethane
DCM Dichloromethane
DI Deionized
DIPEA, $^{i}Pr_2EtN$ N,N-Diisopropylethylamine
DMF N,N-Dimethylformamide
DMSO Dimethylsulfoxide
eq Equivalents
$Et_2O$ Diethyl ether
EtOAc Ethyl acetate
h Hours
HCl Hydrochloric acid
LiHDMS Lithium hexamethyldisilazide
mg Milligrams
min Minutes
mL Milliliters
μL Microliters
mmole Millimoles
MS Mass spectroscopy
MeOH Methanol
MTBE Methyl tert-butyl ether
NMM N-Methylmorpholine
RT, rt Room temperature
sat. Saturated
TFA Trifluoroacetic acid
THF Tetrahydrofuran
~ to (range, e.g., X~Y=X to Y)
Precursors The PCT/US2010/000796 application, by an inventor herein, published as WO2010/107488, pages 47-55, describes methods of preparation for the "left-side" first quaternary moiety (isoquinolinium) precursors, and the below procedures describe method of preparation of reagents for the "right side" (morpholinium, pyrrolidinium, etc.) second quaternary moiety.

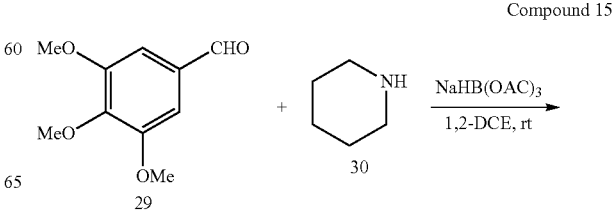

Compound 15

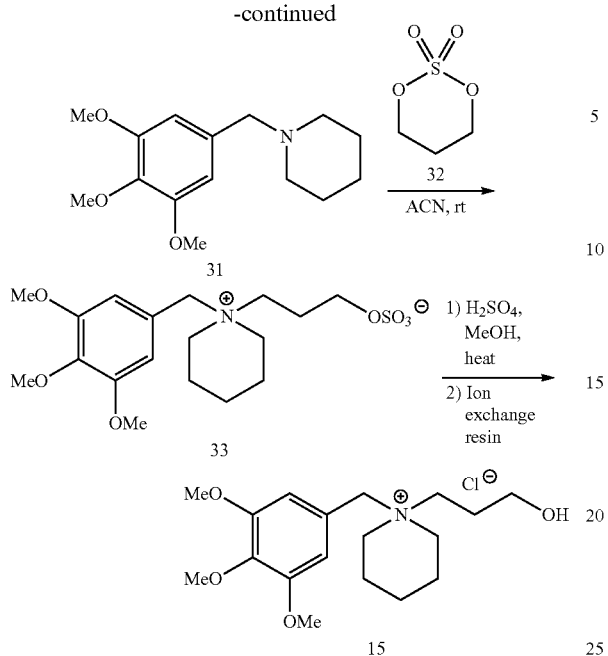

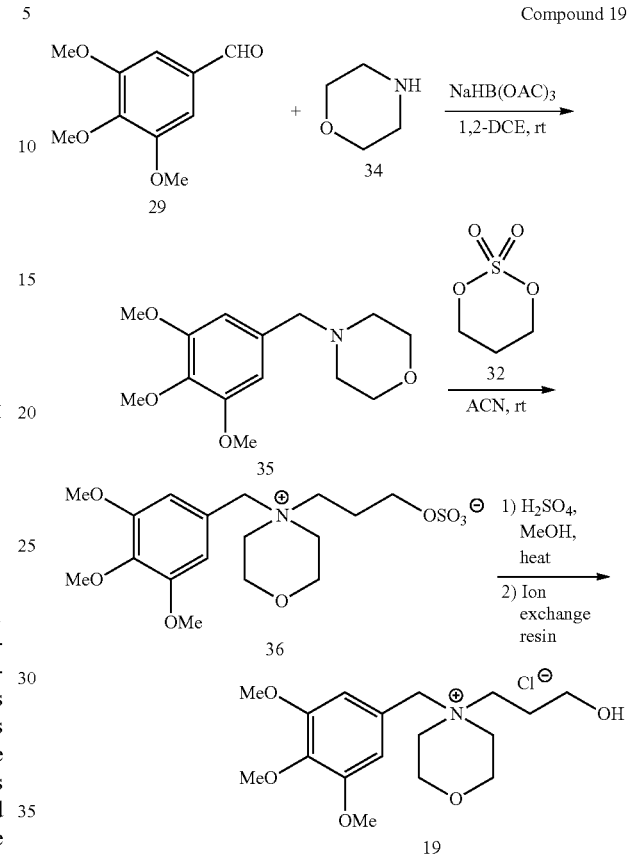

A solution of 29 (4.0 g, 0.020 mol) and 30 (3.0 mL, 0.031 mol) in 1,2-DCE (50 mL) was charged with sodium triacetoxyborohydride (5.0 g, 0.022 mol) in portions over 3 minutes at room temperature and the hazy yellow mixture was stirred for 5 hours. The solution was charged with aqueous NaOH to reach an aqueous pH≥10 on phase separation. The organics were washed with a brine solution and solvent was removed in vacuo. The resulting yellow liquid was dissolved in 1,2-DCE and was extracted with 1M aqueous HCl. The acidic aqueous product solution was washed with 1,2-DCE. The pH of the aqueous solution was adjusted to ≥10 using aqueous NaOH in the presence of 1,2-DCE. The basic aqueous was further extracted with 1,2-DCE. The combined organics were dried over $Na_2SO_4$, filtered and stripped of solvent in vacuo to give 31 [4.3 g, 80% yield] as a light yellow liquid.

A stirring solution of 31 (4.3 g, 0.016 mol) in ACN (20 mL) was charged with 32 (4.5 g, 0.032 mol) in one portion at room temperature. The clear light yellow solution was heated to 45±5° C. for 19 hours. The hazy solution was cooled to room temperature and solvent was removed in vacuo. The resulting oil was dissolved in ACN (12 mL) at room temperature and was stirred for 1 hour to give a thick off-white slurry. The slurry was charged with MTBE (60 mL) and was further stirred 2 hours. Vacuum filtration gave an off-white solid that was washed with MTBE and dried overnight under vacuum at room temperature to give 33 [6.9 g, 106% yield, isolated solid not analyzed for MTBE content] as an off-white solid.

A hazy yellow solution of 33 (6.5 g, 0.016 mol) in MeOH (65 mL) was charged with $H_2SO_4$ (0.069 mL, 0.0013 mol) and was heated to 55±5° C. for 17 hours. The clear yellow solution was cooled to room temperature and was passed through a MeOH washed plug of Dowex 1X8-100 resin (26 g) four times by gravity elution. The resin was washed forward with MeOH. The product containing eluates were stripped of solvent in vacuo and solvent was exchanged for 1,2-DCE through multiple distillation cycles to remove MeOH and give a white slurry. The slurry was subjected to vacuum filtration to give off-white solids that were washed with 1,2-DCE. The solids were dried in a vacuum oven at 35±5° C. to give 15 [3.9 g, 67% yield] as a white to off-white solid.

Compound 35 [3.7 g, 90% yield] was isolated as a light yellow oil starting with 29 (3.0 g, 0.015 mol), 34 (2.0 mL, 0.023 mol) and sodium triacetoxyborohydride (6.8 g, 0.031 mol) in 1,2-DCE (50 mL) according to the general procedure used to prepare compound 31.

A clear light yellow solution of 35 (3.7 g, 0.014 mol) and 32 (3.8 g, 0.028 mol) in ACN (25 mL) was heated to 40±5° C. for 49 hours prior to cooling to room temperature. The resulting white mixture was subjected to vacuum filtration to give a white solid that was washed with MTBE. The solids were dried under vacuum at room temperature to give 36 [4.9 g, 88% yield] as a white solid.

Compound 19 [1.5 g, 47% yield] was isolated as an off-white solid starting with 36 (4.9 g, 0.012 mol) and $H_2SO_4$ (0.051 mL, 0.00096 mol) in MeOH (50 mL) and using Dowex 1X8-100 resin (20 g) according to the general procedure used to prepare compound 15.

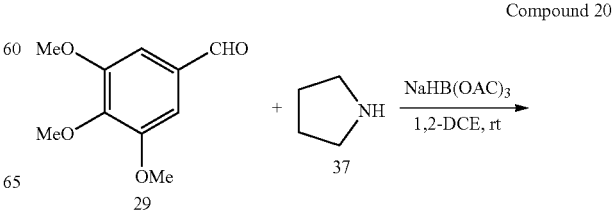

-continued

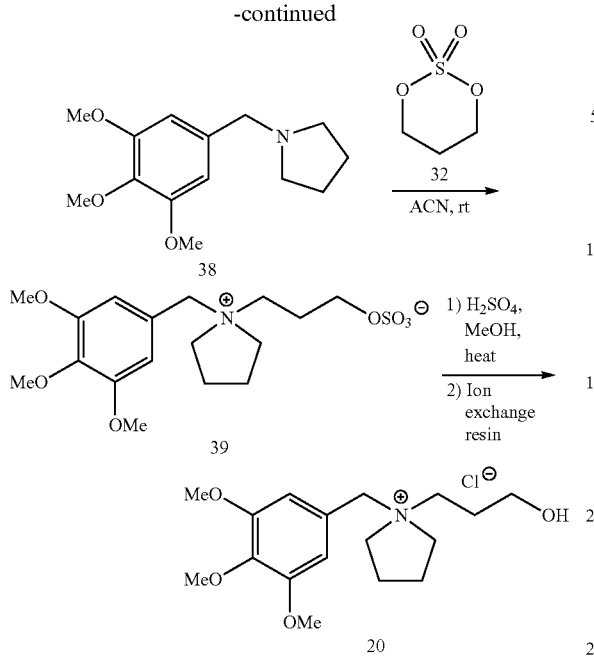

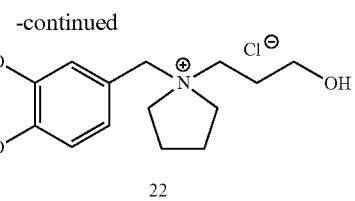

Compound 41 [6.0 g, 91% yield] was isolated as an orange oil starting with 40 (5.0 g, 0.030 mol), 37 (3.8 mL, 0.045 mol) and sodium triacetoxyborohydride (7.0 g, 0.033 mol) in 1,2-DCE (60 mL) according to the general procedure used to prepare compound 31.

Compound 42 [8.8 g, 90% yield] was isolated as an pale yellow solid starting with 41 (6.0 g, 0.027 mol) and 32 (8.2 g, 0.060 mol) in ACN (18 mL) according to the general procedure used to prepare compound 33.

Compound 22 [6.9 g, 89% yield] was isolated as an pale yellow solid starting with 42 (8.8 g, 0.025 mol) and H₂SO₄ (0.10 mL, 0.0020 mol) in MeOH (88 mL) and using Dowex 1X8-100 resin (35 g) according to the general procedure used to prepare compound 20.

Compound 38 [5.1 g, quant. yield] was isolated as a red oil starting with 29 (4.0 g, 0.020 mol), 37 (2.5 mL, 0.031 mol) and sodium triacetoxyborohydride (5.0 g, 0.022 mol) in 1,2-DCE (50 mL) according to the general procedure used to prepare compound 31.

Compound 39 [8.9 g, 112% yield, isolated foam not analyzed for MTBE content] was isolated as a light orange foam starting with 38 (5.1 g, 0.020 mol) and 32 (5.6 g, 0.041 mol) in ACN (15 mL) according to the general procedure used to prepare compound 33.

Compound 20 [5.4 g, 77% yield] was isolated as a white solid starting with 39 (7.9 g, 0.020 mol) and H₂SO₄ (0.087 mL, 0.0016 mol) in MeOH (56 mL) and using Dowex 1X8-100 resin (32 g) according to the general procedure used to prepare compound 20.

Compound 23

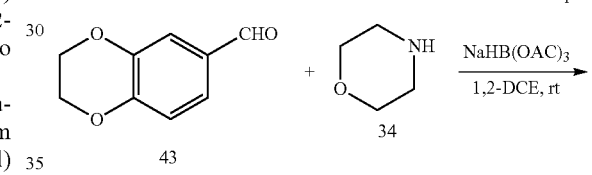

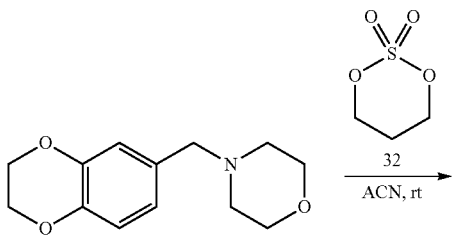

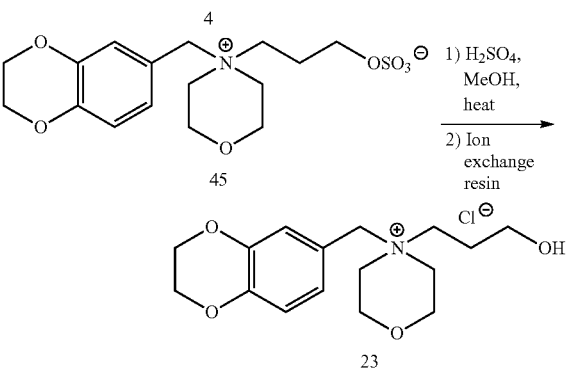

Compound 22

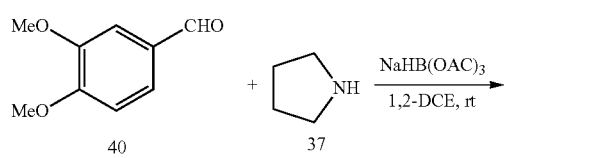

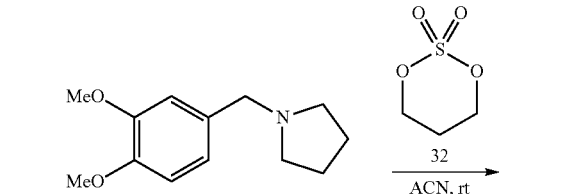

Compound 44 [4.0 g, 92% yield] was isolated as a pale yellow oil starting with 43 (3.0 g, 0.018 mol), 34 (2.4 mL, 0.027 mol) and sodium triacetoxyborohydride (8.2 g, 0.037 mol) in 1,2-DCE (50 mL) according to the general procedure used to prepare compound 31.

Compound 45 [5.7 g, 91% yield] was isolated as an off-white solid starting with 44 (4.0 g, 0.017 mol) and 32 (4.7 g, 0.034 mol) in ACN (16 mL) according to the general procedure used to prepare compound 36.

Compound 23 [4.2 g, 82% yield] was isolated as a white solid starting with 45 (5.7 g, 0.015 mol) and $H_2SO_4$ (0.065 mL, 0.0012 mol) in MeOH (57 mL) and using Dowex 1X8-100 resin (23 g) according to the general procedure used to prepare compound 20.

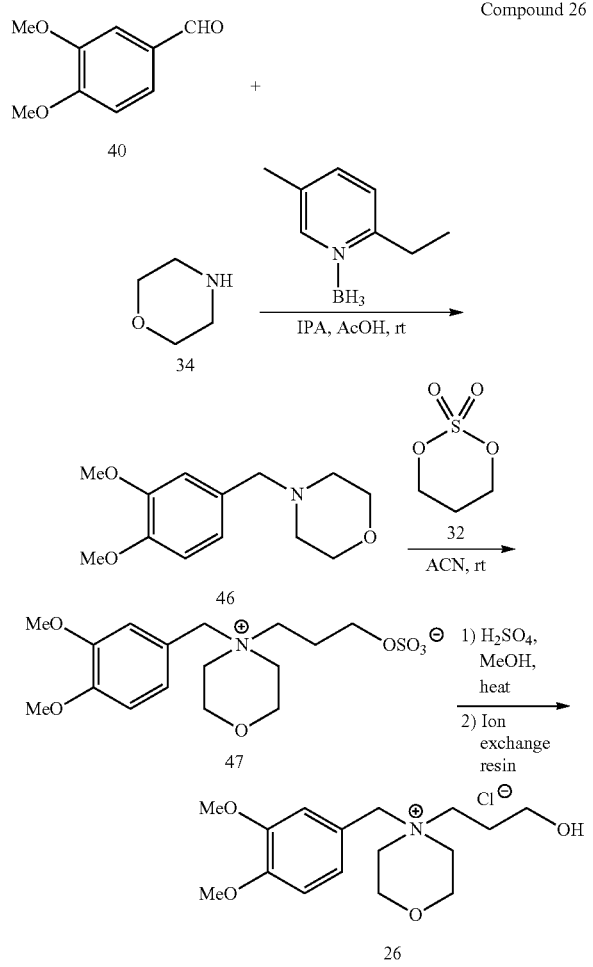

Compound 26

A stirring orange mixture of 40 (7.0 g, 0.042 mol), 34 (3.8 mL, 0.043 mol) and IPA (40 mL) was cooled to 10-15° C. and was charged with glacial acetic acid (4.9 mL, 0.086 mol) followed by 5-ethyl-2-methylpyridine borane complex (3.6 mL, 0.024 mol) to give a clear golden solution that was stirred 24 hours at room temperature. The clear golden solution was charged with dry HCl in IPA to quench the excess borane reagent. Stirring 25 minutes at room temperature followed by in vacuo solvent removal gave a yellow oil that was stirred with a mixture of aqueous HCl and DCM. The aqueous product phase was washed with DCM and was then adjusted to an aqueous pH≥10 using aqueous NaOH in the presence of DCM. The basic aqueous was further extracted with DCM. The combined organic phases were washed with brine, dried over $Na_2SO_4$ and were subjected to vacuum filtration. Solvent removal in vacuo gave 46 [11.0 g, 110% yield, product not analyzed for boron salt content] as a clear essentially colorless liquid.

Compound 47 [7.7 g, 81% yield] was isolated as an off-white solid starting with 46 (6.0 g, 0.025 mol) and 32 (6.3 g, 0.046 mol) in ACN (48 mL) according to the general procedure used to prepare compound 33.

A stirring slurry of 47 (7.6 g, 0.020 mol) in MeOH (76 mL) was charged with $H_2SO_4$ (0.086 mL, 0.0016 mol) and was heated to 55±5° C. for 20 h. The clear yellow solution was cooled to room temperature and was passed through a MeOH washed plug of Dowex 1X8-100 resin (30 g) four times by gravity elution. The resin was washed forward with MeOH. The product containing eluates were stripped of solvent in vacuo and solvent was exchanged for a mixture of 1,2-DCE and ACN through multiple distillation cycles to remove MeOH and give a white mixture. The mixture was subjected to vacuum filtration and the off-white solids were washed with 1,2-DCE. The solids were dried in a vacuum oven at room temperature to give 26 [5.2 g, 77% yield] as a white to off-white solid.

Chlorofumarates:
Morpholinium

The syntheses of the below-listed compounds are representative of the methods of preparation of fumarates such as chlorofumarates, and are presented below. Analogous methods for preparation of other fumarates and chlorofumarates based on the procedure can be adapted by the person of ordinary skill using selection of reagents and routine optimization to prepare other members of the fumarate/chlorofumarate series of NMBA compounds of the invention.

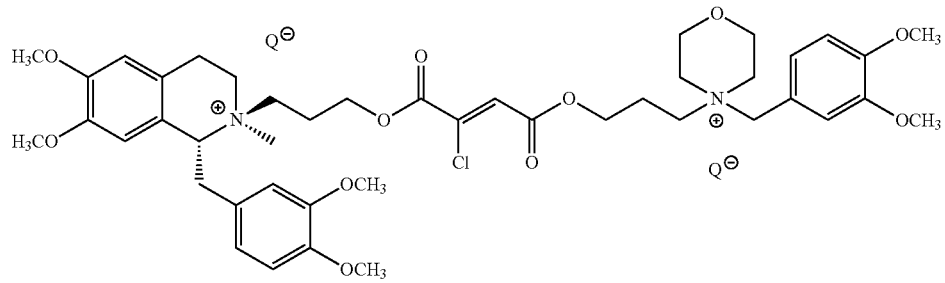

-continued
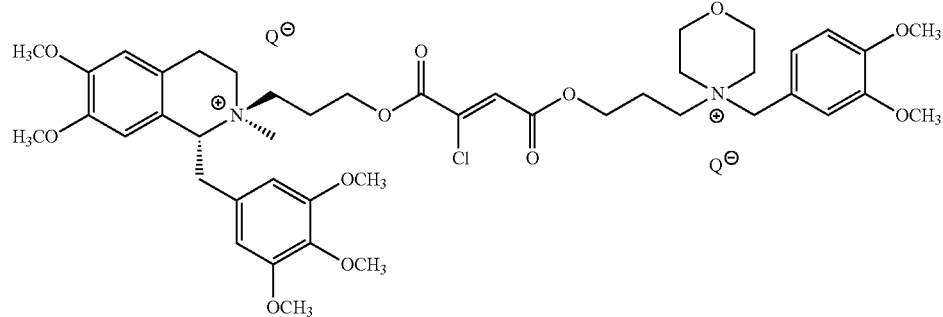
1566-01
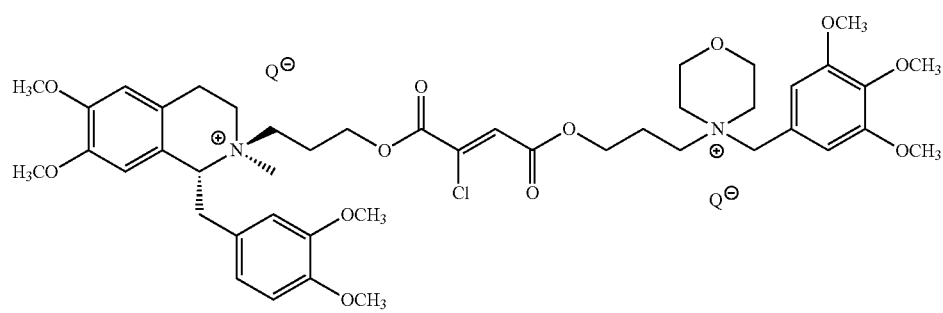
1566-22
Synthesis of 1566-22
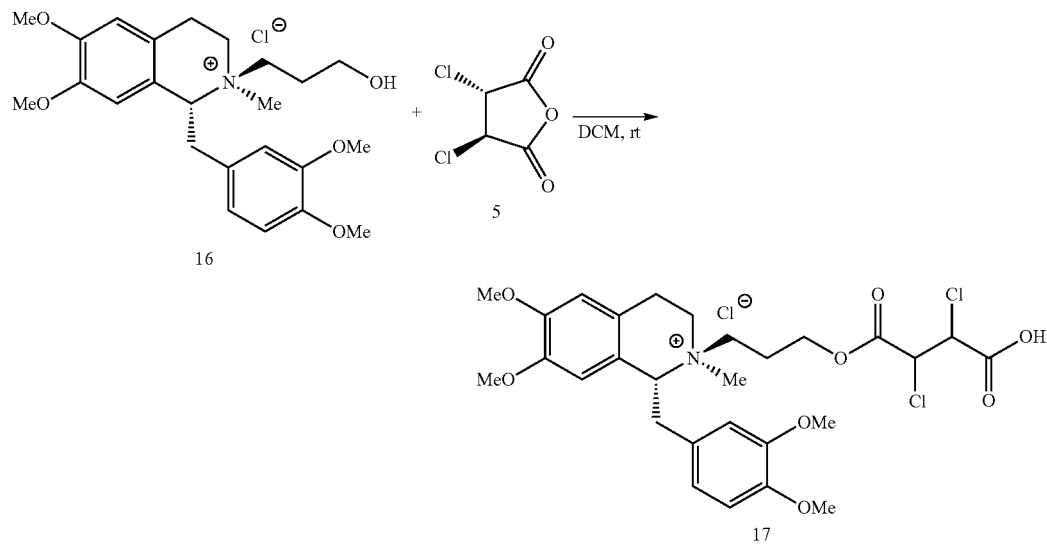
17 →(Et₃N / ACN, 0-5° C.)

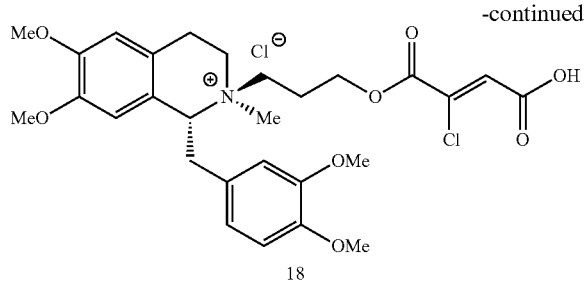

18

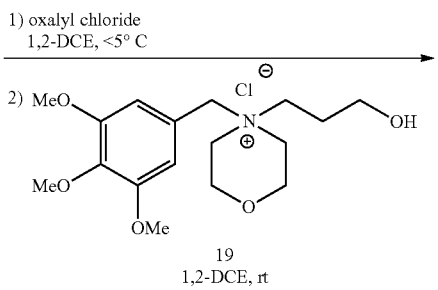

19
1,2-DCE, rt

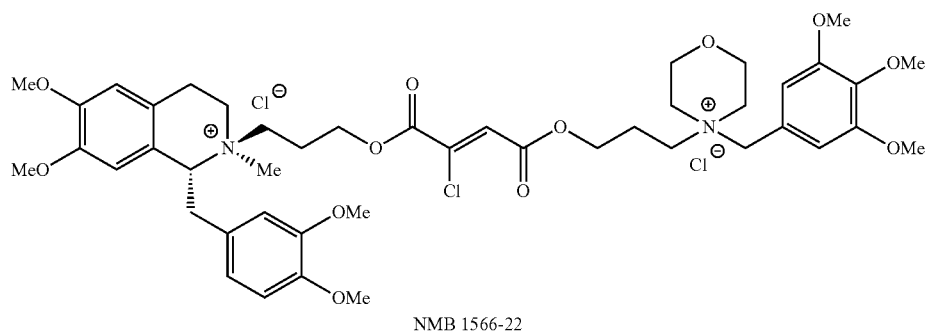

NMB 1566-22

To a solution of 16 (4.0 g, 0.0089 mol) in 1,2-DCE (60 mL) at ambient temperature (rt) was charged 1,3-dichlorosuccinic anhydride (3.9 g, 0.023 mol). The solution was stirred for 22 hours at rt under $N_2$. The reaction mixture was diluted with DCM (40 mL) and ACN (35 mL) to provide a clear yellow solution that was added to stirring MTBE (800 mL) over 40 minutes to give a product slurry. Compound 17 was isolated as an off-white solid [5.5 g, 99% yield] after vacuum filtration followed by washing with MTBE and drying for 16 hours at rt under vacuum.

To a solution of 17 (5.5 g, 0.088 mol) in ACN (49 mL) was added triethylamine (3.1 mL, 0.022 mol) over 6 minutes at 0±5° C. The resulting yellow-orange slurry was stirred at 0±5° C. for 3 hours. Vacuum filtration gave a clear light yellow solution that was subjected to in vacuo solvent removal at rt to give a yellow foam. The foam was dissolved in DCM and was extracted with DI water. The pH of the aqueous phase was adjusted to ≤2 using 1M aqueous HCl and was extracted with 4:1 DCM:ACN in the presence of NaCl (24 wt % aqueous solution). The combined organic extracts were subjected to in vacuo solvent removal at rt to give a yellow oil. The oil was dissolved in DCM (1 volume) and was added to stirring MTBE (10 volumes) at rt over 25 minutes. The slurry was stirred >1 hour at rt and compound 18 was isolated as an off-white solid [4.6 g, 89% yield] after vacuum filtration, washing with MTBE and drying for 16 hours at rt under vacuum.

To a solution of 18 (1.5 g, 0.0026 mol) in anhydrous 1,2-DCE (70 mL) was added oxalyl chloride (1.1 mL, 0.013 mol) at 0±5° C. over 6 minutes under $N_2$. The bright yellow solution was stirred at 0±5° C. for 2 hours. The solution was subjected to in vacuo solvent removal at rt to provide a yellow oil. The oil was subjected to two additional in vacuo solvent distillation cycles at rt using dry 1,2-DCE. The oil was dissolved in dry 1,2-DCE (10 mL) and was added to a stirring slurry of compound 19 (0.91 g, 0.0025 mol) and 4 Å molecular sieve powder (0.8 g) in mixture of dry 1,2-DCE (45 mL) and ACN (20 mL) over 5 minutes at rt. The pale yellow slurry was stirred 17 hours at rt and was subjected to vacuum filtration and in vacuo solvent removal at rt to give a dark yellow foam. The foam was dissolved in 1,2-DCE and was extracted with DI water. The aqueous product solution was charged with NaCl (27 wt % aqueous solution) and was extracted with 5:1 $CHCl_3$:ACN. The $CHCl_3$/ACN product solution was washed with 12:1 brine:10% aqueous $KHCO_3$ and 24% aqueous NaCl. The aqueous wash phases were back-extracted with 5:1 $CHCl_3$:ACN and the back-extraction phases were combined with the product solution and were dried over $Na_2SO_4$. Vacuum filtration and in vacuo solvent removal at rt gave a dark yellow foam that was dissolved in DI water. The aqueous solution was stirred with activated carbon (400 mg) and was filtered. The carbon residue was washed forward with DI water. The aqueous product solution was lyophilized to give NMB 1566-22 [1.4 g, 58% yield] as an off-white solid.

Chlorofumarates: Piperidinium
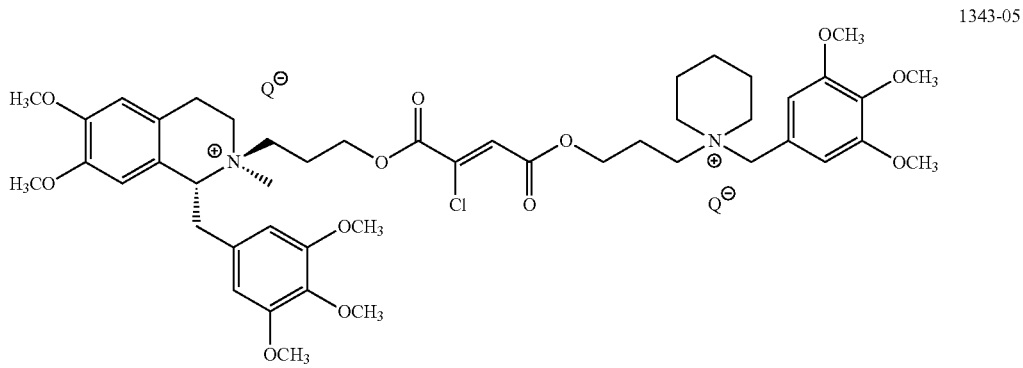
1343-05
Synthesis
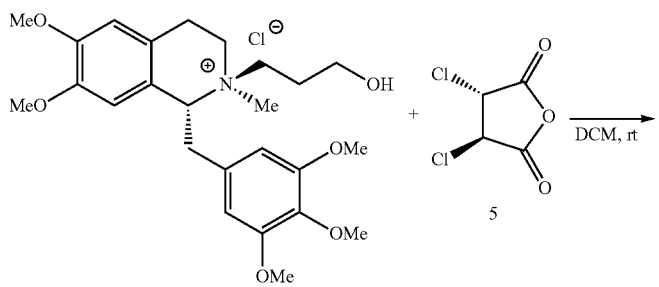
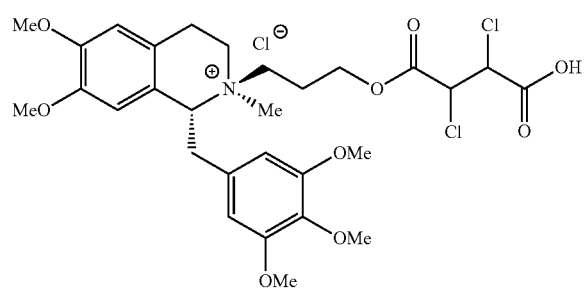
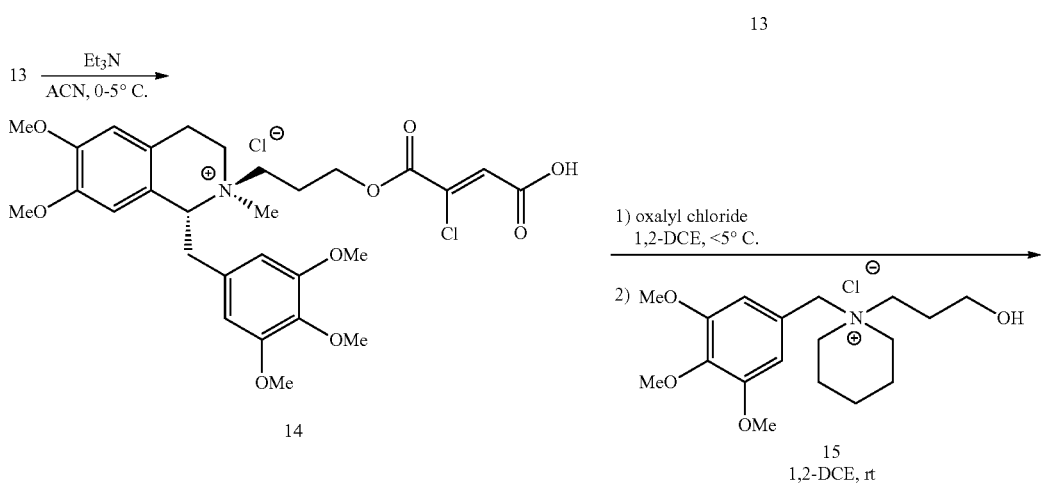

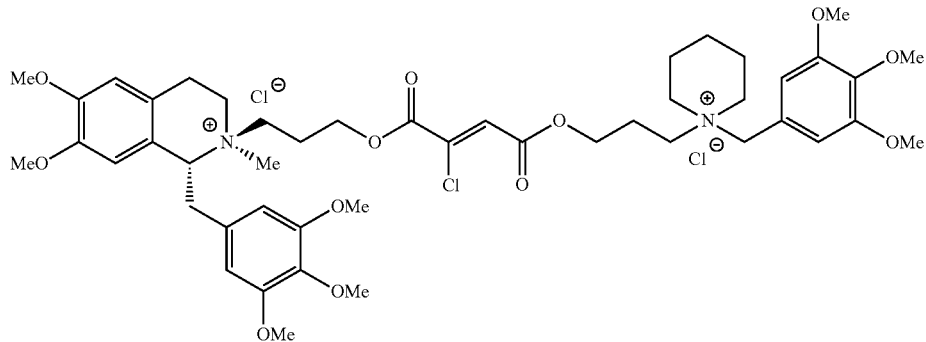

To a solution of 12 (6.0 g, 0.012 mol) in 1,2-DCE (60 mL) and ACN (20 mL) at room temperature (rt) was charged 1,3-dichlorosuccinic anhydride (5.7 g, 0.034 mol). The solution was stirred for 7 hours at rt under $N_2$. The reaction solution was added to stirring MTBE (9 volumes) over 30 minutes to give a product slurry. Compound 13 was isolated as an off-white solid [7.8 g, quantitative yield] after vacuum filtration followed by washing with MTBE and drying for 16 hours at rt under vacuum.

To a solution of 13 (7.8 g, 0.012 mol) in ACN (85 mL) was added triethylamine (5.0 mL, 0.036 mol) over 10 minutes at 0±5° C. The resulting light red slurry was stirred at 0±5° C. for 1.5 hours. Vacuum filtration gave a clear dark pink solution that was subjected to in vacuo solvent removal at rt to give a red oil. The oil was dissolved in DCM and was extracted with DI water. The pH of the aqueous phase was adjusted to ≤2 using 1M aqueous HCl and was extracted with 4:1 DCM:ACN in the presence of NaCl (24 wt % aqueous solution). The combined organic extracts were subjected to in vacuo solvent removal at rt to give a yellow foam. The foam was dissolved in DCM (1 volume) and was added to stirring MTBE (12 volumes) at rt over 25 minutes. The slurry was stirred >1 hour at rt and compound 14 was isolated as an off-white solid [6.6 g, 90% yield] after vacuum filtration, washing with MTBE and drying for 18 hours at rt under vacuum.

To a solution of 14 (0.8 g, 0.0013 mol) in anhydrous 1,2-DCE (25 mL) was added oxalyl chloride (0.6 mL, 0.0065 mol) at 0±5° C. over 5 minutes under $N_2$. The bright yellow solution was stirred at 0±5° C. for 1 hour and was allowed to warm to rt over 2 hours. The solution was subjected to in vacuo solvent removal at rt to provide a yellow oil. The oil was subjected to two additional in vacuo solvent distillation cycles at rt using dry 1,2-DCE. The oil was dissolved in dry 1,2-DCE (10 mL) and was added to a stirring slurry of compound 15 (0.45 g, 0.0012 mol) and 4 Å molecular sieve powder (0.3 g) in dry 1,2-DCE (15 mL) over 5 minutes at rt. The pale yellow slurry was stirred 15 hours at rt and was subjected to vacuum filtration and was extracted with DI water. The aqueous product solution was charged with NaCl (24 wt % aqueous solution) and was extracted with $CHCl_3$. The $CHCl_3$ product solution was washed with 12:1 brine:10% aqueous $KHCO_3$, 24% aqueous NaCl and was dried over $Na_2SO_4$. Vacuum filtration and in vacuo solvent removal at rt gave a light yellow foam that was dissolved in DI water. The aqueous solution was stirred with activated carbon (260 mg) and was filtered. The carbon residue was washed forward with DI water. The aqueous product solution was lyophilized to give NMB 1343-05 [0.74 g, 62% yield] as an off-white solid.

Chlorofumarates: Pyrrolidinium

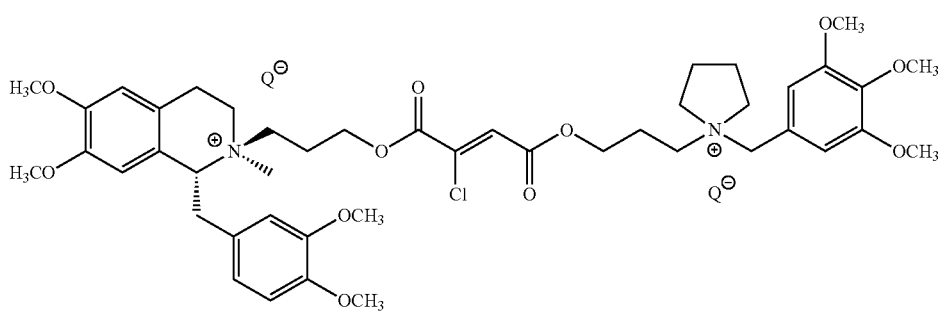

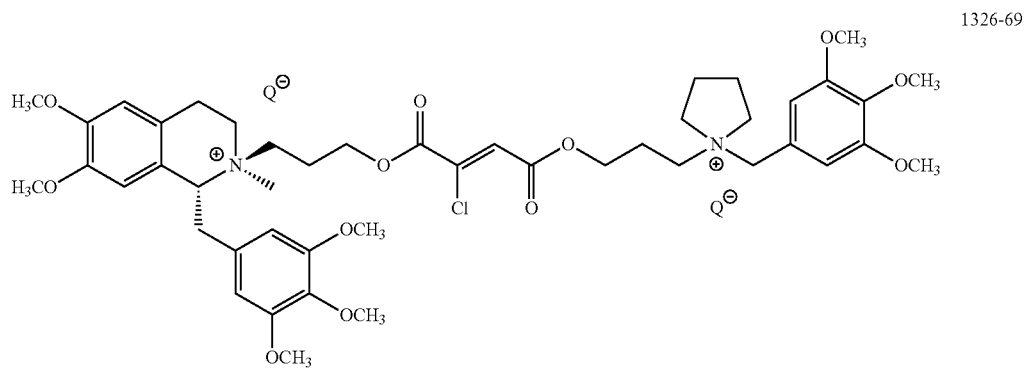
1326-69
Synthesis of 1326-69
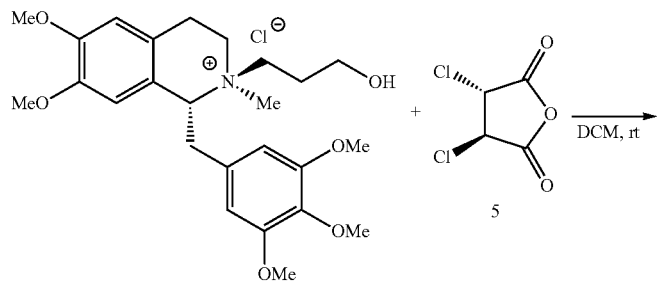
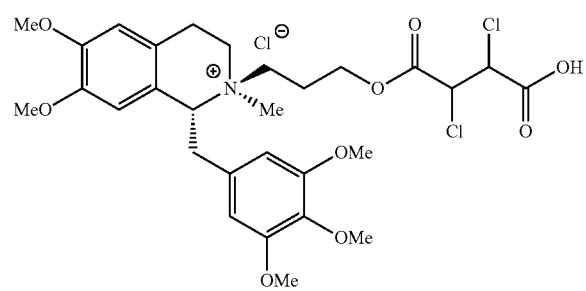
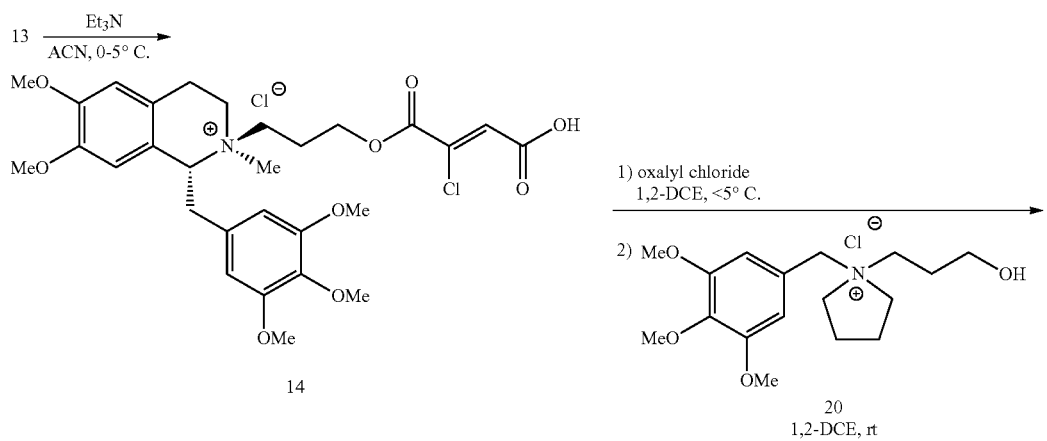

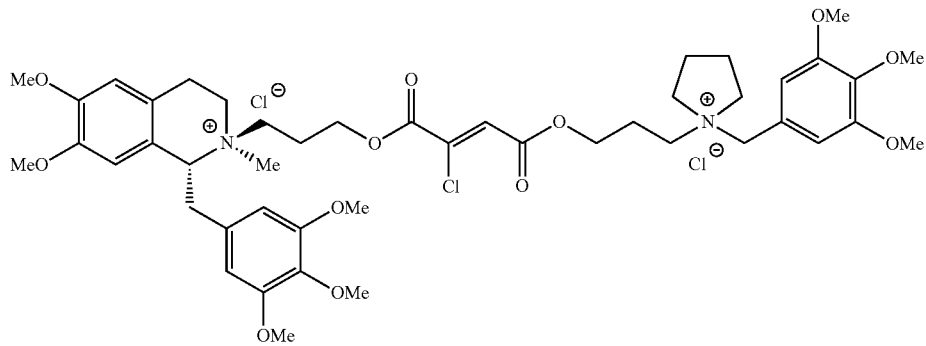

NMB 1326-69

To a solution of 12 (6.0 g, 0.012 mol) in 1,2-DCE (60 mL) at ambient temperature (rt) was charged 1,3-dichlorosuccinic anhydride (5.5 g, 0.034 mol). The solution was stirred for 22 hours at rt under $N_2$. The reaction mixture was diluted with DCM (1 volume) to provide a hazy solution that was added to stirring MTBE (12 volumes) over 30 minutes to give a product slurry. Compound 13 was isolated as an off-white solid [6.3 g, 78% yield] after vacuum filtration followed by washing with MTBE and drying for 16 hours at rt under vacuum.

To a solution of 13 (6.3 g, 0.0097 mol) in ACN (57 mL) was added triethylamine (3.4 mL, 0.024 mol) over 11 minutes at 0±5° C. The resulting light red slurry was stirred at 0±5° C. for 3 hours. Vacuum filtration gave a clear red solution that was subjected to in vacuo solvent removal at rt to give a red oil. The oil was dissolved in DCM and was extracted with DI water. The pH of the aqueous phase was adjusted to ≤2 using 1M aqueous HCl and was extracted with 5:1 DCM:ACN in the presence of NaCl (24 wt % aqueous solution). The combined organic extracts were subjected to in vacuo solvent removal at rt to give a yellow foam. The foam was dissolved in DCM (1 volume) and was added to stirring MTBE (10 volumes) at rt over 45 minutes. The slurry was stirred >1 hour at rt and compound 14 was isolated as an off-white solid [5.3 g, 89% yield] after vacuum filtration, washing with MTBE and drying for 17 hours at rt under vacuum.

To a solution of 14 (1.6 g, 0.0026 mol) in anhydrous 1,2-DCE (30 mL) was added oxalyl chloride (1.1 mL, 0.013 mol) at 0±5° C. over 5 minutes under $N_2$. The bright yellow solution was stirred at 0±5° C. for 3 hours. The solution was subjected to in vacuo solvent removal at rt to provide a yellow oil. The oil was subjected to two additional in vacuo solvent distillation cycles at rt using dry 1,2-DCE. The oil was dissolved in dry 1,2-DCE (10 mL) and was added to a stirring slurry of compound 20 (0.84 g, 0.0024 mol) and 4 Å molecular sieve powder (0.4 g) in dry 1,2-DCE (25 mL) over 8 minutes at rt. The pale yellow slurry was stirred 16 hours at rt and was subjected to vacuum filtration, dilution with DCM and extraction with DI water. The aqueous product solution was charged with NaCl (23 wt % aqueous solution) and was extracted with $CHCl_3$. The $CHCl_3$ product solution subjected to two cycles of aqueous washing using with 15:1 brine:10% aqueous $KHCO_3$ followed by 24% aqueous NaCl. Drying over $Na_2SO_4$ followed by vacuum filtration and in vacuo solvent removal at rt gave a light yellow foam that was dissolved in DI water. The aqueous solution was stirred with activated carbon (250 mg) and was filtered. The carbon residue was washed forward with DI water. The aqueous product solution was lyophilized to give NMB 1326-69 [1.3 g, 55% yield] as an off-white solid.

Maleates: Morpholinium

The syntheses presented below are representative of the methods of preparation of morpholinium maleates, is presented below. Analogous methods for preparation of other maleates based on the below procedure can be adapted by the person of ordinary skill using selection of reagents and routine optimization to prepare other members of the maleate series of NMBA compounds of the invention.

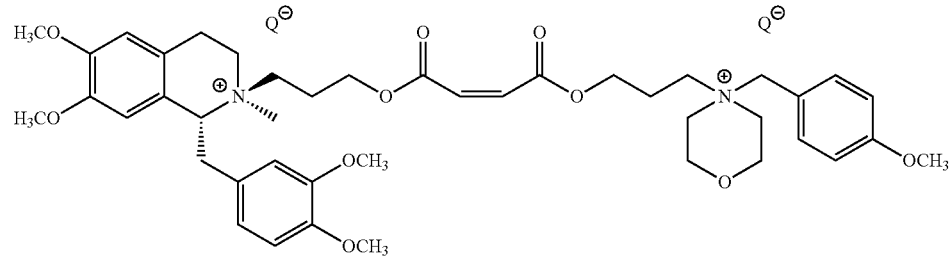

1521-83, 1566-07

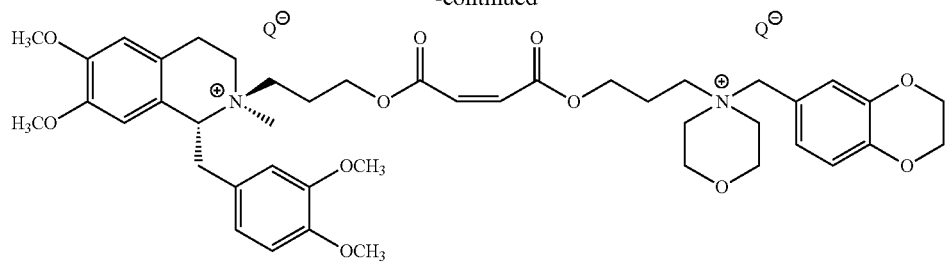
1521-78, 1566-14
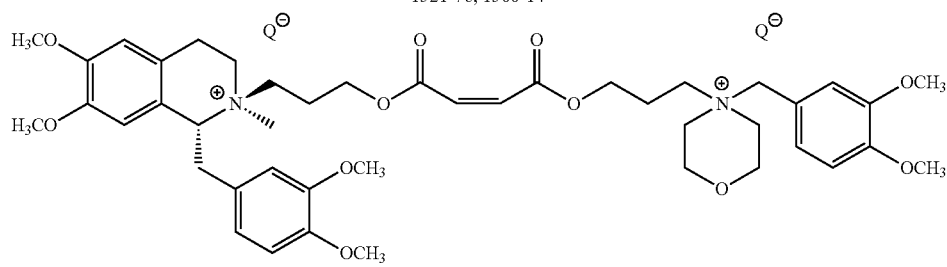
1521-34, 1521-54
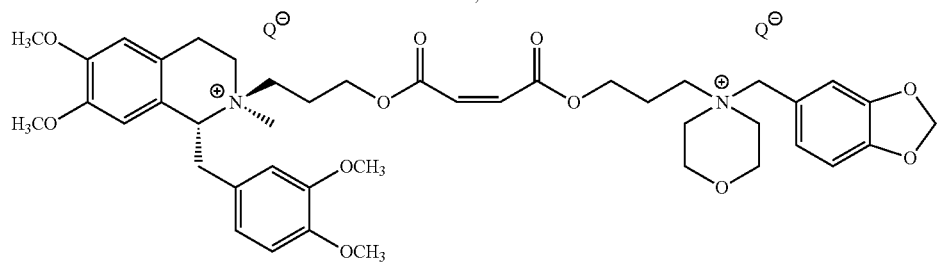
1521-08, 1521-57
Synthesis of 1521-78
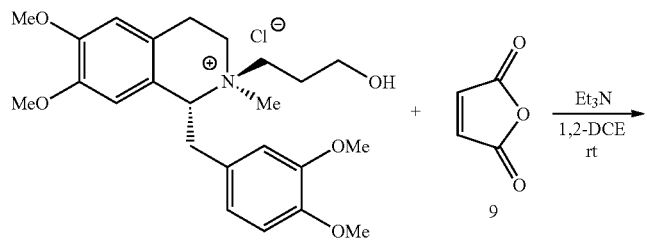
16
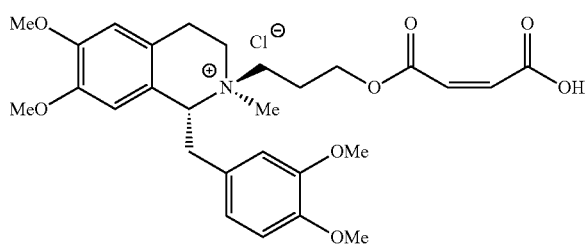
21

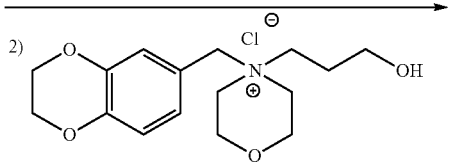

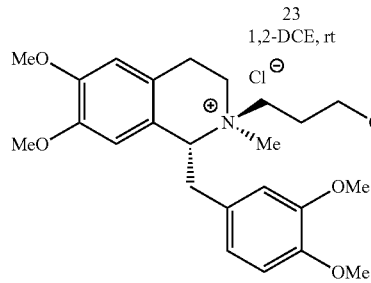

NMB 1521-78

A solution of 16 (5.1 g, 0.011 mol) and maleic anhydride (1.7 g, 0.017 mol) in 1,2-DCE (40 mL) and ACN (50 mL) was charged with triethylamine (1.7 mL, 0.012) over 6 minutes at 0±5° C. The hazy orange mixture was stirred 3 hour at 0±5° C. The resulting dark red mixture was subjected to in vacuo solvent removal at rt to give a red-brown oil that was dissolved in DCM. The solution was extracted with DI water, the DCM phase was retained and the aqueous product solution was pH adjusted to ≤2 using 1M aqueous HCl. The aqueous solution was extracted with 5:1 DCM:ACN in the presence of NaCl (24 wt % aqueous NaCl solution). The DCM/ACN product solution was washed with brine and dried over $Na_2SO_4$. The retained DCM phase was extracted with 1% aqueous $KHCO_3$ and the aqueous product solution was adjusted to a pH≤2 using 1M aqueous HCl. The aqueous solution was extracted with 5:1 DCM:ACN in the presence of NaCl (24 wt % aqueous NaCl solution). The DCM/ACN product solution was washed with brine and was combined with the first DCM/ACN product solution drying over $Na_2SO_4$. The product solution was filtered and subjected to in vacuo solvent removal at rt to give a brown foam. The foam was dissolved in DCM (1 volume) and was added to stirring MTBE (10 volumes) at rt over 1 hour. The slurry was stirred at rt for 6 hour. Compound 21 [5.0 g, 80% yield] was isolated as an off-white solid after vacuum filtration, washing with MTBE and drying under vacuum for 16 h at rt.

To a solution of 21 (0.60 g, 0.0011 mol) in anhydrous 1,2-DCE (20 mL) was added oxalyl chloride (0.48 mL, 0.0055 mol) at 0±5° C. over 2 minutes under $N_2$. The bright yellow solution was stirred at 0±5° C. for 1 hour and rt for 1.5 hours. The solution was subjected to in vacuo solvent removal at rt to provide a purple oil. The oil was subjected to two additional in vacuo solvent distillation cycles at rt using dry 1,2-DCE.

The oil was dissolved in dry 1,2-DCE (8 mL) and was added to a stirring slurry of compound 23 (0.35 g, 0.0011 mol) and 4 Å molecular sieve powder (0.2 g) in mixture of dry 1,2-DCE (15 mL) and ACN (10 mL) over 6 minutes at rt. The pale purple slurry was stirred 17 hours at rt and was subjected to vacuum filtration and in vacuo solvent removal at rt to give a red-brown foam. The foam was dissolved in 1,2-DCE and was extracted with DI water. The aqueous product solution was charged with NaCl (26 wt % aqueous solution) and was extracted with 5:1 $CHCl_3$:ACN. The $CHCl_3$/ACN product solution was washed with 12:1 brine:10% aqueous $KHCO_3$ and 24% aqueous NaCl. The aqueous wash phases were back-extracted with 5:1 $CHCl_3$:ACN and the back-extraction phases were combined with the product solution and were dried over $Na_2SO_4$. Vacuum filtration and in vacuo solvent removal at rt gave a brown foam that was dissolved in DI water. The aqueous solution was stirred with activated carbon (200 mg) and was filtered. The carbon residue was washed forward with DI water. The aqueous product solution was lyophilized to give NMB 1521-78 [0.40 g, 42% yield] as an off-white solid.

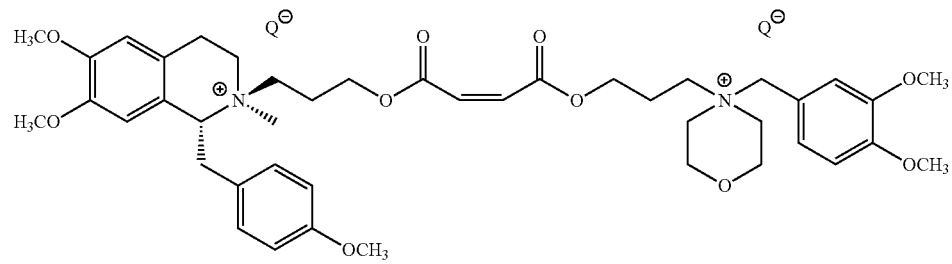

1726-01, 1759-50

Synthesis

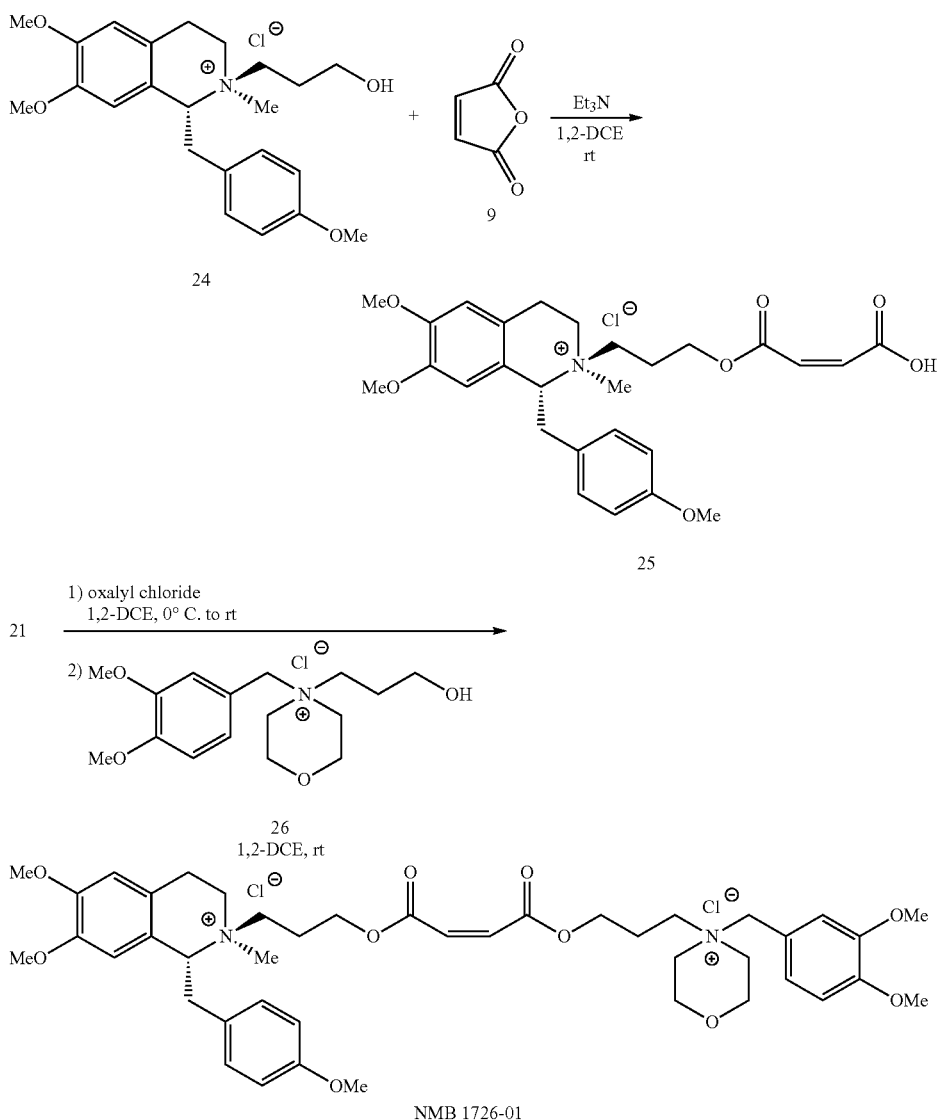

A solution of 24 (2.4 g, 0.0057 mol) and maleic anhydride (0.84 g, 0.0085 mol) in ACN (24 mL) was charged with triethylamine (0.87 mL, 0.0063) over 2 minutes at 0±5° C. The hazy orange mixture was stirred 5 hour at 0±5° C. The resulting dark red mixture was subjected to in vacuo solvent removal at rt to give a red-brown oil that was dissolved in DCM. The solution was extracted with DI water and the aqueous product solution was pH adjusted to ≤2 using 1M aqueous HCl. The aqueous solution was extracted with 5:1 DCM:ACN in the presence of NaCl (24 wt % aqueous NaCl solution). The DCM/ACN product solution was washed with brine and dried over $Na_2SO_4$. The product solution was filtered and subjected to in vacuo solvent removal at rt to give a brown foam. The foam was dissolved in DCM (1 volume) and was added to stirring MTBE (10 volumes) at rt over 1 hour. The slurry was stirred at rt for 6 hour. Compound 25 [2.9 g, 95% yield] was isolated as a light brown solid after vacuum filtration, washing with MTBE and drying under vacuum for 16 h at rt.

To a solution of 25 (1.3 g, 0.0025 mol) in anhydrous 1,2-DCE (40 mL) was added oxalyl chloride (1.1 mL, 0.013 mol) at 0±5° C. over 3 minutes under $N_2$. The dark brown solution was stirred at 0±5° C. for 2 hours. The solution was subjected to in vacuo solvent removal at rt to provide a dark brown oil. The oil was subjected to two additional in vacuo solvent distillation cycles at rt using dry 1,2-DCE. The oil was dissolved in dry 1,2-DCE (8 mL) and was added to a stirring slurry of compound 26 (0.82 g, 0.0025 mol) and 4 Å molecular sieve powder (0.3 g) in mixture of dry 1,2-DCE (35 mL) and ACN (20 mL) over 4 minutes at rt. The dark brown slurry was stirred 20 hours at rt and was subjected to vacuum filtration and in vacuo solvent removal at rt to give a brown foam. The foam was dissolved in 1,2-DCE and was extracted with DI water. The aqueous product solution was charged with NaCl (25 wt % aqueous solution) and was extracted with 4:1 ACN:DCM. The ACN:DCM product solution was washed with 10:1 brine:10% aqueous $KHCO_3$ and brine. The aqueous wash phases were back-extracted with 4:1 ACN:DCM and the back-extraction phases were combined with the product solution and were dried over $Na_2SO_4$. Vacuum filtration and in vacuo solvent removal at rt gave a brown foam that was dissolved in DI water. The aqueous solution was stirred with activated carbon (250 mg) and was filtered. The carbon residue was washed forward with DI water. The aqueous product solution was lyophilized to give NMB 1726-01 [1.1 g, 53% yield] as an off-white solid.
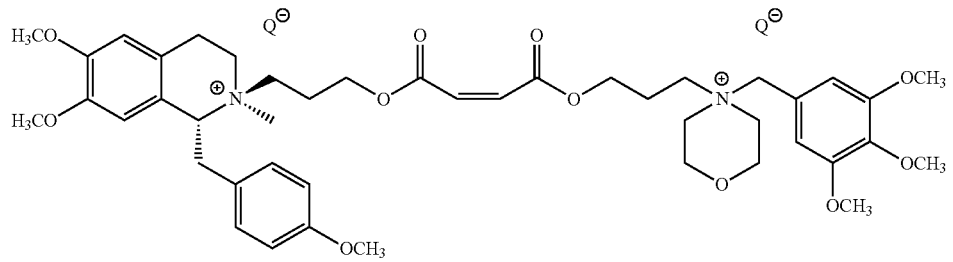
1759-58
Synthesis
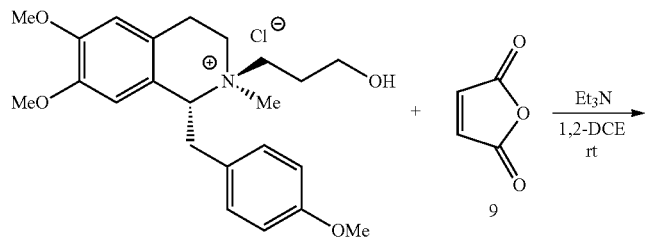
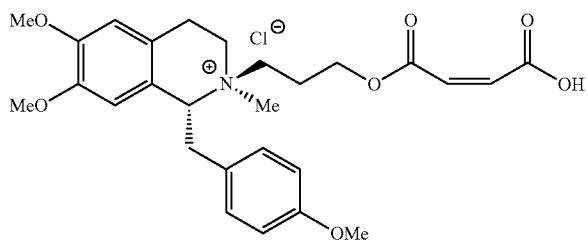
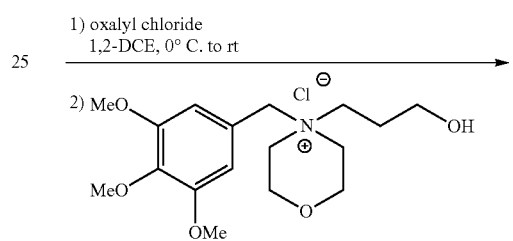
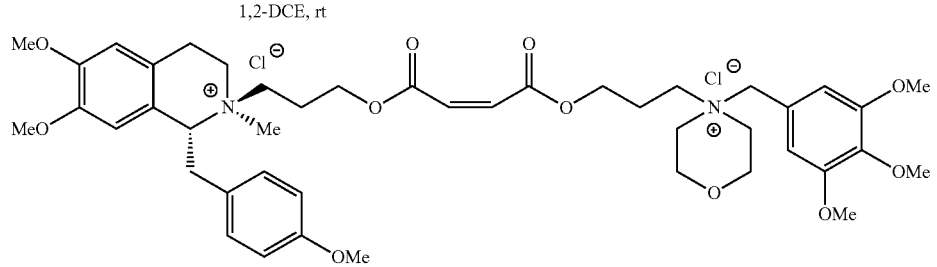
NMB 1759-58

A solution of 24 (2.4 g, 0.0057 mol) and maleic anhydride (0.84 g, 0.0085 mol) in ACN (24 mL) was charged with triethylamine (0.87 mL, 0.0063) over 2 minutes at 0±5° C. The hazy orange mixture was stirred 5 hour at 0±5° C. The resulting dark red mixture was subjected to in vacuo solvent removal at rt to give a red-brown oil that was dissolved in DCM. The solution was extracted with DI water and the aqueous product solution was pH adjusted to ≤2 using 1M aqueous HCl. The aqueous solution was extracted with 5:1 DCM:ACN in the presence of NaCl (24 wt % aqueous NaCl solution). The DCM/ACN product solution was washed with brine and dried over $Na_2SO_4$. The product solution was filtered and subjected to in vacuo solvent removal at rt to give a brown foam. The foam was dissolved in DCM (1 volume) and was added to stirring MTBE (10 volumes) at rt over 1 hour. The slurry was stirred at rt for 6 hour. Compound 25 [2.9 g, 95% yield] was isolated as a light brown solid after vacuum filtration, washing with MTBE and drying under vacuum for 16 h at rt.

To a solution of 25 (0.79 g, 0.0015 mol) in anhydrous 1,2-DCE (30 mL) was added oxalyl chloride (0.66 mL, 0.0076 mol) at 0±5° C. over 2 minutes under $N_2$. The dark brown solution was stirred at 0±5° C. for 3 hours. The solution was subjected to in vacuo solvent removal at rt to provide a dark brown oil. The oil was subjected to two additional in vacuo solvent distillation cycles at rt using dry 1,2-DCE. The oil was dissolved in dry 1,2-DCE (8 mL) and was added to a stirring slurry of compound 19 (0.54 g, 0.0015 mol) and 4 Å molecular sieve powder (0.3 g) in mixture of dry 1,2-DCE (10 mL) and ACN (15 mL) over 3 minutes at rt. The dark brown slurry was stirred 16 hours at rt and was subjected to vacuum filtration. The dark brown solution was diluted with DCM and was extracted with DI water. The aqueous product solution was charged with NaCl (25 wt % aqueous solution) and was extracted with 4:1 ACN:DCM. The ACN:DCM product solution was washed with 10:1 brine:10% aqueous $KHCO_3$ and brine. The aqueous wash phases were back-extracted with 4:1 ACN:DCM and the back-extraction phases were combined with the product solution and were dried over $Na_2SO_4$.

Vacuum filtration and in vacuo solvent removal at rt gave a brown foam that was dissolved in DI water. The aqueous solution was stirred with activated carbon (120 mg) and was filtered. The carbon residue was washed forward with DI water. The aqueous product solution was lyophilized to give NMB 1759-58 [0.37 g, 29% yield] as an off-white solid.

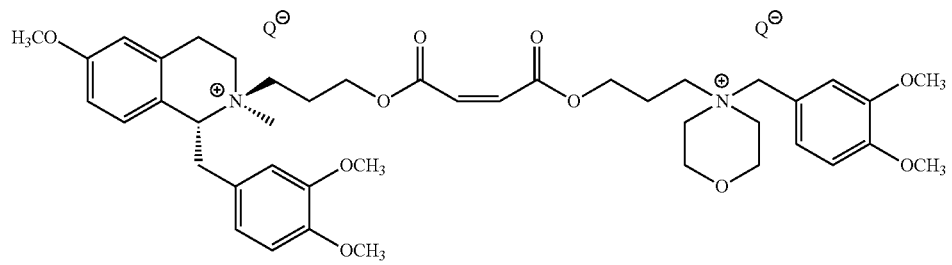

1759-85

Synthesis

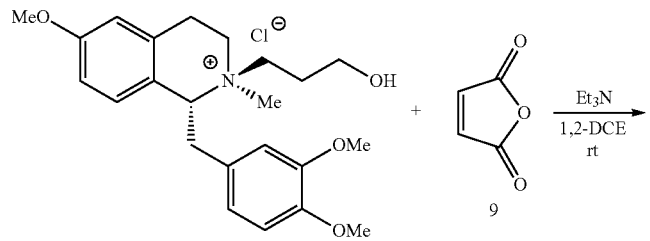

27

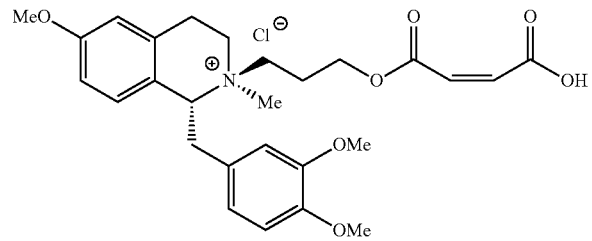

28

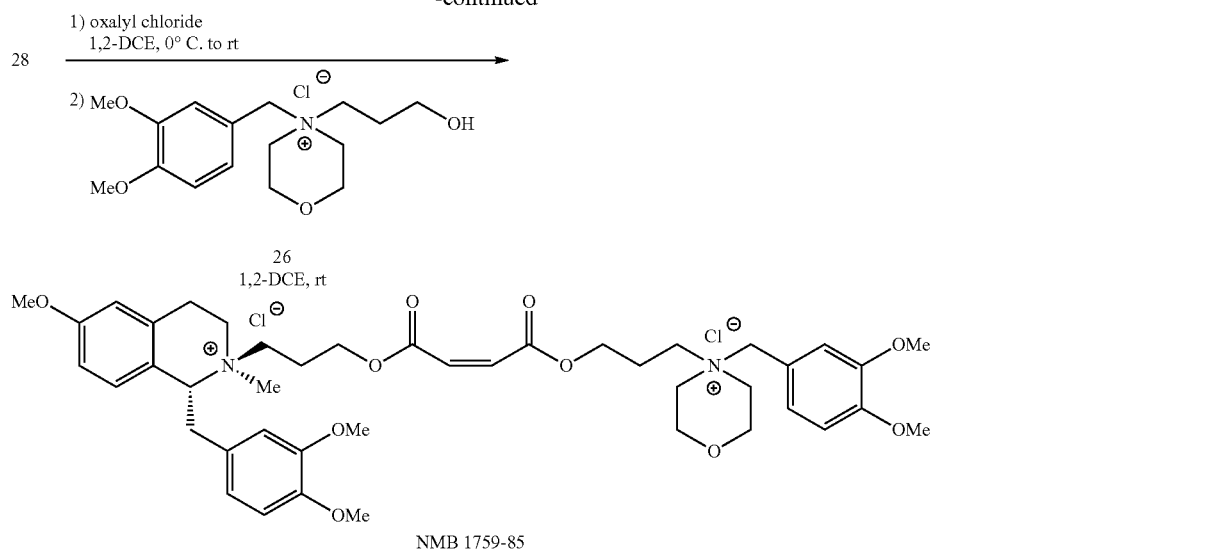

A 1,2-DCE solution of 27 (4.2 g 27, 0.010 mol, 0.14 g 27/g solution) and maleic anhydride (1.5 g, 0.015 mol) in ACN (42 mL) was charged with triethylamine (1.5 mL, 0.011) over 2 minutes at 0±5° C. The hazy orange mixture was stirred 6 hour at 0±5° C. The resulting dark red mixture was subjected to in vacuo solvent removal at rt to give a red-brown oil that was dissolved in DCM. The solution was extracted with 6:1 DI water:10% aqueous $KHCO_3$ and the aqueous product solution was pH adjusted to ≤2 using 6M aqueous HCl. The aqueous solution was extracted with 5:1 DCM:ACN in the presence of NaCl (24 wt % aqueous NaCl solution). The DCM/ACN product solution was washed with brine and dried over $Na_2SO_4$. The product solution was filtered and subjected to in vacuo solvent removal at rt to give a brown foam. The foam was dissolved in DCM (1 volume) and was added to stirring MTBE (10 volumes) at rt over 1 hour. The slurry was stirred at rt for 1 hour. Compound 28 [5.1 g, 98% yield] was isolated as a light brown solid after vacuum filtration, washing with MTBE and drying under vacuum for 14 h at rt.

To a solution of 28 (1.5 g, 0.0029 mol) in anhydrous 1,2-DCE (40 mL) was added oxalyl chloride (1.3 mL, 0.014 mol) at 0±5° C. over 3 minutes under $N_2$. The dark brown solution was stirred at 0±5° C. for 3 hours. The solution was subjected to in vacuo solvent removal at rt to provide a dark brown oil. The oil was subjected to two additional in vacuo solvent distillation cycles at rt using dry 1,2-DCE. The oil was dissolved in dry 1,2-DCE (8 mL) and was added to a stirring slurry of compound 26 (0.94 g, 0.0028 mol) and 4 Å molecular sieve powder (0.3 g) in mixture of dry 1,2-DCE (5 mL) and ACN (15 mL) over 4 minutes at rt. The dark brown slurry was stirred 16 hours at rt and was subjected to vacuum filtration and was diluted with ACN. The dark brown solution was washed with 10:1 brine:10% aqueous $KHCO_3$ and brine. The aqueous wash phases were back-extracted with 4:1 ACN: DCM and the back-extraction phases were combined with the product solution and were dried over $Na_2SO_4$. Vacuum filtration and in vacuo solvent removal at rt gave a brown foam that was dissolved in DI water. The aqueous solution was stirred with activated carbon (200 mg) and was filtered. The carbon residue was washed forward with DI water. The aqueous product solution was lyophilized to give NMB 1759-85 [1.1 g, 46% yield] as an off-white solid.

Maleates: Pyrrolidinium

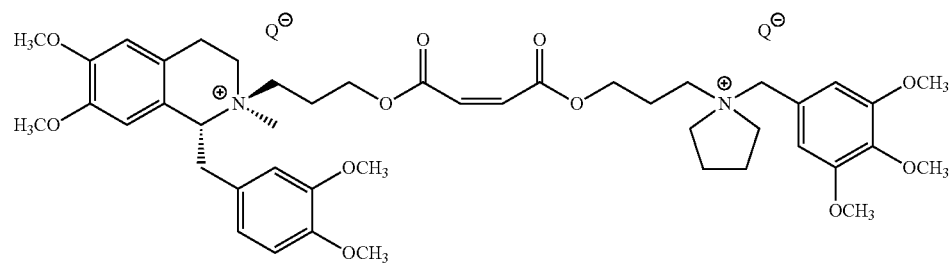

1343-13, 1343-47

Synthesis of 1343-47

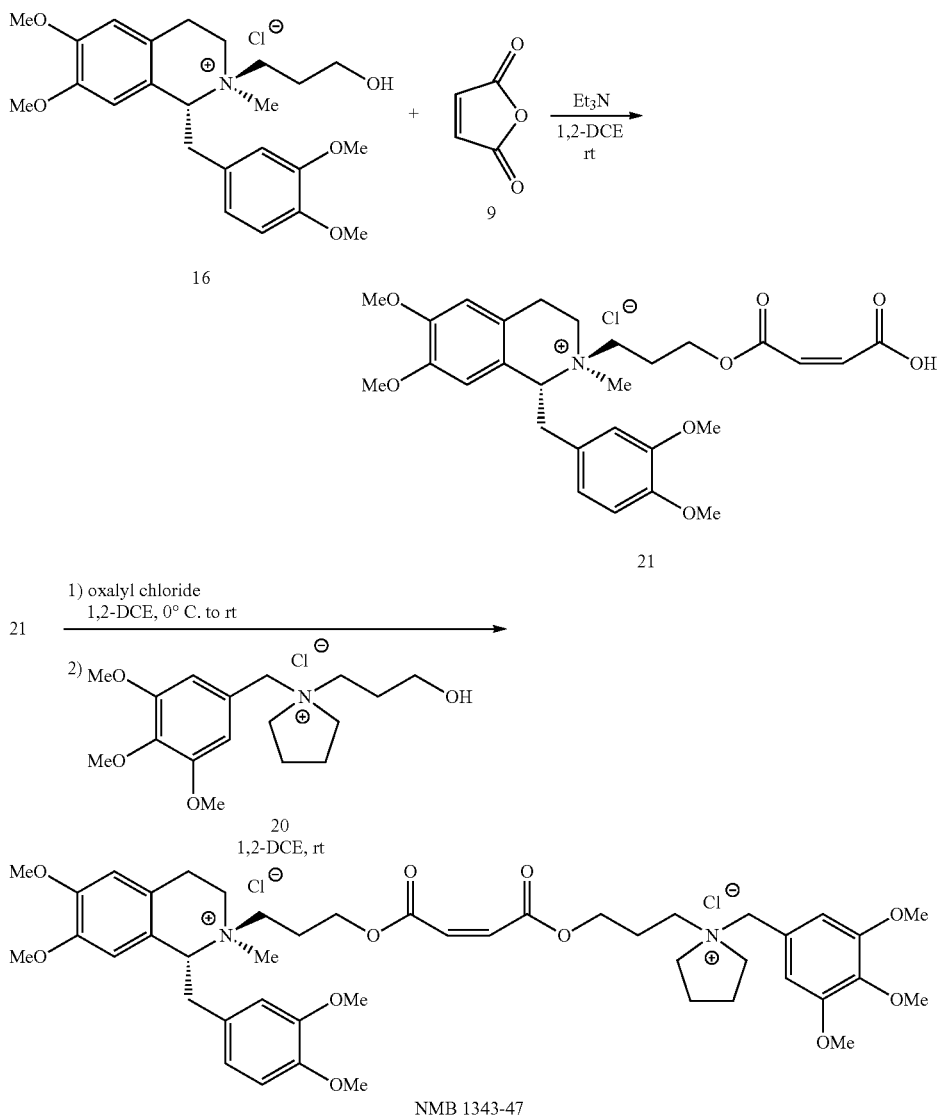

NMB 1343-47

A solution of 16 (3.9 g, 0.0086 mol) and maleic anhydride (1.3 g, 0.013 mol) in 1,2-DCE (30 mL) was charged with triethylamine (1.3 mL, 0.0095) over 5 minutes at 0±5° C. The hazy orange reaction mixture was stirred 1 hour at 0±5° C. and 1 hour at room temperature (rt). The dark red mixture was subjected to in vacuo solvent removal at rt to give a red oil that was dissolved in DCM. The solution was extracted with DI water and the aqueous product solution was adjusted to a pH≤2 using 1M aqueous HCl. The aqueous solution was extracted with 5:1 DCM:ACN in the presence of NaCl (24 wt % aqueous NaCl solution). The DCM/ACN product solution was washed with brine, dried over $Na_2SO_4$, filtered and was subjected to in vacuo solvent removal at rt to give a light yellow oil. The oil was dissolved in DCM (1 volume) and was added to stirring MTBE (10 volumes) at rt over 25 minutes. The slurry was stirred at rt for 1 hour. Compound 21 [3.3 g, 69% yield] was isolated as an off-white solid after vacuum filtration, washing with MTBE and drying under vacuum for 16 h at rt.

To a solution of 21 (2.8 g, 0.0050 mol) in anhydrous 1,2-DCE (50 mL) was added oxalyl chloride (2.2 mL, 0.025 mol) at 0±5° C. over 3 minutes under $N_2$. The bright yellow solution was stirred at 0±5° C. for 1 hour and rt for 2 hours. The solution was subjected to in vacuo solvent removal at rt to provide a purple oil. The oil was subjected to two additional in vacuo solvent distillation cycles at rt using dry 1,2-DCE. The oil was dissolved in dry 1,2-DCE (12 mL) and was added to a stirring slurry of compound 20 (1.6 g, 0.0047 mol) and 4 Å molecular sieve powder (0.3 g) in dry 1,2-DCE (50 mL) over 10 minutes at rt. The pale purple slurry was stirred 16 hours at rt and was subjected to vacuum filtration and dilution with DCM. The solution was extracted with DI water and the aqueous product solution was charged with NaCl (26 wt % aqueous solution) and was extracted with $CHCl_3$. The $CHCl_3$ product solution was washed with 12:1 brine:10% aqueous $KHCO_3$, 24% aqueous NaCl and were dried over $Na_2SO_4$. Vacuum filtration and in vacuo solvent removal at rt gave a dark brown oil. The oil was dissolved in DI water and the aqueous solution was stirred with activated carbon (500 mg) and was filtered. The carbon residue was washed forward with DI water. The aqueous product solution was lyophilized to give NMB 1343-47 [2.1 g, 52% yield] as an off-white solid.

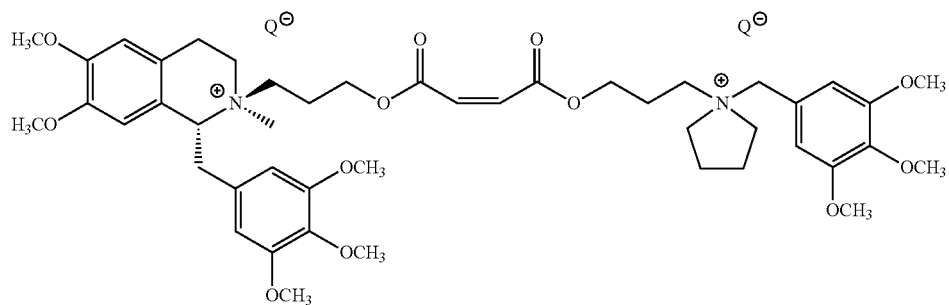
1343-29
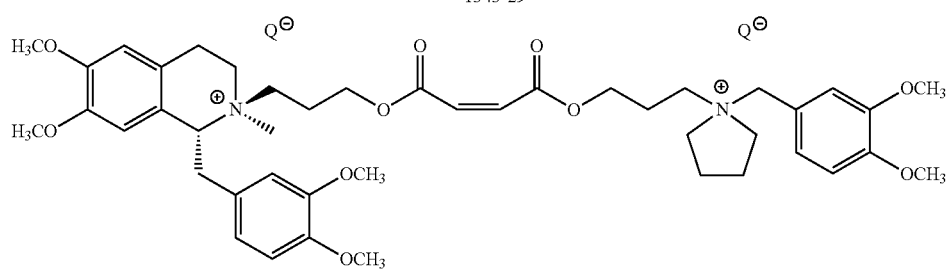
1390-80
Synthesis of 1390-80
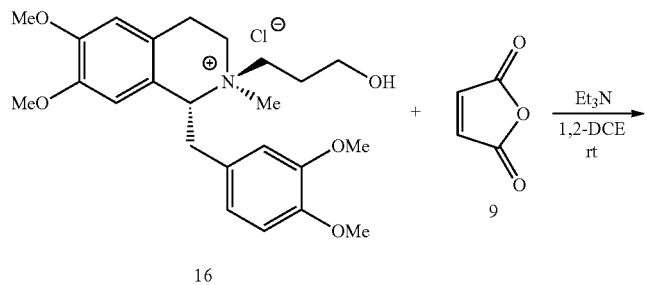
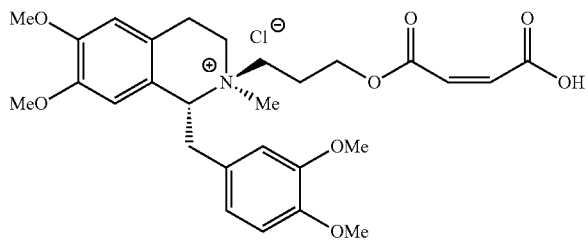
21
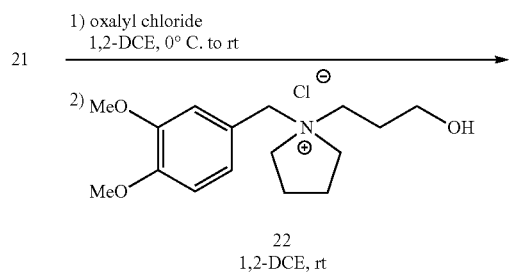

-continued

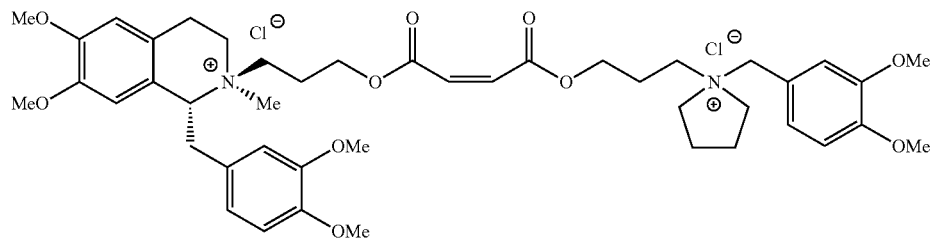

NMB 1390-80

A solution of 16 (8.0 g, 0.018 mol) and maleic anhydride (2.6 g, 0.027 mol) in 1,2-DCE (60 mL) and ACN (80 mL) was charged with triethylamine (2.7 mL, 0.020) over 5 minutes at 0±5° C. The hazy orange reaction mixture was stirred 1 hour at 0±5° C. and 2 hours at room temperature (rt). The dark red mixture was subjected to in vacuo solvent removal at rt to give a red oil that was dissolved in DCM. The solution was extracted with DI water and the aqueous product solution was adjusted to a pH≤2 using 1M aqueous HCl. The aqueous solution was extracted with 5:1 DCM:ACN in the presence of NaCl (24 wt % aqueous NaCl solution). The DCM/ACN product solution was washed with brine, dried over $Na_2SO_4$, filtered and was subjected to in vacuo solvent removal at rt to give a light yellow foam. The foam was dissolved in DCM (1 volume) and was added to stirring MTBE (10 volumes) at rt over 25 minutes. The slurry was stirred at rt for 1 hour. Compound 21 [5.9 g, 60% yield] was isolated as an off-white solid after vacuum filtration, washing with MTBE and drying under vacuum for 16 h at rt.

To a solution of 21 (3.0 g, 0.0055 mol) in anhydrous 1,2-DCE (75 mL) was added oxalyl chloride (2.4 mL, 0.027 mol) at 0±5° C. over 3 minutes under $N_2$. The bright yellow solution was stirred at 0±5° C. for 1 hour and rt for 2 hours. The solution was subjected to in vacuo solvent removal at rt to provide a purple oil. The oil was subjected to two additional in vacuo solvent distillation cycles at rt using dry 1,2-DCE. The oil was dissolved in dry 1,2-DCE (50 mL) and was charged with 4 Å molecular sieve powder (0.5 g) and compound 22 (1.5 g, 0.0046 mol) at rt. The pale purple slurry was stirred 15 hours at rt and was subjected to vacuum filtration to give a clear purple solution that was diluted with DCM. The solution was extracted with DI water. The aqueous product solution was charged with NaCl (23 wt % aqueous solution) and was extracted with $CHCl_3$. The $CHCl_3$ product solution subjected to two cycles of aqueous washes consisting of 12:1 brine:10% aqueous $KHCO_3$ and 24% aqueous NaCl. The product solution was dried over $Na_2SO_4$, filtered and was subjected to in vacuo solvent removal at rt to give a dark orange foam that was dissolved in DI water. The aqueous solution was stirred with activated carbon (400 mg) and was filtered. The carbon residue was washed forward with DI water. The aqueous product solution was lyophilized to give NMB 1390-80 [2.6 g, 56% yield] as an off-white solid.

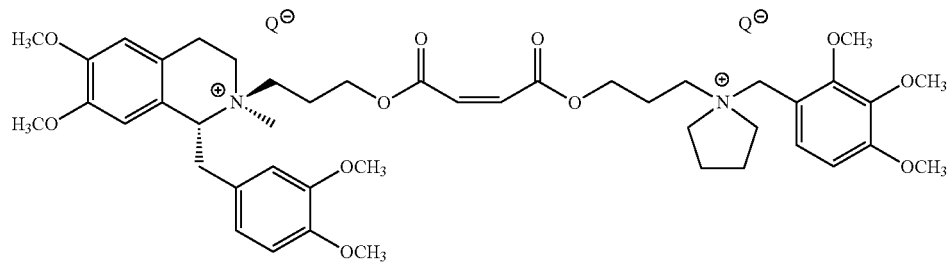

1449-35

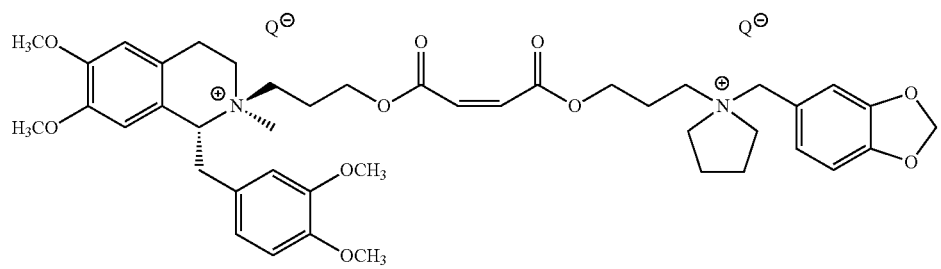

1449-68

-continued

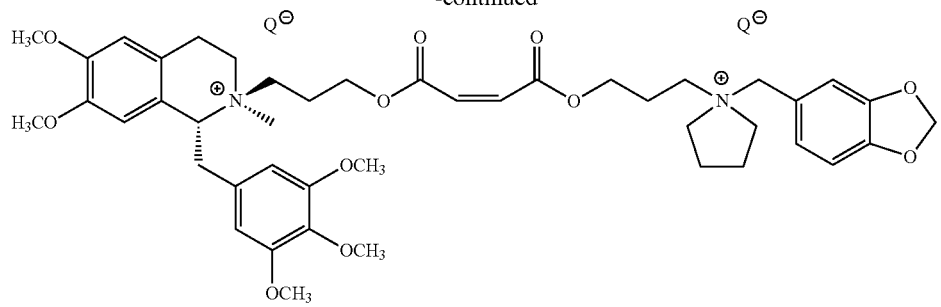

1449-81

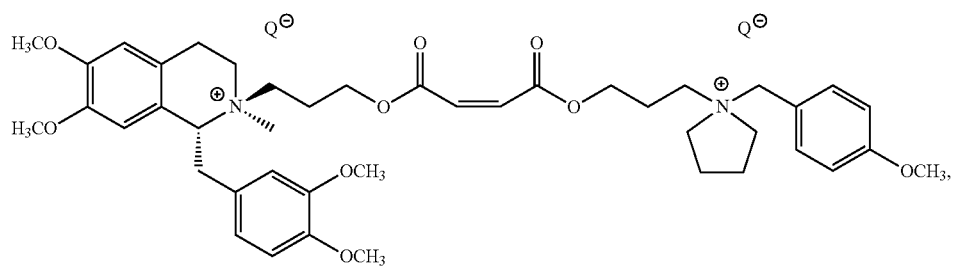

1521-28

Pharmaceutical Compositions and Uses

Compounds of the invention can be used in various compositions adapted to induce neuromuscular blockade in patients as needed in surgical anesthesia. In various embodiments, a compound of the invention produces, upon administration of an effective amount of the compound to a patient, a neuromuscular blockade.

In various embodiments a compound of the invention, administered by injection as a suitable solution, produces neuromuscular blockade of sufficient completeness to enable the compound to effectively be used as an adjunct to anesthesia in major surgery. In various embodiments, an effective amount of an inventive compound for administration to a human patient is about 0.01-10 mg per kg patient bodyweight. More specifically, in various embodiments, the effective amount is about 0.1-1 mg per kg patient bodyweight. The compound can be administered in a manner known to the anesthesiologist or surgeon of ordinary skill in the art, using the methods and apparatus well known for this procedure in surgery.

In various embodiments, the invention provides a composition comprising a compound of the invention and a suitable biocompatible solvent. The composition can be adapted for parenteral administration to a human patient, comprising an injectable solution of the compound in a suitable biocompatible solvent. In various embodiments, an injectable solution of a compound of the invention in a suitable solvent comprises about 1 mg/mL to about 10 mg/mL of the compound per dose of the injectable solution. The solution can be administered via syringe, via intravenous drip, or via any of the techniques well known to the practitioner of the art.

In various embodiments, a suitable biocompatible solvent comprises sterile, pyrogen-free water. The solvent can further comprise isotonic NaCl, or other tonicity adjustment substances. In various embodiments, the suitable biocompatible solvent can comprise alcohol, a polyethylene glycol, DMSO, or any mixture thereof, which can be neat or can be in a mixture with water.

Compounds of the invention are known to be, to some extent, unstable over prolonged storage in alkaline medium. Accordingly, a dosage form of the invention can be adjusted to an acidic pH for stabilization. In various embodiments of a solution dosage form of the invention, the pH of the solution is about 2.5 to about 3.5. In various embodiments, the dosage form can be adapted for frozen storage, such as by packaging in containers that can withstand freezing, bearing freeze-resistant labeling, and the like.

In various embodiments, the invention provides compounds, the neuromuscular blockade effects of which are reversible by administration to the patient of an effective amount of a thiol compound. An outstanding feature of the present invention is the ready reversibility of the neuromuscular blockade effects of some of the compounds of the invention by administration to the patient, such as by intravenous administration, of a thiol compound, such as L-cysteine or a pharmaceutically acceptable salt thereof, D-cysteine or a pharmaceutically acceptable salt thereof, or glutathione or a pharmaceutically acceptable salt thereof, or a stereoisomer of glutathione or a pharmaceutically acceptable salt thereof.

As discussed herein, without wishing to be bound by theory, the inventor believes that inactivation of the neuromuscular blockade effects of various embodiments of compounds of the invention by a thiol compound takes place via an intermolecular reaction in vivo of the inventive NMBA compound and the thiol, producing a reaction product therebetween. Each of the compound classes of fumarates, and maleates, are believed to be susceptible to this reaction, and it has been found that the neuromuscular blockade effects of fumarates (including chlorofumarates) and maleates are reversible by administration of thiol compounds such as cysteine (L or D) or glutathione.

In various embodiments, the invention provides a method of inducing neuromuscular blockade in a patient, comprising administering an effective amount of a compound of the invention to the patient. In various embodiments, the effective amount is about 0.01-10 mg per kg patient bodyweight. More specifically, the effective amount is about 0.1-1 mg per kg patient bodyweight. The inventive method can comprise inducing neuromuscular blockade as part of a regimen of anesthesia, which as described above is well known to be desirable for carrying out many types of surgical procedures where movement of the patient undergoing surgery is dangerous and undesirable.

In various embodiments, administration of a compound, for example in the form of a composition of the invention as described above, to a patient produces neuromuscular blockade wherein the neuromuscular blockade is non-depolarizing. In various embodiments, the neuromuscular blockade is achieved with little or no circulatory effect.

An outstanding feature of various embodiments of compounds of the invention is that the neuromuscular blockade can be subsequently reversed by administration of a thiol compound. It is believed by the inventor herein that reversal occurs by a reaction of the thiol compound with a reactive multiple bond of an inventive compound. Accordingly, fumarates and maleates of the invention have thiol-reversible effects.

The thiol compound used for reversal of the neuromuscular blockade can be L-cysteine or a pharmaceutically acceptable salt thereof, D-cysteine or a pharmaceutically acceptable salt thereof, or glutathione or a pharmaceutically acceptable salt thereof, or a stereoisomer of glutathione or a pharmaceutically acceptable salt thereof.

In various embodiments, the blockade is reversible within about 2-5 minutes after administration of the thiol compound to the patient following induction of the neuromuscular blockade. Rapid reversal can be advantageous in carrying our surgical procedures, as it allows mechanical respiration to be used for only the necessary period of time, insomuch as the blockade can inhibit the action of the patient's diaphragm in natural respiration. Accordingly, the thiol compound such as cysteine (L or D) or a salt thereof can be administered to the patient immediately following a surgical procedure for which a compound of formula (I) had been previously administered to the patient. For example, the thiol compound used to immediately reverse the neuromuscular blockade following surgery can comprise cysteine or a salt thereof wherein the cysteine or salt thereof is administered at a dose of about 10 mg/kg to about 50 mg/kg on a free base basis. More specifically, the cysteine or salt thereof can be D-cysteine hydrochloride. Use of a D-cysteine salt can be more free of unwanted side-effects than the use of an L-cysteine salt. A solution of L-cysteine, D-cysteine, glutathione, or a stereoisomer of glutathione can be adjusted to a pH of about 5-6 prior to administration to the patient to reverse the neuromuscular blockade.

Accordingly, the invention provides a use of a compound of the invention for creating neuromuscular blockade, wherein in various embodiments the blockade is reversible by administration of a thiol compound.

In various embodiments, the invention provides a dosage form of a compound of the invention comprising an injectable solution of the compound in a suitable biocompatible solvent. The dosage form can comprise about 1 mg/mL to about 10 mg/mL of the compound in the biocompatible solvent. As discussed above, the suitable biocompatible solvent can comprise sterile, pyrogen-free water, optionally containing isotonic NaCl. Or, the suitable biocompatible solvent can comprise alcohol, a polyethylene glycol, DMSO, or any mixture thereof, optionally further including water or an isotonic NaCl solution. In various embodiments the pH of the solution is about 2.5 to about 3.5 to stabilize the dosage form against degradation over time of the NMBA. The dosage form of the invention can be adapted for frozen storage. In various embodiments the pH of the solution can be adjusted, for example to a pH of about 5-6, prior to administration to the patient.

In various embodiments, the invention provides a kit comprising a compound of the invention in a first container and, optionally, a thiol compound suitable for reversing the neuromuscular blockade effect of the compound on a patient in a second container. The second container with the thiol compound in suitable formulation can be supplied when the inventive compound comprises a thiol-reversible compound. The first container can comprise a dosage form of any of the invention as discussed above. When a second container with a neuromuscular blockade-reversing thiol compound is provided, the second container of the kit can comprise a solution of L-cysteine hydrochloride, D-cysteine hydrochloride, or both. In various embodiments, the solution can be buffered to a pH of about 2-3 for storage. In various embodiments, the kit further comprises a third container comprising a buffer to adjust the pH of the solution of the first container, the second container, or both, to about 5-6 prior to administration to the patient.

Accordingly, in various embodiments the invention provides a method of inducing a neuromuscular blockade in a mammal for therapeutic purposes comprising administering to the mammal the neuromuscular blocking agent of the invention. As described, the neuromuscular blockade can be induced, e.g., for respiratory intubation, when the mammal is subjected to general anesthesia, such as for a human patient during a surgical procedure, or for a domestic or zoo mammal undergoing surgery.

Due to the reversibility of the neuromuscular blockade cause by the ultra-short, short, and intermediate duration effects of the NMBA compounds of the invention, the neuromuscular blockade can be reversed by administering to the patient an effective amount of at least one of L-cysteine, D-cysteine, or a mixture thereof; N-acetylcysteine; glutathione; homocysteine; methionine; S-adenosyl-methionine; or penicillamine; or a pharmaceutically acceptable salt thereof; wherein the neuromuscular blockade is generated by one of the NMBA compounds of the invention. For example, D-cysteine or a pharmaceutically acceptable salt thereof, in a pharmaceutically acceptable liquid carrier, can be administered intravenously. A single dosage of the reversing agent, for example D-cysteine, can be administered in a dosage of about 0.1 mg/kg to about 500 mg/kg.

Compounds of the invention can be used to provide muscle relaxation during anesthesia and surgery and in emergency medicine, with the features of more rapid spontaneous recovery as well as immediate antagonism at any time by D or L-cysteine. The compounds have less circulatory side-effects due to apparent histamine release.

A therapeutically effective amount of the neuromuscular blocking compositions of the present invention is sufficient to provide muscle relaxation during anesthesia and surgery and in emergency medicine in a subject. The dosage of active ingredient(s) may vary, depending on the reason for use and the individual subject. The dosage may be adjusted based on the subject's weight, the age and health of the subject, and tolerance for the compound or composition. A suitable dose to obtain a neuromuscular blockade for adult humans (150 lbs. or 70 kg) is about 0.1 mg to about 500 mg, or in some embodiments about 1 mg to about 500 mg, or in other embodiments about 0.5 mg to about 150 mg, or in further embodiments about 3.5 mg to about 50 mg. Thus a suitable pharmaceutical parenteral preparation for administration to humans will preferably contain 0.1 to 50 mg/ml of one or more of the present compounds in solution or multiples thereof for multi-dose vials.)

A therapeutically effective amount of antagonists of neuromuscular blocking compounds of the present invention is sufficient to antagonize a neuromuscular blockade caused by administration to a mammal of a neuromuscular blocking agent of the invention. The dosage of active ingredient(s) may vary, depending on the reason for use and the individual subject. The dosage may be adjusted based on the subject's weight, the age and health of the subject, and tolerance for the compound or composition. A suitable dose of cysteine or a cysteine-like molecule to antagonize a neuromuscular blockade in adult humans (with an average weight of about 150 lbs. or 70 kg) is about 5 mg to about 10,000 mg, or about 50 mg to about 2000 mg or about 150 to about 750 mg. Thus a suitable pharmaceutical parenteral preparation for administration to humans will preferably contain 0.1 to 2000 mg/ml of cysteine or a cysteine-like molecule, or a combination of cysteine and cysteine-like molecules, in solution or multiples thereof for multi-dose vials.) Alternatively, in general, cysteine dosages in humans for reversal of neuromuscular blockades are about 10-100 mg/kg or about 30-50 mg/kg. Thus, the typical dosages and volumes of cysteine to be injected will likely be in the range of about 1000-10000 mg or about 2000-5000 mg of cysteine (based on body weights of 70-100 kg). Thus, compositions and methods have been developed to provide these amounts of cysteine in convenient volumes of about 5 ml to about 50 ml or about 10 ml to about 25 ml. Such compositions can be administered quickly, for example, as a single bolus intravenous injection over a period of time of about 2 seconds to about 60 seconds, or about 5 seconds to about 10 seconds. The solutions described herein have concentrations of cysteine that are about 100-300 mg/ml or about 180-250 mg/ml cysteine so that appropriate in vivo concentrations of cysteine are achieved after administration to quickly reverse a neuromuscular blockade.

The present invention also provides a method to provide muscle relaxation during anesthesia and surgery and in emergency medicine in a subject, by administering to the subject a composition comprising a therapeutically effective amount of a subject neuromuscular blocking compound and a pharmaceutically acceptable excipient. The excipient can be a biocompatible solvent, such as sterile isotonic saline, and the composition can be suitable for parenteral administration to the patient. The invention also provides a therapeutic method of antagonizing a neuromuscular blockade caused by administration to a mammal of a neuromuscular blocking agent of the invention, wherein the method comprises administering an effective amount of a neuromuscular blockade antagonist to the mammal, as described herein.

Another aspect of the invention is a therapeutic method of antagonizing a neuromuscular blockade caused by administration to a mammal of a neuromuscular blocking agent of the invention, wherein the method comprises administering an effective amount of a neuromuscular blockade antagonist to the mammal. Examples of neuromuscular blockade antagonists include cysteine, which may include L-cysteine, D-cysteine, or a mix thereof, glutathione, N-acetylcysteine, homocysteine, methionine, S-adenosylmethionine, penicillamine, a related cysteine analog, a combination thereof or a pharmaceutically acceptable salt thereof. In some embodiments, the antagonist is cysteine. In other embodiments, the antagonist is cysteine combined with glutathione. In other embodiments, the antagonist is cysteine or glutathione combined with any of the other antagonists.

Cysteine has been shown to rapidly antagonize a neuromuscular blockade induced by compounds described herein. To accomplish the reversal of a neuromuscular blockade generated by one of these agents, cysteine is administered by intravenous injection. However, the natural pH of cysteine hydrochloride solutions at concentrations of 50 mg/ml or more in aqueous solution (e.g., 0.9% saline) is very low, ranging from about pH 0.8 to about pH 1.0. Moreover, cysteine is not soluble at concentrations greater than 50 mg/ml in its base form, but higher concentrations of cysteine are more conveniently administered for reversal of neuromuscular blockades. For example, bolus administration of volumes greater than 50 ml over a time period of 5-10 sec is generally not convenient in an operating room. Therefore, to be administered to patients, cysteine solutions have been developed that have higher concentrations and higher pH values as described herein.

In general, cysteine solutions for use as a neuromuscular blockade reversal agent in clinical practice have some or all of the following general properties:
1) A physiological solution with about 150-300 mg/ml (or 150-250 mg/ml) cysteine;
2) A pH of the solution of 4.0-5.0 to prevent venous irritation and/or trauma; and/or
3) Antioxidant additives to prevent formation of the cysteine dimer, cystine, which is inactive and insoluble.

According to the invention, cysteine solutions with these properties are stable, nonirritating and appropriate for bolus injection in an operating room scenario.

Either the L-isomer or the D-isomer of cysteine can be used in the cysteine solutions provided herein, or a combination of L-cysteine and D-cysteine can be employed, e.g., the racemic form. L-cysteine is produced endogenously and crosses the blood-brain barrier largely via a specific amino acid transporter. Thus, L-cysteine may contribute to central nervous stimulation following administration of large doses (e.g., 100 mg/kg or more). In contrast, the D-isomer of cysteine is not normally found in substantial quantities within the body, and is not a substrate for metabolic processes involving L-cysteine such as glutathione synthesis. In addition, D-cysteine is not a major substrate for the amino acid transporters which are L-isomer specific. As illustrated herein, D-cysteine can effectively reverse a neuromuscular blockade by neuromuscular blocking agent. Moreover, at 100 mg/kg, D-cysteine elicits less of a rise in mean arterial pressure than L-cysteine, consistent with the probability of less entry into the central nervous system.

Selected NMBA compounds were tested as described in PCT/US2010/000796 application by an inventor herein, published as WO2010/107488, which is incorporated by reference, see pages 66-78. Dose-response curves for twitch blockade by test compounds were generated as described. To ensure minimal cumulative/residual influence on these data, sequential dosing was done in escalating fashion. Successive doses were separated by at least three estimated half lives beyond complete recovery of the previous dose to TOF of 110-120%, which is normal for these monkeys. Only the first one or two doses yielding 5 to 99% blockade were included from any single experiment for computation of dose-response data. Comparative studies of spontaneous recovery versus antagonism/reversal were done at least 3 estimated half-lives following dose-response studies. ED50 and ED95 were computed from the regression of log dose vs. the logit of percentage blockade of twitch. Results are presented in Table 1.

As is apparent, for the 13 compounds reported in Table 1, all showed high potency (0.05 to 0.25 mg/kg actual doses) and short duration of action (about 12 minutes to under 5 minutes, depending on the specific compound).

FIG. 1 is a graph showing data from a dose-response study for compound 1759-50 (also known as compound 1726-01):

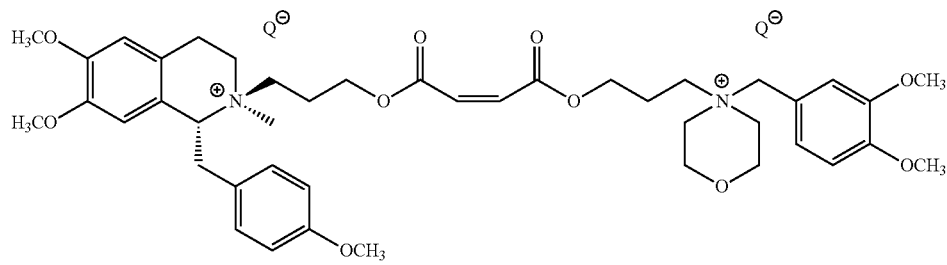

in rhesus monkeys. A statistical analysis provides and ED95 value of 0.054±0.0022 mg/kg. For comparison, gantacurium was determined to have an ED95 in the a control study of 0.063±0.0021 mg·kg.

Figure 2:
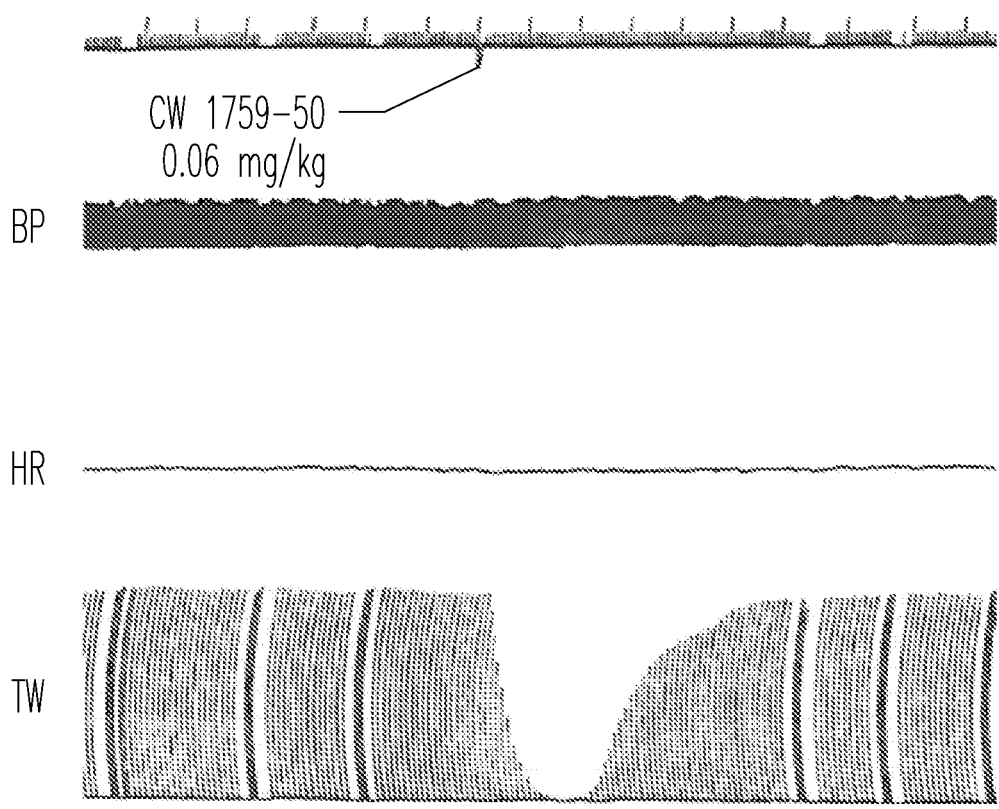
FIG. 2 shows a twitch response time course of spontaneous recovery of a rhesus monkey for a 0.06 mg/kg dose of the same compound 1759-50 provided to the test subject.

FIG. 2 shows a time course of spontaneous recovery for a 0.06 mg/kg dose of the same compound. As can be seen, the neuromuscular blockade lasts about six minutes, with no apparent effect on blood pressure, and, in contrast to succinylcholine, there is no apparent effect on heart rate. Thus, the undesired side effect of tachycardia is not induced by a compound of the invention at a dose effective to induce NMB.

Figure 3:
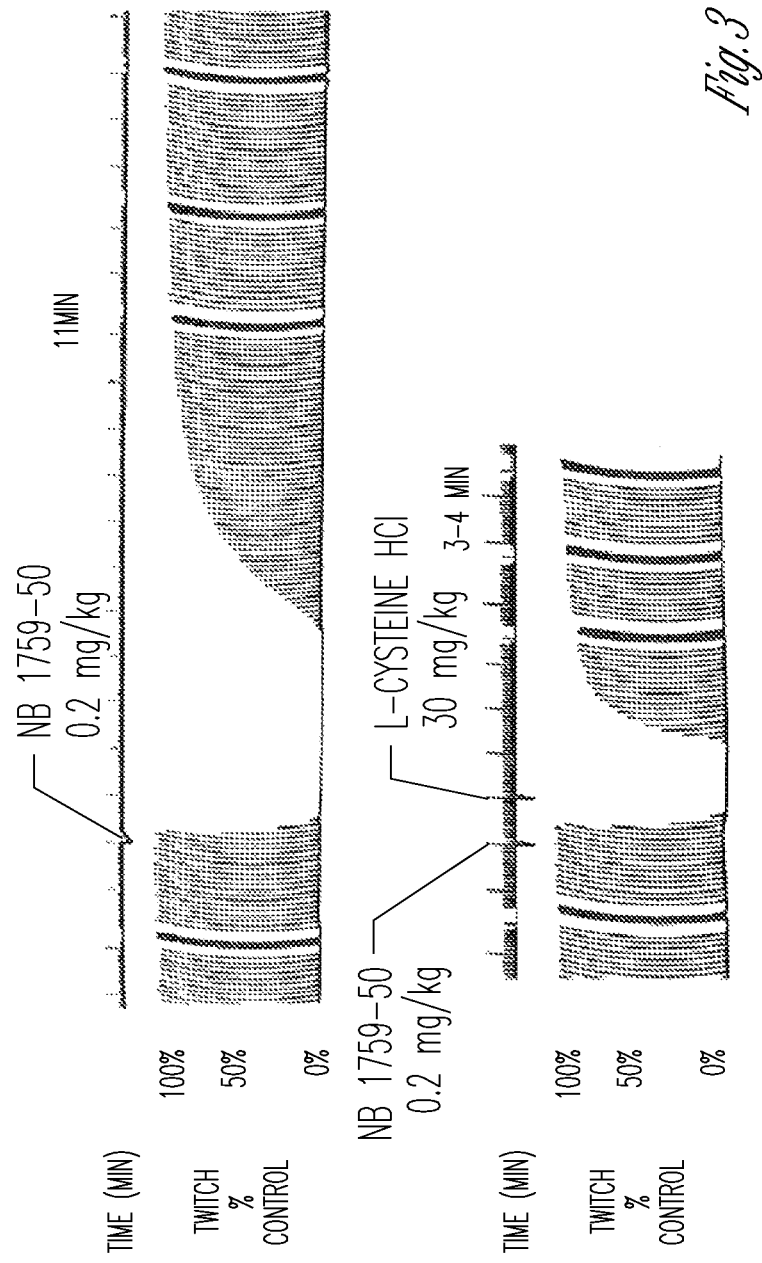
FIG. 3 shows a time course of twitch response for the neuromuscular blockade induced by compound 1759-50 at a dose of 4× the ED95 dose, comparing spontaneous reversal time versus reversal time using a 30 mg/kg dose of reversing agent L-cysteine hydrochloride.

FIG. 3 shows a time course of twitch response for the neuromuscular blockade induced by compound 1759-50 at a dose of 4× the ED95 dose, comparing spontaneous reversal versus reversal with 30 mg/kg L-cysteine hydrochloride. The spontaneous reversal at this high dosage required about 11 minutes, while the L-cysteine dose terminated the neuromuscular blockade about two minutes following administration.

Figure 4:
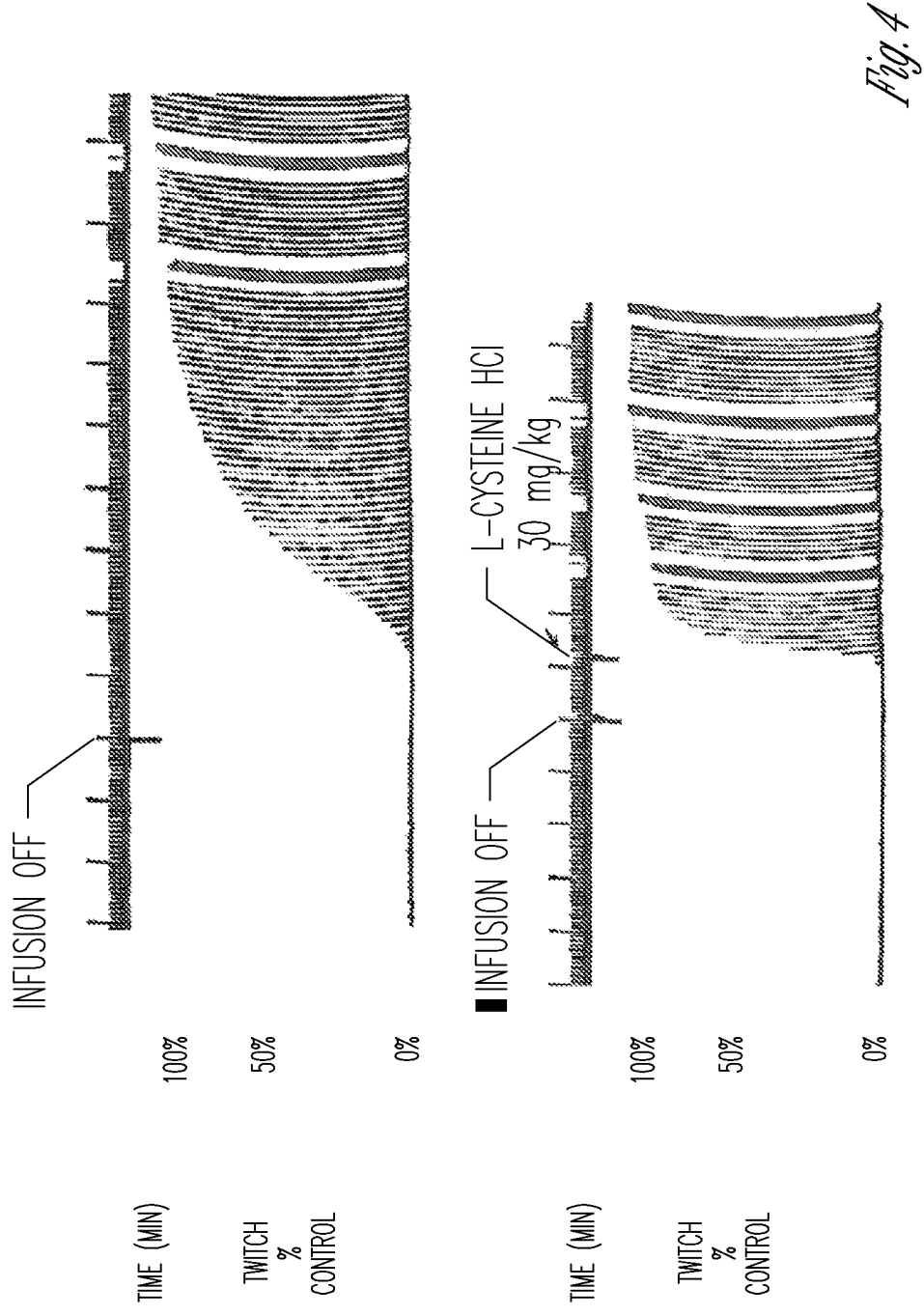
FIG. 4 shows a time course of twitch response for compound 1759-50 complete block, comparing spontaneous reversal time versus reversal time with a 30 mg/kg dose of reversing agent L-cysteine hydrochloride.

FIG. 4 shows a time course of twitch response for the neuromuscular blockade induced by compound 1759-50 at 100% block. As can be seen, the cysteine-induced reversal occurs within about 2 minutes, compared to more than 10 minutes for spontaneous reversal of blockade.

Figure 5:
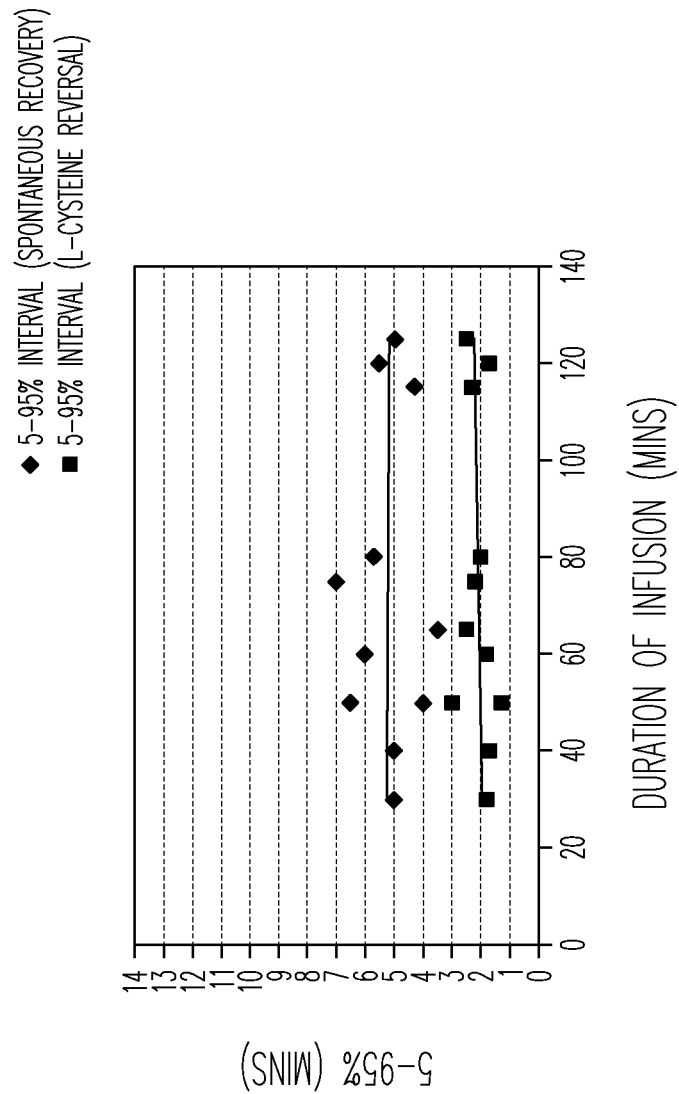
FIG. 5 shows a comparison of the relationship of 5-95% twitch recovery interval to the duration of infusion of compound 1759-50 in the rhesus monkey.

FIG. 5 shows a comparison of the relationship of 5-95% twitch recovery interval to the duration of infusion of compound 1759-50 in the rhesus monkey. As can be seen, the mean time to recovery, spontaneous or L-cysteine induced, is not significantly effected by the previous duration of infusion by the NMBA.

These data indicate that recovery from neuromuscular blockade induced by compound 1759-50, either bolus or infusion, is unaffected by dosage or duration of infusion, and that 30 mg/kg L-cysteine reverals is equally effective at any time following bolus or infusion administration.

TABLE 1

| Compound | Acid/Ester Chemical Category | ("Right") Quaternary #2 | ED 95 (mg/kg) | Duration (min ± SD) | Actual Dose Administered (mg/kg) | (n) | Reversibility (Cysteine) |
|---|---|---|---|---|---|---|---|
| 1521-78 (1566-14) | Maleate | Morpholinium | 0.05 | 12.1 ± 2.1 | .05 | 11 | Yes |
| 1521-83 (1566-07) | Maleate | Morpholinium | 0.07 | 7.9 ± 2.3 | 0.08 | 22 | Yes |
| 1343-13, (1343-47) | Maleate | Pyrrolidinium | 0.06 | 8.8 ± 2.6 | 0.06 | 19 | Yes |
| 1390-80 | Maleate | Pyrrolidinium | 0.07 | 9.0 ± 2.1 | 0.08 | 11 | Yes |
| 1598-46 | Chloro-fumarate | Morpholinium | 0.1 | 6.8 ± 2.3 | 0.1 | 4 | Yes |
| 1521-74 | Chloro-fumarate | Morpholinium | 0.16 | 4.3 ± 1.1 | 0.16-0.20 | 3 | Yes |
| 1566-22 | Chloro-fumarate | Morpholinium | 0.19 | 3.7 ± 0.3 | 0.24-0.25 | 3 | Yes |
| 1326-69 (1302-47) | Chloro-fumarate | Pyrrolidinium | 0.11 | 4.5 ± 1.8 | 0.1 | 10 | Yes |
| 1343-05 | Chloro-fumarate | Piperidinium | .07 | 6.7 ± 2.1 | 0.5-0.8 | 5 | Yes |
| 1759-85 | Maleate | Morpholinium | 0.22 | 5.4 ± 1.3 | 0.2 | 4 | Yes |
| 1726-01, (1759-50) | Maleate | Morpholinium | 0.05 | 7.6 ± 2.4 | 0.05 | 11 | Yes |
| 1625-01 | Maleate | Morpholinium | 0.09 | 6-9 | 0.10 | 6 | Yes |
| 1759-58 | Maleate | Morpholinium | 0.064 | 6-8 | 0.05-0.06 | 8 | Yes |
| 1625-05 | Maleate | Morpholinium | 0.09 | 6 | — | — | Yes |
| 1566-01 | Chloro-fumarate | Morpholinium | 0.61 | 8 | 0.06 | 1 | Yes |
| 1521-34 | Maleate | Morpholinium | 0.47 | 14 | .05 | 2 | Yes |
| 1521-08 | Maleate | Morpholinium | .103 | 10 | .10 | 7 | Yes |
| 1449-35 | Maleate | Pyrrolidinium | .126 | 5 | .10 | 2 | Yes |
| 1521-28 | Maleate | Pyrrolidinium | .335 | 6.5 | 0.4 | 1 | Yes |

All compounds are Isoquinolinium for quaternary #1 (left side).

Table 2 shows data indicating the total duration and 5-95% recovery intervals, spontaneous and L-cysteine (30 mg/kg) induced, from neuromuscular blockade with compound 1759-50.

rate was measured by tachograph from the arterial pulse wave. Core temperature was kept at 36.5-38.0° C. by warming blankets. Electrocardiogram and pulse oximetry were monitored continuously.

TABLE 2

Reversal of CW 1759-50 by L-Cysteine vs. Spontaneous Recovery in Monkeys following Bolus Dosage and Infusions

| Key Points | Dose mg/kg | ED | n | Total Duration (min)* (Spontaneous Recovery) | 5-95% Interval (Spontaneous Recovery) | n | 5-95% Interval with L-Cysteine | n |
|---|---|---|---|---|---|---|---|---|
|  | 0.05- 0.06 | $ED_{99}$ | 57 | 7.3 ± 0.3 | 5.2 ± 0.2 | 33 | NA | NA |
| Point "A"*** | 0.2 | 4x $ED_{95}$ | 55 | 11.9 ± 0.3 | 6.2 ± 0.2 | 45 | 1.9 ± 0.2 | 9 |
| Point "B"**** | Continuous Infusions, 30-120 mins |  | 22 | NA | 5.2 ± 0.3 | 11 | 2.1 ± 0.2 | 11 |

*From injection to 95% twitch height following bolus doses
**L-Cysteine dosage 30 mg/kg
***Comparative recovery intervals (spontaneous vs. L-cysteine reversal) when L-cysteine is given at +1 min following bolus dosage of 4x ED95 (0.2 mg/kg)
****Comparative recovery intervals (spontaneous vs. L-cysteine reversal) when L-cysteine is given at +1 min following discontinuation of infusion.
a p < 0.01 vs. spontaneous recovery
b p < 0.05, reversal of 4x ED95 vs. reversal of infusions

TABLE 3

Comparison of Compound 1759-50 with Gantacurium

|  | Dose (mg/kg) | Blockade (%) | Onset (sec) | Total Duration (min) | n |
|---|---|---|---|---|---|
| Gantacurium | 0.064 ± 0.010 | 99.2 ± 0.5 | 97.1 ± 11.7 | 7.4 ± 1.9 | 9 |
| CW1759-50 | 0.060 ± 0.012 | 99.3 ± 0.2 | 94.0 ± 8.7 | 8.2 ± 1.5 | 8 |

With respect to % blockade, time to onset, and total duration of effect, compound 1759-50 is comparable to gantacurium in potency.

Studies in Anesthetized Rhesus Monkeys
Animal Preparation and Care

Experiments were approved by the Institutional Animal Care and Use Committee of Weill Medical College of Cornell University (New York, N.Y.) and of Albany Medical College (Albany, N.Y.), where the studies were conducted. A colony of 10 adult male monkeys (*Macaca mulatta*) weighing 8-18 kg was studied at ~6 week intervals. Animals were housed and cared for in accordance with the Guide for Care and Use of Laboratory Animals (National Research Council, Washington, D.C.). They were fed a standard Old World monkey diet, enriched with fruits and vegetables, and other dietary novelties and were followed throughout the study to verify normal health by physical examination, body weight, and clinical laboratory studies (Complete Blood Count, Blood Urea Nitrogen and creatinine, and liver function tests).

Anesthesia and Experimental Set Up

On the day of each study, monkeys received ketamine (7-10 mg/kg i.m.) followed by tracheal intubation under topical anesthesia with 4% lidocaine. Ventilation was controlled at 10 mL/kg and 20 breaths/min with isoflurane (1.0-2.0%) and $N_2O/O_2$ (2:1 mixture). Ringers lactate was administered at ~10 ml $kg^{-1}$ $h^{-1}$. Arterial pressure was monitored from a femoral, superficial tibial, or radial (22 gauge) cannula. Heart rate was measured by tachograph from the arterial pulse wave. Core temperature was kept at 36.5-38.0° C. by warming blankets. Electrocardiogram and pulse oximetry were monitored continuously.

Needle electrodes (25 gauge) transmitting square-wave pulses of 0.2 msec duration at supramaximal voltage which were generated by a Grass S-88 stimulator (Grass Instruments, Quincy, Mass.) were placed at the peroneal nerve at the knee to elicit twitch responses of the extensor digitorum of the foot at 0.15 Hz. A small slip (10-20%) of the tendon was dissected free under sterile technique and tied to a Grass FT 10 force transducer (Grass Instruments, Quincy, Mass.) at a baseline tension of 50 gm. Train-of four stimulation (TOF, 2 Hz for 2 sec) was interposed at appropriate points, especially 1-2 min prior to NMBA dosing and following recovery of twitch to 95% of baseline, where TOF was subsequently evaluated every 1-2 min.

Recordings of circulatory and neuromuscular data were made on a Grass 7B polygraph (Grass Instruments). A baseline period of 15-20 min was allowed for stabilization of recordings prior to dosing.[2]

At the end of each experiment, animals were awakened, analgesics were given per veterinary practice, and animals were returned to their domiciles and attended until standing.

Determination of Neuromuscular Blocking Potency and Duration

Dose-response curves for twitch blockade by gantacurium, CW 002, CW 011, cisatracurium, CW002-Cys, NB 938-69, NB 1064-81, NB 802-17 (CW 001), NB 832-65, and NB 1163-79, structures of which are all shown above, were generated as follows. To ensure minimal cumulative/residual influence on these data, sequential dosing was done in escalating fashion. Successive doses were separated by at least three estimated half lives beyond complete recovery of the previous dose to TOF of 110-120%, which is normal for these monkeys. Only the first one or two doses yielding 5 to 99% blockade were included from any single experiment for computation of dose-response data.

Comparative studies of spontaneous recovery versus antagonism/reversal were done at least 3 estimated half-lives following dose-response studies.

ED 50 and ED 95 were computed from the regression of log dose vs. the logit of percentage blockade of twitch.

Reversal of Neuromuscular Blockade by Cysteine

Definitions

ED 95: The calculated dose required for 95% block of twitch
TOF Train-of-four ratio, T4/T1 following 2 Hz for 2 sec stimulation
Duration of action: Duration from injection to recovery of twitch to 95% of control height
5-95% recovery time: Time interval for twitch recovery from 5% to 95% twitch height
Classical Reversal or Antagonism: Antagonism of blockade at 2% twitch height
Immediate Reversal or Antagonism: Antagonism of blockade at 1 min following injection of 2-6×ED95 dose of the NMB
Full Reversal or Complete Reversal or Complete Antagonism: Recovery of twitch to 95 percent or more of control height, and TOF to a value of 100% or more
Chemical Reversal: Abolition of neuromuscular blockade by conversion of the active neuromuscular blocking drug to an inactive derivative in a purely chemical reaction requiring no enzymatic catalyst
Fully Effective Dose of Cysteine: Dose required to restore neuromuscular function to normal, i.e., twitch>95% and TOF 100% or more, within 5 minutes or less.

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

What is claimed is:
1. A neuromuscular blocking agent of formula (I)

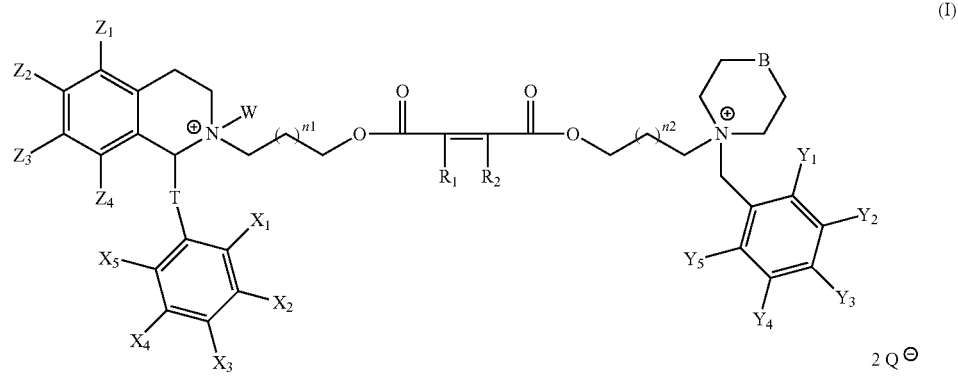

wherein each of $R_1$ and $R_2$ is independently selected from the group hydrogen and halogen, and $R_1$ and $R_2$ can be disposed in a cis or a trans configuration on the two double-bonded carbon atoms to which $R_1$ and $R_2$ are respectively bonded;

T is selected from the group $CH_2$ and $CH_3$, wherein if T is $CH_3$, the phenyl group with the $X_1$-$X_5$ substituents is not present;

B is selected from the group $CH_2$, O, NR, and a direct single bond, wherein R is H, $(C_{1-6})$alkyl, or $(C_{1-6})$acyl;

n1 and n2 are each independently equal to 0, 1, 2, or 3;

each of $X_1$, $X_2$, $X_3$, $X_4$, and $X_5$, is independently at each occurrence hydrogen, hydroxy or methoxy, or any two adjacent $X_1$, $X_2$, $X_3$, $X_4$, or $X_5$, together form a methylenedioxy or ethylenedioxy group; each of $Y_1$, $Y_2$, $Y_3$, $Y_4$, and $Y_5$, is independently at each occurrence hydrogen, hydroxy or methoxy, or any two adjacent $Y_1$, $Y_2$, $Y_3$, $Y_4$, or $Y_5$, together form a methylenedioxy or ethylenedioxy group;

each of $Z_1$, $Z_2$, $Z_3$, and $Z_4$, is independently at each occurrence hydrogen, hydroxy or methoxy, or any two adjacent $Z_1$, $Z_2$, $Z_3$, or $Z_4$, together form a methylenedioxy or ethylenedioxy group;

W is selected from methyl and a benzyl group of formula:

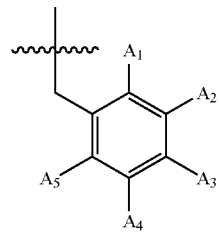

wherein each of $A_1$, $A_2$ $A_3$, $A_4$, and $A_5$, is independently at each occurrence hydrogen or methoxy, or any two adjacent $A_1$, $A_2$ $A_3$, $A_4$, or $A_5$, together form a methylenedioxy or ethylenedioxy group, and a wavy line indicates a point of bonding; and, wherein each $Q^\ominus$ is an independently selected pharmaceutically acceptable anion.

2. The neuromuscular blocking agent of claim 1 of formula (IR)

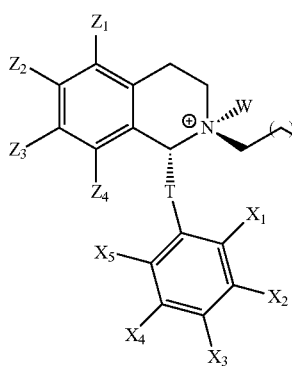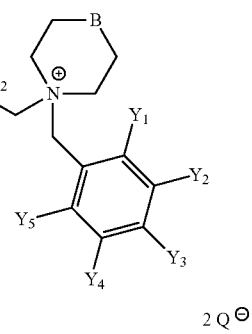

(IR)

wherein $R_1$, $R_2$, n1, n2, $X_1$, $X_2$, $X_3$, $X_4$, $X_5$, $Y_1$, $Y_2$, $Y_3$, $Y_4$, $Y_5$, $Z_1$, $Z_2$, $Z_3$, $Z_4$, $A_1$, $A_2$, $A_3$, $A_4$, $A_5$, W, B, $Q^\ominus$, and T are as defined in claim 1.

3. The neuromuscular blocking agent of claim 1 of formula (IS)

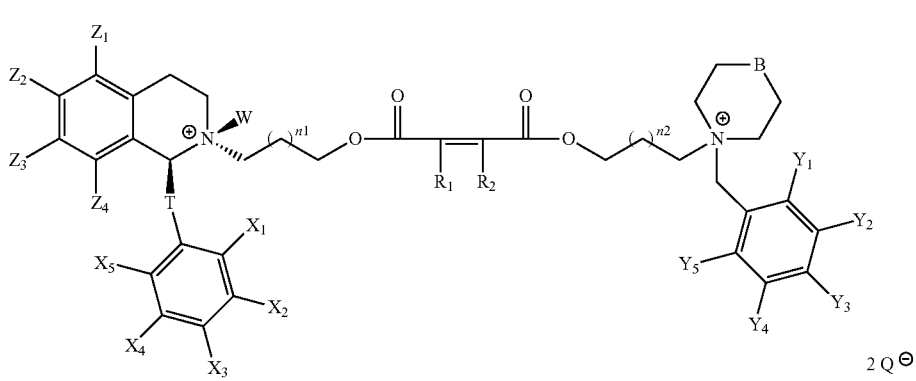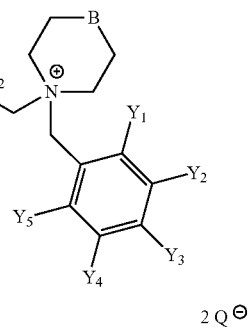

(IS)

wherein $R_1$, $R_2$, n1, n2, $X_1$, $X_2$, $X_3$, $X_4$, $X_5$, $Y_1$, $Y_2$, $Y_3$, $Y_4$, $Y_5$, $Z_1$, $Z_2$, $Z_3$, $Z_4$, $A_1$, $A_2$, $A_3$, $A_4$, $A_5$, W, B, $Q^\ominus$, and T are as defined in claim 1.

4. The neuromuscular blocking agent of claim 1 wherein at least one of $X_1$, $X_2$, $X_3$, $X_4$, or $X_5$, is non-hydrogen; or at least one of $Y_1$, $Y_2$, $Y_3$, $Y_4$, or $Y_5$, is non-hydrogen; or at least one of $Z_1$, $Z_2$, $Z_3$, or $Z_4$, is non-hydrogen; or at least one of $A_1$, $A_2$, $A_3$, $A_4$, or $A_5$, is non-hydrogen; or any combination thereof.

5. The neuromuscular blocking agent of claim 1 wherein $X_2$ and $X_3$ are both methoxy or together form methylenedioxy or ethylenedioxy, or $Y_2$ and $Y_3$ are both methoxy or together form methylenedioxy or ethylenedioxy, or $Z_2$ and $Z_3$ are both methoxy or together form methylenedioxy or ethylenedioxy, or any combination thereof.

6. The neuromuscular blocking agent of claim 1 wherein T is $CH_2$ and the phenyl ring bearing $X_1$-$X_5$ is present.

7. The neuromuscular blocking agent of claim 1 wherein B is oxygen.

8. The neuromuscular blocking agent of claim 1 wherein B is a direct single bond.

9. The neuromuscular blocking agent of claim 1 wherein n1 and n2 are each equal to 1.

10. The neuromuscular blocking agent of claim 1 comprising a maleate diester selected from the group:

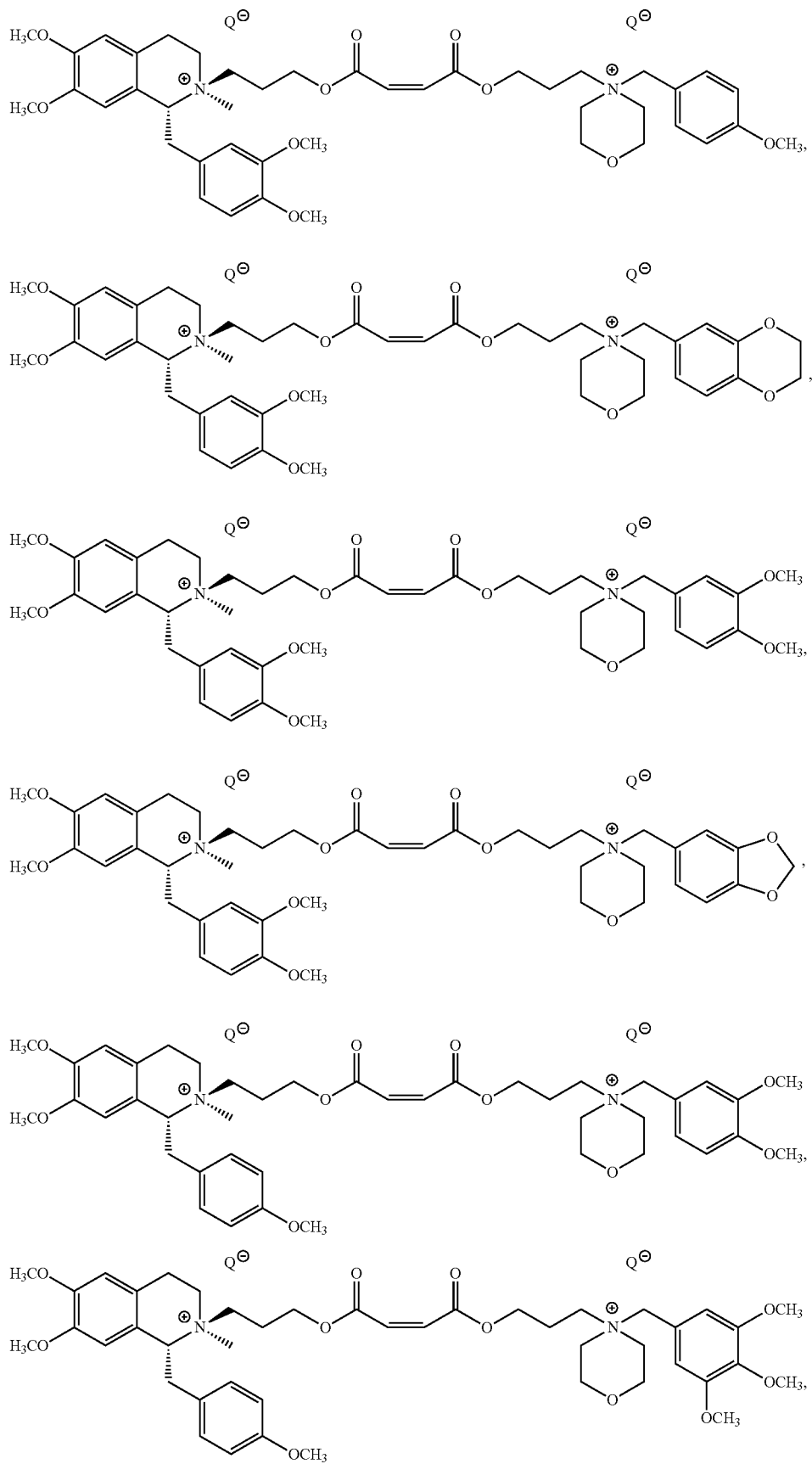

-continued
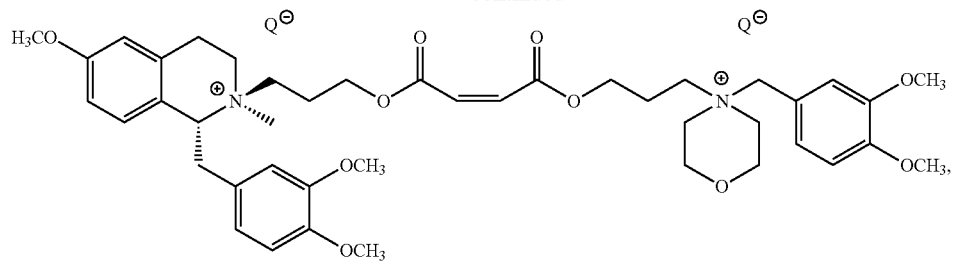
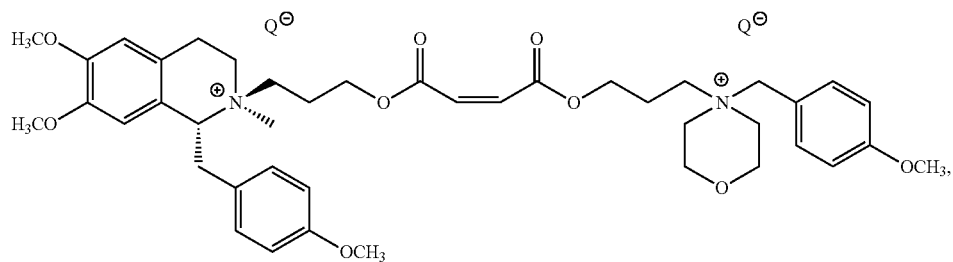
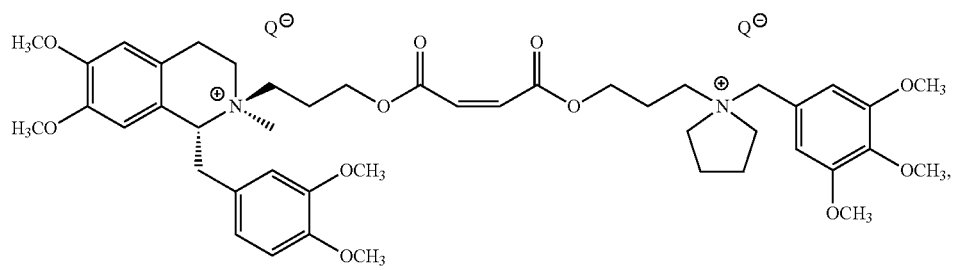
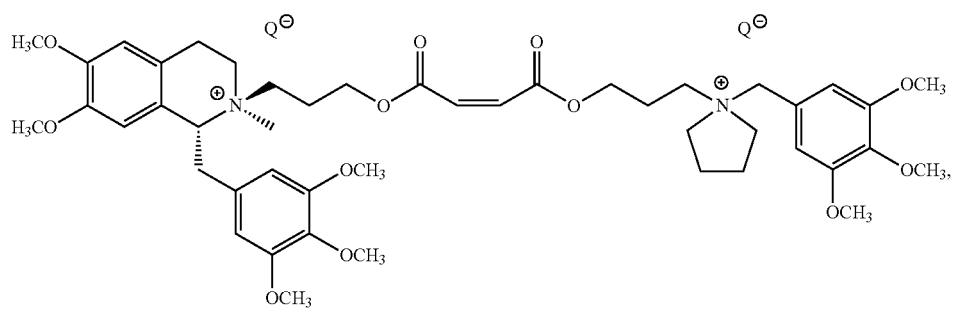
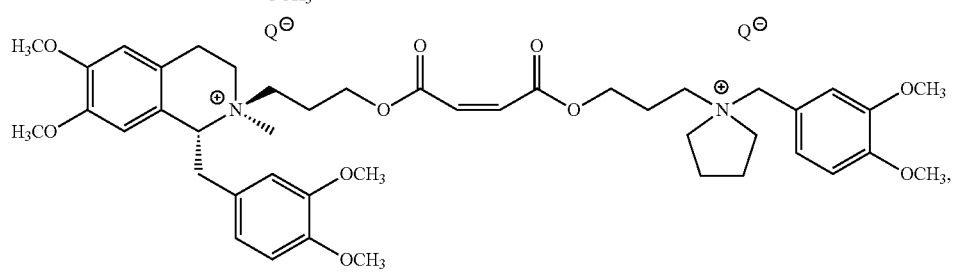
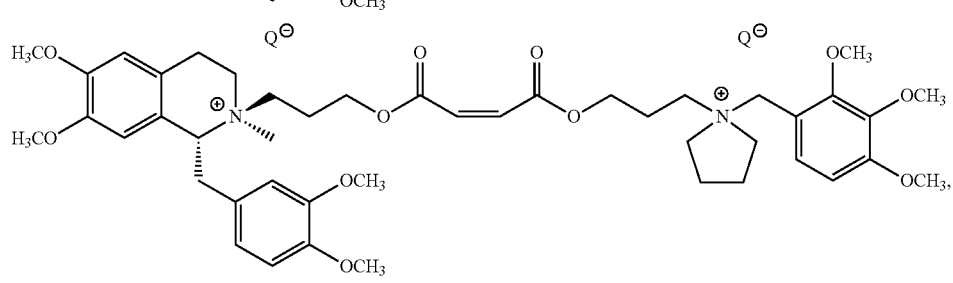

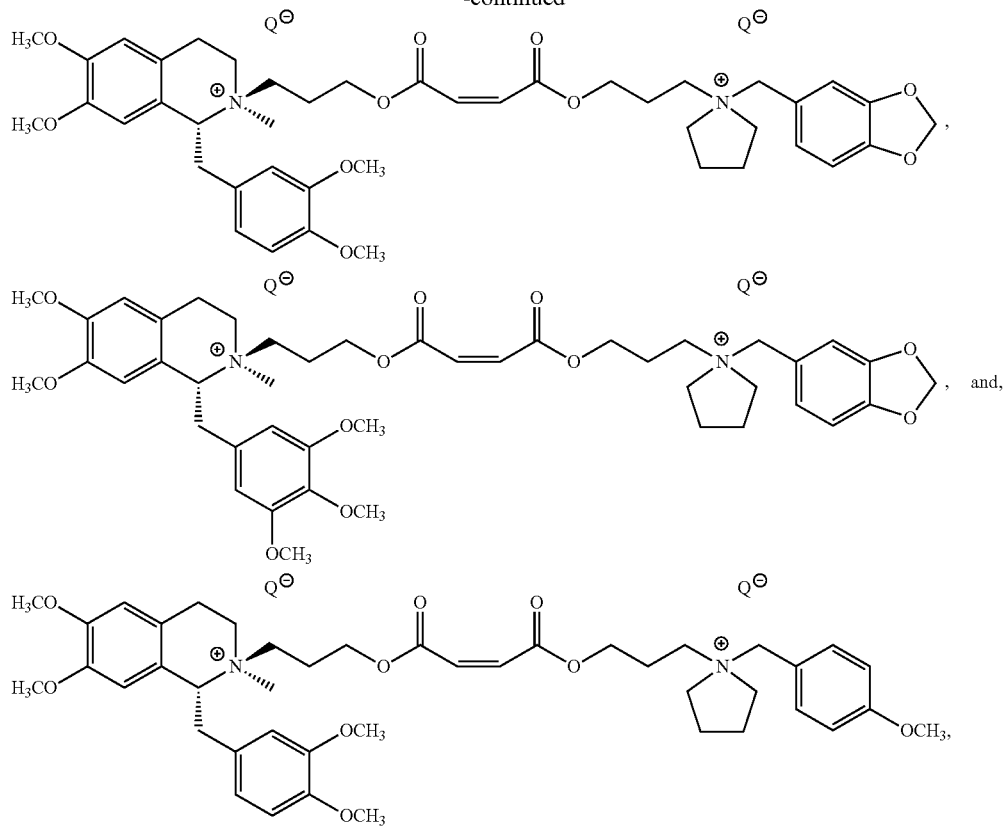
wherein each $Q^\ominus$ is an independently selected pharmaceutically acceptable anion.
11. The neuromuscular blocking agent of claim 1 comprising a chlorofumarate diester selected from the group:
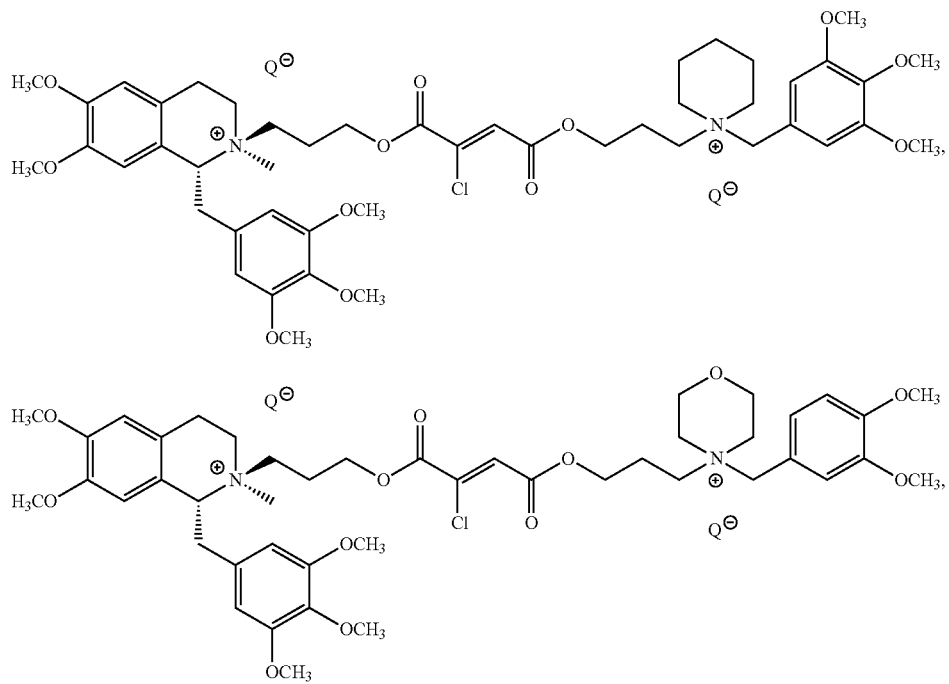

-continued
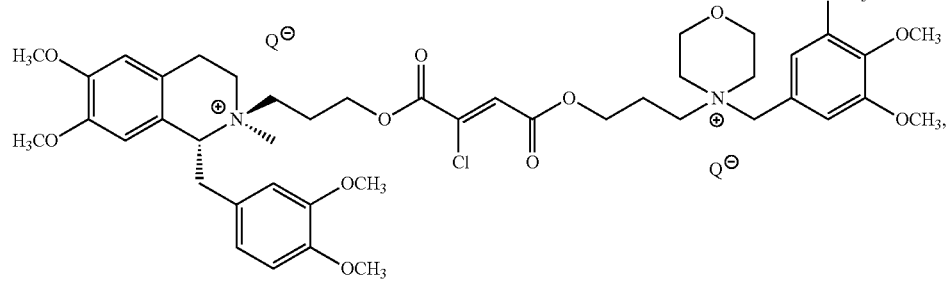
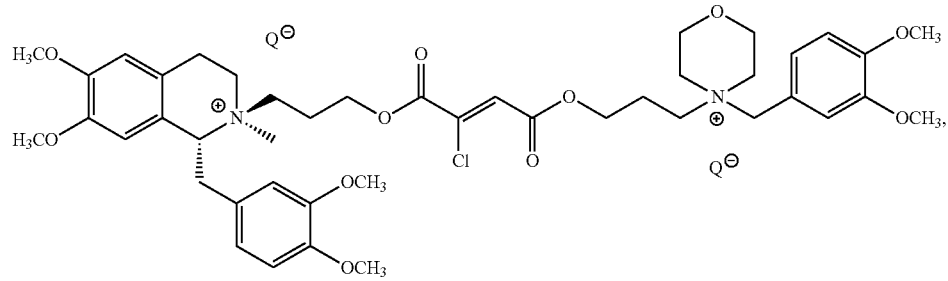
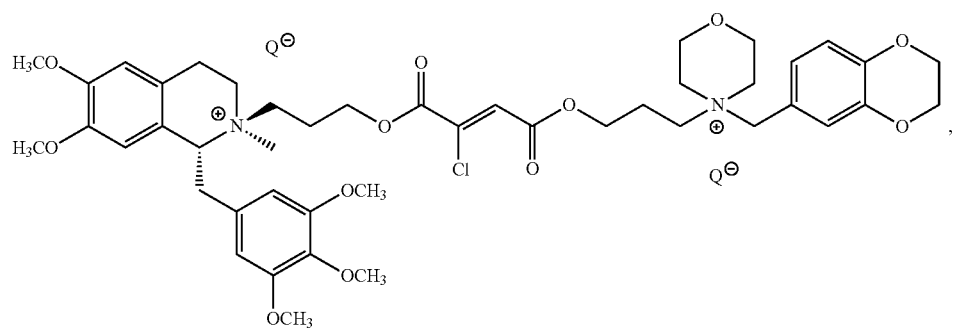
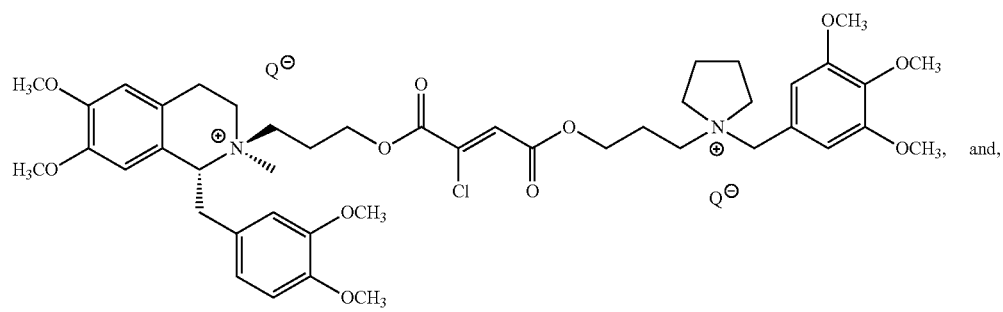
and,
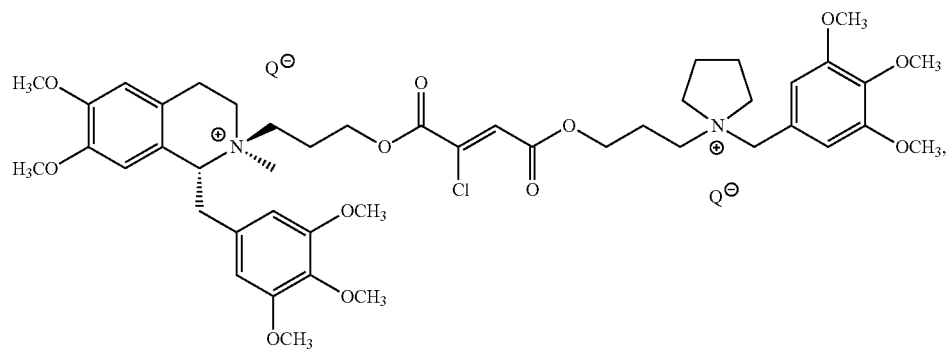

wherein each $Q^\ominus$ is an independently selected pharmaceutically acceptable anion.

12. A neuromuscular blocking agent of formula

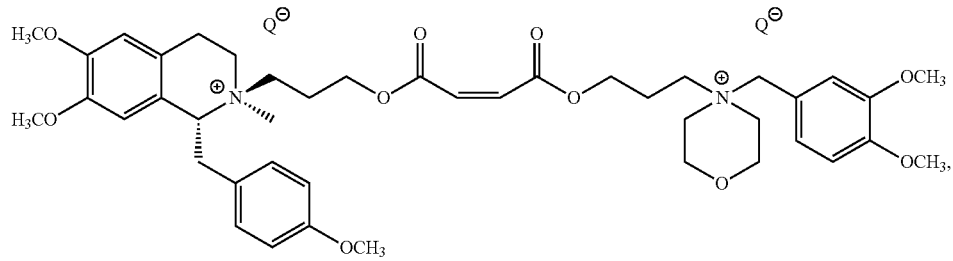

wherein each $Q^\ominus$ is an independently selected pharmaceutically acceptable anion.

13. The neuromuscular blocking agent of claim 1 wherein the compound produces, upon administration of an effective amount of the compound to a patient, a neuromuscular blockade.

14. The neuromuscular blocking agent of claim 13 wherein the effective amount is about 0.01-10 mg per kg patient bodyweight.

15. The neuromuscular blocking agent of claim 13 wherein the effective amount is about 0.1-1 mg per kg patient bodyweight.

16. The neuromuscular blocking agent of claim 13 wherein the neuromuscular blockage is reversible by administration to the patient of an effective amount of a thiol compound.

17. The neuromuscular blocking agent of claim 16 wherein the thiol compound is L-cysteine or a pharmaceutically acceptable salt thereof, D-cysteine or a pharmaceutically acceptable salt thereof, or glutathione or a pharmaceutically acceptable salt thereof.

18. A dosage form comprising an amount of the neuromuscular blocking agent of claim 1 that is sufficient to paralyze a mammalian subject, in a suitable biocompatible solvent.

19. The dosage form of claim 18 adapted for parenteral administration to the mammalian subject.

20. A method of inducing a neuromuscular blockade in a mammal comprising administering to the mammal the neuromuscular blocking agent of claim 1.

21. The method of claim 20, wherein the mammal is subjected to general anesthesia.

22. The method of claim 20, wherein the mammal is undergoing a surgical procedure.

23. The method of claim 20, wherein the mammal is a human, or is a domestic or zoo animal.

24. A method of reversing a neuromuscular blockade in a mammal comprising administering to the mammal of an effective amount of at least one of L-cysteine, D-cysteine, or a mixture thereof; N-acetylcysteine; glutathione; homocysteine; methionine; S-adenosyl-methionine; or penicillamine; or a pharmaceutically acceptable salt thereof; wherein the neuromuscular blockade is generated by administering to the mammal a neuromuscular blocking agent of formula (I)

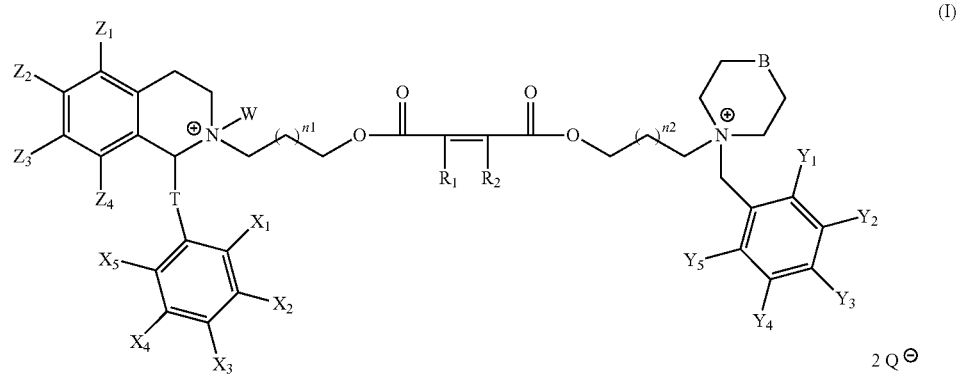

(I)

wherein each of $R_1$ and $R_2$ is independently selected from the group hydrogen and halogen, and $R_1$ and $R_2$ can be disposed in a cis or a trans configuration on the two double-bonded carbon atoms to which $R_1$ and $R_2$ are respectively bonded;

T is selected from the group $CH_2$ and $CH_3$, wherein if T is $CH_3$, the phenyl group with the $X_1$-$X_5$ substituents is not present;

B is selected from the group $CH_2$, O, NR, and a direct single bond, wherein R is H, $(C_{1-6})$alkyl, or $(C_{1-6})$acyl;

n1 and n2 are each independently equal to 0, 1, 2, or 3;

each of $X_1$, $X_2$, $X_3$, $X_4$, and $X_5$, is independently at each occurrence hydrogen, hydroxy or methoxy, or any two adjacent $X_1$, $X_2$, $X_3$, $X_4$, or $X_5$, together form a methylenedioxy or ethylenedioxy group; each of $Y_1$, $Y_2$, $Y_3$, $Y_4$, and $Y_5$, is independently at each occurrence hydrogen, hydroxy or methoxy, or any two adjacent $Y_1, Y_2, Y_3, Y_4$, or $Y_5$, together form a methylenedioxy or ethylenedioxy group;

each of $Z_1, Z_2, Z_3$, and $Z_4$, is independently at each occurrence hydrogen, hydroxy or methoxy, or any two adjacent $Z_1, Z_2, Z_3$, or $Z_4$, together form a methylenedioxy or ethylenedioxy group;

W is selected from methyl and a benzyl group of formula:

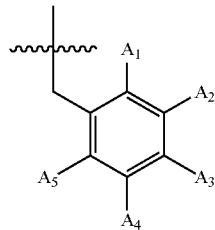

wherein each of $A_1, A_2, A_3, A_4$, and $A_5$, is independently at each occurrence hydrogen or methoxy, or any two adjacent $A_1, A_2, A_3, A_4$, or $A_5$, together form a methylenedioxy or ethylenedioxy group, and a wavy line indicates a point of bonding; and, wherein each $Q^\ominus$ is an independently selected pharmaceutically acceptable anion.

25. The method of claim 24, wherein D-cysteine or a pharmaceutically acceptable salt thereof is administered.

26. The method of claim 24, wherein the effective amount is administered intravenously, in combination with a pharmaceutically acceptable liquid carrier.

27. The method of claim 24, wherein the effective amount is administered in a dosage of about 0.1 mg/kg to about 500 mg/kg.

28. The method of claim 24, wherein the mammal is a domestic or zoo animal.

29. The method of claim 24, wherein the mammal is a human.

30. A kit comprising:
(a) an effective amount of a neuromuscular blocking agent of claim 1,
(b) an effective amount of an antagonist to the neuromuscular blocking agent comprising at least one of L-cysteine, D-cysteine, or a mixture thereof; N-acetylcysteine; glutathione; homocysteine; methionine; S-adenosyl-methionine; or penicillamine; or a pharmaceutically acceptable salt thereof; and
(c) instructions informing the user how to employ the antagonist to reverse the effects of the neuromuscular blocking agent on the mammal to which the blocking agent is administered.

31. The kit of claim 30, wherein (a), (b), and (c) are separately packaged.

32. The kit of claim 30, wherein the neuromuscular blocking agent is a powder or water soluble solid.

33. The kit of claim 30, wherein the antagonist to the neuromuscular blocking agent is a powder or soluble solid.

34. The kit of claim 30, wherein the neuromuscular blocking agent and the antagonist thereof are administered intravenously, in combination with a pharmaceutically acceptable liquid carrier, and the instructions include directions for mixing the powder or soluble solid with a pharmaceutically acceptable liquid carrier.

35. The kit of claim 30, wherein the antagonist is cysteine selected from the group L cysteine, D-cysteine, a pharmaceutically acceptable salt thereof, and any combination thereof.

* * * * *

UNITED STATES PATENT AND TRADEMARK OFFICE
CERTIFICATE OF CORRECTION

PATENT NO. : 9,156,826 B2  
APPLICATION NO. : 14/411060  
DATED : October 13, 2015  
INVENTOR(S) : Savarese et al.

Page 1 of 1

It is certified that error appears in the above-identified patent and that said Letters Patent is hereby corrected as shown below:

In the claims

In column 77, line 17 (Approx.), in Claim 1, delete "$A_2\ A_3$," and insert --$A_2, A_3$,--, therefor In column 77, line 19 (Approx.), in Claim 1, delete "$A_2\ A_3$," and insert --$A_2, A_3$,--, therefor In column 89, line 21 (Approx.), in Claim 24, delete "$A_2\ A_3$," and insert --$A_2, A_3$,--, therefor In column 89, line 23 (Approx.), in Claim 24, delete "$A_2\ A_3$," and insert --$A_2, A_3$,--, therefor Signed and Sealed this  
Seventh Day of June, 2016

Michelle K. Lee  
*Director of the United States Patent and Trademark Office*